(12) United States Patent
Predick et al.

(10) Patent No.: US 11,896,494 B2
(45) Date of Patent: Feb. 13, 2024

(54) EXPANDABLE IMPLANT ASSEMBLY

(71) Applicant: Life Spine, Inc., Huntley, IL (US)

(72) Inventors: Daniel P. Predick, Wheat Ridge, CO (US); Madeline Wolters, Carol Stream, IL (US); Michael S. Butler, St. Charles, IL (US)

(73) Assignee: Life Spine, Inc., Huntley, IL (US)

( * ) Notice: Subject to any disclaimer, the term of this patent is extended or adjusted under 35 U.S.C. 154(b) by 1060 days.

(21) Appl. No.: 16/438,031

(22) Filed: Jun. 11, 2019

(65) Prior Publication Data

US 2019/0290448 A1 Sep. 26, 2019

Related U.S. Application Data

(63) Continuation-in-part of application No. PCT/US2018/041306, filed on Jul. 9, 2018, which is
(Continued)

(51) Int. Cl.
*A61F 2/44* (2006.01)
*A61F 2/46* (2006.01)
*A61F 2/30* (2006.01)

(52) U.S. Cl.
CPC .......... *A61F 2/4455* (2013.01); *A61F 2/4611* (2013.01); *A61F 2002/3054* (2013.01);
(Continued)

(58) Field of Classification Search
CPC .............................. A61F 2/4455; A61F 2/4611
See application file for complete search history.

(56) References Cited

U.S. PATENT DOCUMENTS

| 904,434 A | 11/1908 | Huff |
| 1,925,385 A | 9/1933 | Humes |
(Continued)

FOREIGN PATENT DOCUMENTS

| CN | 102427769 A | 4/2012 |
| CN | 205866898 U | 1/2017 |
(Continued)

OTHER PUBLICATIONS

Folman, et al., "Posterior Lumbar Interbody Fusion for Degenerative Disc Disease Using a Minimally Invasive B-Twin Expandable Spinal Spacer." Journal of Spinal Disorders & Techniques. 2003, vol. 16, No. 5, pp. 455-460.
(Continued)

*Primary Examiner* — Bruce E Snow
(74) *Attorney, Agent, or Firm* — Foley & Lardner LLP

(57) ABSTRACT

An expandable implant includes an upper main support, a lower main support, an upper pivoting support, and a lower pivoting support. The upper main support and the upper pivoting support are configured to engage a first portion of bone, and the lower main support is coupled to the upper main support and configured to engage a second portion of bone. The upper main support is adjustable relative to the lower main support to adjust height of the implant. The upper pivoting support is rotatably movable relative to the upper main support. The lower pivoting support is coupled to the upper pivoting support, configured to engage the second bone portion, and is rotatably movable relative to the lower main support. Adjusting the upper main support relative to the lower main support causes adjustment of the upper pivoting support relative to the lower pivoting support.

14 Claims, 32 Drawing Sheets

Related U.S. Application Data a continuation-in-part of application No. 15/645,179, filed on Jul. 10, 2017, now Pat. No. 10,154,911.

(52) U.S. Cl.
CPC .............. *A61F 2002/30172* (2013.01); *A61F 2002/30261* (2013.01); *A61F 2002/30405* (2013.01); *A61F 2002/30471* (2013.01); *A61F 2002/30556* (2013.01); *A61F 2002/30579* (2013.01)

(56) References Cited

U.S. PATENT DOCUMENTS

| | | |
|---|---|---|
| 3,846,846 A | 11/1974 | Fischer |
| 4,466,426 A | 8/1984 | Blackman |
| 4,636,217 A | 1/1987 | Ogilvie et al. |
| 4,743,256 A | 5/1988 | Brantigan |
| 4,863,476 A | 9/1989 | Shepperd |
| 5,098,435 A | 3/1992 | Stednitz et al. |
| 5,192,327 A | 3/1993 | Brantigan |
| 5,236,460 A | 8/1993 | Barber |
| 5,390,683 A | 2/1995 | Pisharodi |
| 5,522,899 A | 6/1996 | Michelson |
| 5,609,635 A | 3/1997 | Michelson |
| 5,645,599 A | 7/1997 | Samani |
| 5,658,335 A | 8/1997 | Allen |
| 5,658,337 A | 8/1997 | Kohrs et al. |
| 5,776,199 A | 7/1998 | Michelson |
| 5,836,948 A | 11/1998 | Zucherman et al. |
| 5,860,977 A | 1/1999 | Zucherman et al. |
| 5,876,404 A | 3/1999 | Zucherman et al. |
| 6,045,579 A | 4/2000 | Hochshuler et al. |
| 6,048,342 A | 4/2000 | Zucherman et al. |
| 6,068,630 A | 5/2000 | Zucherman et al. |
| 6,074,390 A | 6/2000 | Zucherman et al. |
| 6,080,193 A | 6/2000 | Hochshuler et al. |
| 6,113,638 A | 9/2000 | Williams et al. |
| 6,126,689 A | 10/2000 | Brett |
| 6,129,763 A | 10/2000 | Chauvin et al. |
| 6,176,882 B1 | 1/2001 | Biedermann et al. |
| 6,183,471 B1 | 2/2001 | Zucherman et al. |
| 6,190,387 B1 | 2/2001 | Zucherman et al. |
| 6,235,030 B1 | 5/2001 | Zucherman et al. |
| 6,290,724 B1 | 9/2001 | Marino |
| 6,302,914 B1 | 10/2001 | Michelson |
| 6,375,682 B1 | 4/2002 | Fleischmann et al. |
| 6,409,766 B1 | 6/2002 | Brett |
| 6,443,989 B1 | 9/2002 | Jackson |
| 6,443,990 B1 | 9/2002 | Aebi et al. |
| 6,447,544 B1 | 9/2002 | Michelson |
| 6,451,019 B1 | 9/2002 | Zucherman et al. |
| 6,491,724 B1 | 12/2002 | Ferree |
| 6,494,883 B1 | 12/2002 | Ferree |
| 6,537,320 B1 | 3/2003 | Michelson |
| 6,576,016 B1 | 6/2003 | Hochshuler et al. |
| 6,613,091 B1 | 9/2003 | Zdeblick et al. |
| 6,641,614 B1 | 11/2003 | Wagner et al. |
| 6,648,917 B2 | 11/2003 | Gerbec et al. |
| 6,685,742 B1 | 2/2004 | Jackson |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,706,070 B1 | 3/2004 | Wagner et al. |
| 6,752,832 B2 | 6/2004 | Neumann |
| 6,773,460 B2 | 8/2004 | Jackson |
| 6,796,983 B1 | 9/2004 | Zucherman et al. |
| 6,800,092 B1 | 10/2004 | Williams et al. |
| 6,849,093 B2 | 2/2005 | Michelson |
| 7,001,385 B2 | 2/2006 | Bonutti |
| 7,048,736 B2 | 5/2006 | Robinson et al. |
| 7,087,055 B2 | 8/2006 | Lim et al. |
| 7,101,375 B2 | 9/2006 | Zucherman et al. |
| 7,214,243 B2 | 5/2007 | Taylor |
| 7,217,291 B2 | 5/2007 | Zucherman et al. |
| 7,220,280 B2 | 5/2007 | Kast et al. |
| 7,250,055 B1 | 7/2007 | Vanderwalle |
| 7,473,276 B2 | 1/2009 | Aebi et al. |
| 7,503,933 B2 | 3/2009 | Michelson |
| 7,621,950 B1 | 11/2009 | Globerman et al. |
| 7,695,513 B2 | 4/2010 | Zucherman et al. |
| 7,722,674 B1 | 5/2010 | Grotz |
| 7,727,280 B2 | 6/2010 | McLuen |
| 7,731,751 B2 | 6/2010 | Butler et al. |
| 7,789,914 B2 | 9/2010 | Michelson |
| D626,233 S | 10/2010 | Cipoletti et al. |
| 7,824,427 B2 | 11/2010 | Perez-Cruet et al. |
| 7,828,849 B2 | 11/2010 | Lim |
| 7,837,734 B2 | 11/2010 | Zucherman et al. |
| 7,846,188 B2 | 12/2010 | Moskowitz et al. |
| 7,850,733 B2 | 12/2010 | Baynham et al. |
| 7,854,766 B2 | 12/2010 | Moskowitz et al. |
| 7,867,277 B1 | 1/2011 | Tohmeh |
| 7,879,098 B1 | 2/2011 | Simmons, Jr. |
| 7,942,903 B2 | 5/2011 | Moskowitz et al. |
| 7,959,675 B2 | 6/2011 | Gately |
| 7,972,363 B2 | 7/2011 | Moskowitz et al. |
| 8,016,861 B2 | 9/2011 | Mitchell et al. |
| 8,021,430 B2 | 9/2011 | Michelson |
| 8,048,117 B2 | 11/2011 | Zucherman et al. |
| 8,062,375 B2 | 11/2011 | Glerum et al. |
| 8,070,817 B2 | 12/2011 | Gradl et al. |
| 8,071,007 B1 | 12/2011 | Teoh et al. |
| 8,105,382 B2 * | 1/2012 | Olmos .................... A61F 2/447 623/17.15 |
| 8,187,332 B2 | 5/2012 | McLuen |
| 8,231,656 B2 | 7/2012 | Lee et al. |
| 8,241,330 B2 | 8/2012 | Lamborne et al. |
| 8,241,364 B2 | 8/2012 | Hansell et al. |
| 8,257,370 B2 | 9/2012 | Moskowitz et al. |
| 8,267,939 B2 | 9/2012 | Cipoletti et al. |
| 8,303,663 B2 | 11/2012 | Jimenez et al. |
| 8,308,804 B2 | 11/2012 | Krueger |
| 8,343,190 B1 | 1/2013 | Mueller et al. |
| 8,353,913 B2 | 1/2013 | Moskowitz et al. |
| 8,353,963 B2 | 1/2013 | Glerum |
| 8,366,777 B2 | 2/2013 | Matthis et al. |
| 8,382,801 B2 | 2/2013 | Lamborne et al. |
| 8,382,842 B2 | 2/2013 | Greenhalgh et al. |
| 8,388,686 B2 | 3/2013 | Aebi et al. |
| 8,394,129 B2 | 3/2013 | Lopez et al. |
| 8,398,713 B2 | 3/2013 | Weiman |
| 8,425,607 B2 | 4/2013 | Waugh et al. |
| 8,435,298 B2 | 5/2013 | Weiman |
| 8,444,696 B2 | 5/2013 | Michelson |
| 8,454,706 B2 | 6/2013 | De Beaubien |
| 8,491,659 B2 | 7/2013 | Weiman |
| 8,506,629 B2 | 8/2013 | Weiland |
| 8,518,120 B2 | 8/2013 | Glerum et al. |
| 8,523,944 B2 | 9/2013 | Jimenez et al. |
| 8,529,628 B2 | 9/2013 | Marino et al. |
| 8,535,380 B2 | 9/2013 | Greenhalgh et al. |
| 8,551,173 B2 | 10/2013 | Lechmann et al. |
| 8,556,979 B2 | 10/2013 | Glerum et al. |
| 8,568,481 B2 | 10/2013 | Olmos et al. |
| 8,597,360 B2 | 12/2013 | McLuen et al. |
| 8,628,578 B2 | 1/2014 | Miller et al. |
| 8,632,595 B2 | 1/2014 | Weiman |
| 8,641,764 B2 | 2/2014 | Gately |
| 8,641,766 B2 | 2/2014 | Donner et al. |
| 8,663,332 B1 | 3/2014 | To et al. |
| 8,679,183 B2 | 3/2014 | Glerum et al. |
| 8,685,098 B2 | 4/2014 | Glerum et al. |
| 8,690,883 B2 | 4/2014 | Collins et al. |
| 8,702,798 B2 | 4/2014 | Matthis et al. |
| 8,709,086 B2 | 4/2014 | Glerum |
| 8,734,516 B2 | 5/2014 | Moskowitz et al. |
| 8,795,366 B2 | 8/2014 | Varela |
| 8,821,506 B2 | 9/2014 | Mitchell |
| 8,845,728 B1 | 9/2014 | Abdou |
| 8,845,731 B2 | 9/2014 | Weiman |
| 8,845,732 B2 | 9/2014 | Weiman |
| 8,845,734 B2 | 9/2014 | Weiman |
| 8,852,279 B2 | 10/2014 | Weiman |

(56) References Cited

U.S. PATENT DOCUMENTS

| | | |
|---|---|---|
| 8,858,638 B2 | 10/2014 | Michelson |
| 8,864,833 B2 | 10/2014 | Glerum et al. |
| 8,888,853 B2 | 11/2014 | Glerum et al. |
| 8,888,854 B2 | 11/2014 | Glerum et al. |
| 8,894,711 B2 | 11/2014 | Varela |
| 8,894,712 B2 | 11/2014 | Varela |
| 8,906,095 B2 | 12/2014 | Christensen et al. |
| 8,926,704 B2 | 1/2015 | Glerum et al. |
| 8,936,641 B2 | 1/2015 | Cain |
| 8,940,052 B2 | 1/2015 | Lechmann et al. |
| 8,974,505 B2 | 3/2015 | Sawa et al. |
| 9,005,293 B2 | 4/2015 | Moskowitz et al. |
| 9,034,041 B2 | 5/2015 | Wolters et al. |
| 9,034,045 B2 | 5/2015 | Davenport et al. |
| 9,039,771 B2 | 5/2015 | Glerum et al. |
| 9,044,284 B2 | 6/2015 | Sweeney |
| 9,060,876 B1 | 6/2015 | To et al. |
| 9,101,487 B2 | 8/2015 | Petersheim |
| 9,119,730 B2 | 9/2015 | Glerum et al. |
| 9,125,757 B2 | 9/2015 | Weiman |
| 9,149,367 B2 | 10/2015 | Davenport et al. |
| 9,186,258 B2 | 11/2015 | Davenport et al. |
| 9,186,262 B2 | 11/2015 | McLuen et al. |
| 9,198,772 B2 | 12/2015 | Weiman |
| 9,204,922 B2 | 12/2015 | Hooven |
| 9,204,972 B2 | 12/2015 | Weiman et al. |
| 9,204,974 B2 | 12/2015 | Glerum et al. |
| 9,211,196 B2 | 12/2015 | Glerum et al. |
| 9,216,095 B2 | 12/2015 | Glerum et al. |
| 9,216,098 B2 | 12/2015 | Trudeau et al. |
| 9,226,836 B2 | 1/2016 | Glerum |
| 9,233,009 B2 | 1/2016 | Gray et al. |
| 9,278,008 B2 | 3/2016 | Perloff et al. |
| 9,295,562 B2 | 3/2016 | Lechmann et al. |
| 9,301,854 B2 | 4/2016 | Moskowitz et al. |
| 9,333,092 B2 | 5/2016 | To et al. |
| 9,358,123 B2 | 6/2016 | McLuen et al. |
| 9,358,126 B2 | 6/2016 | Glerum et al. |
| 9,358,128 B2 | 6/2016 | Glerum et al. |
| 9,358,129 B2 | 6/2016 | Weiman |
| 9,370,434 B2 | 6/2016 | Weiman |
| 9,402,733 B1 | 8/2016 | To et al. |
| 9,402,738 B2 | 8/2016 | Niemiec et al. |
| 9,402,739 B2 | 8/2016 | Weiman et al. |
| 9,408,708 B2 | 8/2016 | Greenhalgh |
| 9,414,932 B2 | 8/2016 | Errico et al. |
| 9,421,111 B2 | 8/2016 | Baynham |
| 9,433,510 B2 | 9/2016 | Lechmann et al. |
| 9,445,919 B2 | 9/2016 | Palmatier et al. |
| 9,452,063 B2 | 9/2016 | Glerum et al. |
| 9,456,903 B2 | 10/2016 | Glerum et al. |
| 9,456,906 B2 | 10/2016 | Gray et al. |
| 9,474,622 B2 | 10/2016 | McLaughlin et al. |
| 9,480,579 B2 | 11/2016 | Davenport et al. |
| 9,486,325 B2 | 11/2016 | Davenport et al. |
| 9,492,286 B2 | 11/2016 | Biedermann et al. |
| 9,492,287 B2 | 11/2016 | Glerum et al. |
| 9,492,289 B2 | 11/2016 | Davenport et al. |
| 9,510,954 B2 | 12/2016 | Glerum et al. |
| 9,517,144 B2 | 12/2016 | McAtamney et al. |
| 9,532,821 B2 | 1/2017 | Moskowitz et al. |
| 9,532,883 B2 | 1/2017 | McLuen et al. |
| 9,539,103 B2 | 1/2017 | McLaughlin et al. |
| 9,539,108 B2 | 1/2017 | Glerum et al. |
| 9,554,918 B2 | 1/2017 | Weiman |
| 9,561,116 B2 | 2/2017 | Weiman et al. |
| 9,561,117 B2 | 2/2017 | Lechmann et al. |
| 9,572,677 B2 | 2/2017 | Davenport et al. |
| 9,579,124 B2 | 2/2017 | Gordon et al. |
| 9,585,765 B2 | 3/2017 | Niemiec et al. |
| 9,597,197 B2 | 3/2017 | Lechmann et al. |
| 9,597,200 B2 | 3/2017 | Glerum et al. |
| 9,603,713 B2 | 3/2017 | Moskowitz et al. |
| 9,610,174 B2 | 4/2017 | Wang et al. |
| 9,622,875 B2 | 4/2017 | Moskowitz et al. |
| 9,622,879 B2 | 4/2017 | Taylor et al. |
| 9,655,737 B2 | 5/2017 | Perloff et al. |
| 9,655,747 B2 | 5/2017 | Glerum et al. |
| 9,662,223 B2 | 5/2017 | Matthis et al. |
| 9,662,224 B2 | 5/2017 | Weiman et al. |
| 9,707,092 B2 | 7/2017 | Davenport et al. |
| 9,770,343 B2 | 9/2017 | Weiman |
| 9,782,265 B2 | 10/2017 | Weiman et al. |
| 9,801,733 B2 | 10/2017 | Wolters et al. |
| 9,814,601 B2 | 11/2017 | Moskowitz et al. |
| 9,833,336 B2 | 12/2017 | Davenport et al. |
| 9,839,528 B2 | 12/2017 | Weiman et al. |
| 9,848,993 B2 | 12/2017 | Moskowitz et al. |
| 9,848,997 B2 | 12/2017 | Glerum et al. |
| 9,848,998 B2 | 12/2017 | Moskowitz et al. |
| 9,855,151 B2 | 1/2018 | Weiman |
| 9,867,719 B2 | 1/2018 | Moskowitz et al. |
| 9,889,022 B2 | 2/2018 | Moskowitz et al. |
| 9,895,238 B2 | 2/2018 | Moskowitz et al. |
| 9,907,673 B2 | 3/2018 | Weiman et al. |
| 9,907,674 B2 | 3/2018 | Moskowitz et al. |
| 9,931,226 B2 | 4/2018 | Kurtaliaj et al. |
| 9,943,418 B2 | 4/2018 | Davenport et al. |
| 9,956,087 B2 | 5/2018 | Seifert et al. |
| 9,962,272 B1 | 5/2018 | Daffinson et al. |
| 9,968,462 B2 | 5/2018 | Weiman |
| 9,974,665 B2 | 5/2018 | McLuen et al. |
| 9,980,822 B2 | 5/2018 | Perloff et al. |
| 9,980,823 B2 | 5/2018 | Matthis et al. |
| 9,987,143 B2 | 6/2018 | Robinson et al. |
| 10,004,607 B2 | 6/2018 | Weiman et al. |
| 10,016,283 B2 | 7/2018 | McLuen et al. |
| 10,028,740 B2 | 7/2018 | Moskowitz et al. |
| 10,028,842 B2 | 7/2018 | Gray et al. |
| 10,034,772 B2 | 7/2018 | Glerum et al. |
| 10,034,773 B2 | 7/2018 | McLaughlin et al. |
| 10,052,213 B2 | 8/2018 | Glerum et al. |
| 10,058,433 B2 | 8/2018 | Lechmann et al. |
| 10,076,367 B2 | 9/2018 | Moskowitz et al. |
| 10,076,423 B2 | 9/2018 | Miller et al. |
| 10,080,669 B2 | 9/2018 | Davenport et al. |
| 10,085,844 B2 | 10/2018 | Perloff et al. |
| 10,085,849 B2 | 10/2018 | Weiman et al. |
| 10,092,417 B2 | 10/2018 | Weiman et al. |
| 10,092,422 B2 | 10/2018 | McLuen et al. |
| 10,098,757 B2 | 10/2018 | Logan et al. |
| 10,098,758 B2 | 10/2018 | Matthews et al. |
| 10,098,759 B2 | 10/2018 | Weiman |
| 10,105,239 B2 | 10/2018 | Niemiec et al. |
| 10,111,760 B2 | 10/2018 | Knapp et al. |
| 10,117,754 B2 | 11/2018 | Davenport et al. |
| 10,137,001 B2 | 11/2018 | Weiman |
| 10,137,007 B2 | 11/2018 | Dewey et al. |
| 10,143,500 B2 | 12/2018 | Niemiec et al. |
| 10,143,569 B2 | 12/2018 | Weiman et al. |
| 10,154,911 B2 | 12/2018 | Predick et al. |
| 10,159,583 B2 | 12/2018 | Dietzel et al. |
| 10,213,321 B2 | 2/2019 | Knapp et al. |
| 10,219,913 B2 | 3/2019 | Matthews et al. |
| 10,226,359 B2 | 3/2019 | Glerum et al. |
| 10,251,643 B2 | 4/2019 | Moskowitz et al. |
| 10,285,819 B2 | 5/2019 | Greenhalgh |
| 10,285,820 B2 | 5/2019 | Greenhalgh |
| 10,292,828 B2 | 5/2019 | Greenhalgh |
| 10,292,830 B2 | 5/2019 | McLuen et al. |
| 10,299,934 B2 | 5/2019 | Seifert et al. |
| 10,307,268 B2 | 6/2019 | Moskowitz et al. |
| 10,350,085 B2 | 7/2019 | Glerum et al. |
| 10,376,386 B2 | 8/2019 | Moskowitz et al. |
| 10,383,741 B2 | 8/2019 | Sutler et al. |
| 10,420,654 B2 | 9/2019 | Logan et al. |
| 10,426,632 B2 | 10/2019 | Butler et al. |
| 10,426,633 B2 | 10/2019 | Moskowitz et al. |
| 10,433,977 B2 | 10/2019 | Lechmann et al. |
| 10,449,058 B2 | 10/2019 | Lechmann et al. |
| 10,470,894 B2 | 11/2019 | Foley et al. |
| 10,478,319 B2 | 11/2019 | Moskowitz et al. |
| 10,512,550 B2 | 12/2019 | Bechtel et al. |
| 10,531,895 B2 | 1/2020 | Weiman et al. |

(56) References Cited

U.S. PATENT DOCUMENTS

| | | |
|---|---|---|
| 10,575,966 B2 | 3/2020 | Logan et al. |
| 10,617,533 B2 | 4/2020 | Glerum et al. |
| 10,624,761 B2 | 4/2020 | Davenport et al. |
| 10,639,166 B2 | 5/2020 | Weiman et al. |
| 10,682,240 B2 | 6/2020 | McLuen et al. |
| 10,702,393 B2 | 7/2020 | Davenport et al. |
| 10,709,569 B2 | 7/2020 | McLaughlin et al. |
| 10,709,571 B2 | 7/2020 | Iott et al. |
| 10,709,573 B2 | 7/2020 | Weiman et al. |
| 10,709,574 B2 | 7/2020 | McLuen et al. |
| 10,722,379 B2 | 7/2020 | McLaughlin et al. |
| 10,729,560 B2 | 8/2020 | Baker et al. |
| 10,729,562 B2 | 8/2020 | Knapp et al. |
| 10,736,754 B2 | 8/2020 | McLuen et al. |
| 10,758,367 B2 | 9/2020 | Weiman et al. |
| 10,765,528 B2 | 9/2020 | Weiman et al. |
| 10,772,737 B2 | 9/2020 | Gray et al. |
| 10,779,957 B2 | 9/2020 | Weiman et al. |
| 10,786,364 B2 | 9/2020 | Davenport et al. |
| 10,799,368 B2 | 10/2020 | Glerum et al. |
| 10,835,387 B2 | 11/2020 | Weiman et al. |
| 10,842,644 B2 | 11/2020 | Weiman et al. |
| 10,869,768 B2 | 12/2020 | Weiman et al. |
| 10,874,522 B2 | 12/2020 | Weiman |
| 10,874,523 B2 | 12/2020 | Weiman et al. |
| 10,925,752 B2 | 2/2021 | Weiman |
| 10,940,014 B2 | 3/2021 | Greenhalgh |
| 10,973,649 B2 | 4/2021 | Weiman et al. |
| 11,020,239 B2 | 6/2021 | Miller et al. |
| 11,051,951 B2 | 7/2021 | Robinson et al. |
| 11,065,128 B2 | 7/2021 | Zappacosta et al. |
| 11,083,584 B2 | 8/2021 | Lauf et al. |
| 11,304,817 B2 | 4/2022 | Altarac et al. |
| 11,304,818 B2 | 4/2022 | Butler et al. |
| 2002/0010472 A1 | 1/2002 | Kuslich et al. |
| 2002/0029084 A1 | 3/2002 | Paul et al. |
| 2002/0128716 A1 | 9/2002 | Cohen et al. |
| 2002/0143343 A1 | 10/2002 | Castro |
| 2002/0143399 A1 | 10/2002 | Sutcliffe |
| 2002/0147461 A1 | 10/2002 | Aldrich et al. |
| 2002/0177897 A1 | 11/2002 | Michelson |
| 2003/0004576 A1 | 1/2003 | Thalgott |
| 2003/0040746 A1 | 2/2003 | Mitchell et al. |
| 2003/0040802 A1 | 2/2003 | Errico et al. |
| 2003/0176926 A1 | 9/2003 | Boehm et al. |
| 2003/0236520 A1 | 12/2003 | Lim et al. |
| 2004/0073213 A1 | 4/2004 | Serhan et al. |
| 2004/0153156 A1 | 8/2004 | Cohen et al. |
| 2004/0167625 A1 | 8/2004 | Beyar et al. |
| 2004/0204747 A1 | 10/2004 | Kemeny et al. |
| 2004/0225292 A1 | 11/2004 | Sasso et al. |
| 2004/0230309 A1 | 11/2004 | Dimauro et al. |
| 2004/0254643 A1 | 12/2004 | Jackson |
| 2005/0027362 A1 | 2/2005 | Williams et al. |
| 2005/0033437 A1 | 2/2005 | Bao et al. |
| 2005/0070911 A1 | 3/2005 | Carrison et al. |
| 2005/0107800 A1 | 5/2005 | Frankel et al. |
| 2005/0119747 A1 | 6/2005 | Fabris Monterumici |
| 2005/0131536 A1 | 6/2005 | Eisermann et al. |
| 2005/0143827 A1 | 6/2005 | Globerman et al. |
| 2005/0177235 A1 | 8/2005 | Baynham et al. |
| 2005/0177236 A1 | 8/2005 | Mathieu et al. |
| 2005/0222681 A1 | 10/2005 | Richley et al. |
| 2005/0228391 A1 | 10/2005 | Levy et al. |
| 2005/0261769 A1 | 11/2005 | Moskowitz et al. |
| 2005/0278036 A1 | 12/2005 | Leonard et al. |
| 2006/0030943 A1 | 2/2006 | Peterman |
| 2006/0036258 A1 | 2/2006 | Zucherman et al. |
| 2006/0084988 A1 | 4/2006 | Kim |
| 2006/0089715 A1 | 4/2006 | Truckai et al. |
| 2006/0089718 A1 | 4/2006 | Zucherman et al. |
| 2006/0095136 A1 | 5/2006 | McLuen |
| 2006/0122701 A1 | 6/2006 | Kiester |
| 2006/0189999 A1 | 8/2006 | Zwirkoski |
| 2006/0241601 A1 | 10/2006 | Trautwein et al. |
| 2006/0241621 A1 | 10/2006 | Moskowitz et al. |
| 2006/0253201 A1 | 11/2006 | McLuen |
| 2006/0264938 A1 | 11/2006 | Zucherman et al. |
| 2006/0265077 A1 | 11/2006 | Zwirkoski |
| 2007/0072475 A1 | 3/2007 | Justin et al. |
| 2007/0142915 A1 | 6/2007 | Altarac et al. |
| 2007/0213739 A1 | 9/2007 | Michelson |
| 2007/0244485 A1 | 10/2007 | Greenhalgh et al. |
| 2007/0270968 A1 | 11/2007 | Baynham et al. |
| 2008/0114367 A1 | 5/2008 | Meyer |
| 2008/0114453 A1 | 5/2008 | Francis |
| 2008/0114456 A1 | 5/2008 | Dewey et al. |
| 2008/0119853 A1 | 5/2008 | Felt et al. |
| 2008/0119945 A1 | 5/2008 | Frigg |
| 2008/0140085 A1 | 6/2008 | Gately et al. |
| 2008/0140207 A1 | 6/2008 | Olmos et al. |
| 2008/0147193 A1 | 6/2008 | Matthis et al. |
| 2008/0161818 A1 | 7/2008 | Kloss et al. |
| 2008/0177391 A1 | 7/2008 | Mitchell et al. |
| 2008/0183211 A1 | 7/2008 | Lamborne et al. |
| 2008/0243251 A1 | 10/2008 | Stad et al. |
| 2008/0288077 A1 | 11/2008 | Reo et al. |
| 2008/0312741 A1 | 12/2008 | Lee et al. |
| 2009/0005872 A1 | 1/2009 | Moumene et al. |
| 2009/0062833 A1 | 3/2009 | Song |
| 2009/0062915 A1 | 3/2009 | Kohm et al. |
| 2009/0105832 A1 | 4/2009 | Allain et al. |
| 2009/0192553 A1 | 7/2009 | Maguire et al. |
| 2009/0198338 A1 | 8/2009 | Phan |
| 2009/0198339 A1 | 8/2009 | Kleiner et al. |
| 2009/0222099 A1 | 9/2009 | Liu et al. |
| 2009/0222100 A1 | 9/2009 | Cipoletti et al. |
| 2009/0312837 A1 | 12/2009 | Eisermann et al. |
| 2010/0082109 A1 | 4/2010 | Greenhalgh et al. |
| 2010/0103344 A1 | 4/2010 | Wang et al. |
| 2010/0179655 A1 | 7/2010 | Hansell et al. |
| 2010/0185291 A1 | 7/2010 | Jimenez et al. |
| 2010/0191336 A1 | 7/2010 | Greenhalgh |
| 2010/0204795 A1 | 8/2010 | Greenhalgh |
| 2010/0211176 A1 | 8/2010 | Greenhalgh |
| 2010/0234889 A1 | 9/2010 | Hess |
| 2010/0241167 A1 | 9/2010 | Taber et al. |
| 2010/0249937 A1 | 9/2010 | Blain et al. |
| 2010/0286777 A1 | 11/2010 | Errico et al. |
| 2011/0022090 A1 | 1/2011 | Gordon et al. |
| 2011/0046682 A1 | 2/2011 | Stephan et al. |
| 2011/0054538 A1 | 3/2011 | Zehavi et al. |
| 2011/0066186 A1 | 3/2011 | Boyer et al. |
| 2011/0071635 A1 | 3/2011 | Zhang et al. |
| 2011/0077738 A1 | 3/2011 | Ciupik et al. |
| 2011/0144692 A1 | 6/2011 | Saladin et al. |
| 2011/0144753 A1 | 6/2011 | Marchek et al. |
| 2011/0144755 A1 | 6/2011 | Baynham et al. |
| 2011/0172709 A1 | 7/2011 | Lyons et al. |
| 2011/0172716 A1 | 7/2011 | Glerum |
| 2011/0172774 A1 | 7/2011 | Varela |
| 2011/0178599 A1 | 7/2011 | Brett |
| 2011/0184468 A1 | 7/2011 | Metcalf et al. |
| 2011/0190817 A1 | 8/2011 | Thommen et al. |
| 2011/0196494 A1 | 8/2011 | Yedlicka et al. |
| 2011/0224731 A1 | 9/2011 | Smisson et al. |
| 2011/0282453 A1 | 11/2011 | Greenhalgh et al. |
| 2011/0301711 A1 | 12/2011 | Palmatier et al. |
| 2011/0319997 A1 | 12/2011 | Glerum et al. |
| 2012/0010717 A1 | 1/2012 | Spann |
| 2012/0016418 A1 | 1/2012 | Chin et al. |
| 2012/0022652 A1 | 1/2012 | Berger et al. |
| 2012/0046748 A1 | 2/2012 | Weiman |
| 2012/0059472 A1 | 3/2012 | Weiman |
| 2012/0059474 A1 | 3/2012 | Weiman |
| 2012/0059475 A1 | 3/2012 | Weiman |
| 2012/0071978 A1 | 3/2012 | Suedkamp et al. |
| 2012/0109203 A1 | 5/2012 | Dryer et al. |
| 2012/0185049 A1 | 7/2012 | Varela |
| 2012/0221051 A1 | 8/2012 | Robinson |
| 2012/0226357 A1 | 9/2012 | Varela |
| 2012/0330422 A1 | 12/2012 | Weiman |
| 2013/0023993 A1 | 1/2013 | Weiman |
| 2013/0023994 A1 | 1/2013 | Glerum |

(56) References Cited

U.S. PATENT DOCUMENTS

| | | |
|---|---|---|
| 2013/0085572 A1 | 4/2013 | Glerum et al. |
| 2013/0103156 A1 | 4/2013 | Packer et al. |
| 2013/0116793 A1 | 5/2013 | Kloss |
| 2013/0144391 A1 | 6/2013 | Siegal et al. |
| 2013/0158663 A1 | 6/2013 | Miller et al. |
| 2013/0158664 A1 | 6/2013 | Palmatier et al. |
| 2013/0158668 A1 | 6/2013 | Nichols et al. |
| 2013/0158669 A1 | 6/2013 | Sungarian et al. |
| 2013/0197647 A1 | 8/2013 | Wolters et al. |
| 2013/0211526 A1 | 8/2013 | Alheidt et al. |
| 2014/0067071 A1 | 3/2014 | Weiman et al. |
| 2014/0148904 A1 | 5/2014 | Robinson |
| 2014/0163683 A1 | 6/2014 | Seifert et al. |
| 2014/0188224 A1 | 7/2014 | Dmuschewsky |
| 2014/0236296 A1 | 8/2014 | Wagner et al. |
| 2014/0249629 A1 | 9/2014 | Moskowitz et al. |
| 2014/0277461 A1 | 9/2014 | Nebosky et al. |
| 2014/0277473 A1 | 9/2014 | Perrow |
| 2014/0277500 A1 | 9/2014 | Logan et al. |
| 2014/0288653 A1 | 9/2014 | Chen |
| 2014/0343678 A1 | 11/2014 | Suddaby et al. |
| 2015/0012097 A1 | 1/2015 | Ibarra et al. |
| 2015/0066145 A1 | 3/2015 | Rogers et al. |
| 2015/0100128 A1 | 4/2015 | Glerum et al. |
| 2015/0100130 A1* | 4/2015 | Perrow .............. A61F 2/4455 623/17.16 |
| 2015/0112438 A1 | 4/2015 | McLean |
| 2015/0173917 A1 | 6/2015 | Radcliffe et al. |
| 2015/0230931 A1 | 8/2015 | Greenhalgh |
| 2015/0351928 A1 | 12/2015 | Butler et al. |
| 2015/0374507 A1 | 12/2015 | Wolters et al. |
| 2016/0051377 A1* | 2/2016 | Weiman .............. A61F 2/447 623/17.16 |
| 2016/0089247 A1 | 3/2016 | Nichols et al. |
| 2016/0113776 A1 | 4/2016 | Capote |
| 2016/0120660 A1 | 5/2016 | Melkent et al. |
| 2016/0242927 A1 | 8/2016 | Seifert et al. |
| 2016/0310291 A1 | 10/2016 | Greenhalgh |
| 2016/0361177 A1 | 12/2016 | Biedermann et al. |
| 2016/0367377 A1 | 12/2016 | Faulhaber |
| 2017/0014244 A1 | 1/2017 | Seifert et al. |
| 2017/0056197 A1 | 3/2017 | Weiman et al. |
| 2017/0172756 A1 | 6/2017 | Faulhaber |
| 2017/0216036 A1 | 8/2017 | Cordaro |
| 2017/0224504 A1 | 8/2017 | Butler et al. |
| 2017/0224505 A1 | 8/2017 | Butler et al. |
| 2017/0246006 A1 | 8/2017 | Carnes et al. |
| 2017/0258605 A1 | 9/2017 | Blain et al. |
| 2017/0281432 A1 | 10/2017 | Glerum et al. |
| 2017/0296352 A1 | 10/2017 | Richerme et al. |
| 2017/0333198 A1 | 11/2017 | Robinson |
| 2017/0333199 A1 | 11/2017 | Sharifi-Mehr et al. |
| 2017/0333200 A1 | 11/2017 | Arnin |
| 2017/0348116 A1 | 12/2017 | Weiman |
| 2017/0367842 A1 | 12/2017 | Predick et al. |
| 2018/0014947 A1 | 1/2018 | Baynham |
| 2018/0042732 A1 | 2/2018 | Seifert et al. |
| 2018/0055652 A1 | 3/2018 | Davenport et al. |
| 2018/0185163 A1 | 7/2018 | Weiman et al. |
| 2018/0243107 A1 | 8/2018 | Foley et al. |
| 2018/0256359 A1 | 9/2018 | Greenhalgh |
| 2018/0303621 A1 | 10/2018 | Brotman et al. |
| 2018/0318101 A1 | 11/2018 | Engstrom |
| 2018/0325693 A1 | 11/2018 | Weiman et al. |
| 2018/0360616 A1 | 12/2018 | Luu |
| 2019/0021871 A1 | 1/2019 | Baynham |
| 2019/0133779 A1 | 5/2019 | McLaughlin et al. |
| 2019/0133784 A1 | 5/2019 | Gunn et al. |
| 2019/0201210 A1 | 7/2019 | Besaw et al. |
| 2019/0254836 A1 | 8/2019 | Cowan et al. |
| 2019/0254838 A1 | 8/2019 | Miller et al. |
| 2019/0298524 A1 | 10/2019 | Lauf et al. |
| 2019/0307577 A1 | 10/2019 | Predick et al. |
| 2019/0314168 A1 | 10/2019 | Faulhaber |
| 2019/0328540 A1 | 10/2019 | Seifert et al. |
| 2019/0374348 A1 | 12/2019 | Butler et al. |
| 2019/0388232 A1 | 12/2019 | Purcell et al. |
| 2019/0388238 A1 | 12/2019 | Lechmann et al. |
| 2020/0054461 A1 | 2/2020 | Marrocco et al. |
| 2020/0129307 A1 | 4/2020 | Hunziker et al. |
| 2020/0360153 A1 | 11/2020 | Weiman et al. |
| 2021/0015627 A1 | 1/2021 | Weiman et al. |
| 2021/0045891 A1 | 2/2021 | Rogers et al. |
| 2021/0045892 A1 | 2/2021 | Rogers et al. |
| 2021/0113349 A1 | 4/2021 | Weiman et al. |
| 2021/0137699 A1 | 5/2021 | Jang et al. |
| 2021/0259849 A1 | 8/2021 | Robinson et al. |
| 2021/0322181 A1 | 10/2021 | Predick |
| 2022/0133495 A1 | 5/2022 | Glerum et al. |
| 2022/0304823 A1 | 9/2022 | Melchor |
| 2022/0387184 A1 | 12/2022 | Josse et al. |

FOREIGN PATENT DOCUMENTS

| | | |
|---|---|---|
| DE | 94 07 806 U1 | 7/1994 |
| DE | 10 2020 200 882 A1 | 7/2020 |
| EP | 0 880 950 A1 | 12/1998 |
| EP | 1 925 272 A1 | 5/2008 |
| EP | 2 777 633 A2 | 9/2014 |
| EP | 3 031 424 A1 | 6/2016 |
| EP | 3 245 982 | 11/2017 |
| EP | 3 479 799 A1 | 5/2019 |
| EP | 3 769 725 A1 | 1/2021 |
| FR | 2717068 A1 | 4/1996 |
| FR | 2727003 B1 | 4/1997 |
| FR | 2894130 A1 | 6/2007 |
| GB | 0 284 462 A | 2/1928 |
| KR | 200290058 Y1 | 9/2002 |
| KR | 100905962 B1 | 7/2009 |
| WO | WO-95/31158 A1 | 11/1995 |
| WO | WO-99/26562 A1 | 6/1999 |
| WO | WO-2004/052245 | 6/2004 |
| WO | WO-2006/102485 | 9/2006 |
| WO | WO-2006/105437 A2 | 10/2006 |
| WO | WO-2009/124269 | 10/2009 |
| WO | WO-2010/148112 | 12/2010 |
| WO | WO-2012/121726 A1 | 9/2012 |
| WO | WO-2014/134590 A1 | 9/2014 |
| WO | WO-2014/165319 A1 | 10/2014 |
| WO | WO-2015/009793 A1 | 1/2015 |
| WO | WO-2015/063721 A1 | 5/2015 |
| WO | WO-2015/085111 A1 | 6/2015 |
| WO | WO-2016/051095 A1 | 4/2016 |
| WO | WO-2016/077610 A1 | 5/2016 |
| WO | WO2016/127139 A1 | 8/2016 |
| WO | WO-2017/027277 A1 | 2/2017 |
| WO | WO-2017/027873 A1 | 2/2017 |
| WO | WO-2017/066463 A1 | 4/2017 |
| WO | WO-2017/106614 A1 | 6/2017 |
| WO | WO-2018/049227 A1 | 3/2018 |
| WO | WO-2018/200507 A1 | 11/2018 |
| WO | WO-2018/200530 A1 | 11/2018 |
| WO | WO2019/014139 A1 | 1/2019 |
| WO | WO-2019/126213 A1 | 6/2019 |
| WO | WO-2019/241687 A1 | 12/2019 |
| WO | WO-2021/030645 A1 | 2/2021 |

OTHER PUBLICATIONS

Schizas, C., "Spinal Fusion: Techniques Results and Limitations." European Cells and Materials. 2005, vol. 10, Suppl. 3, p. 1.
International Search Report and Written Opinion in PCT PCT/US2021/030261 dated Aug. 31, 2021 (18 pages).
International Search Report and Written Opinion in PCT/US2021/031596 dated Sep. 28, 2021 (12 pages).
International Search Report and Written Opinion in PCT/US2021/033832 dated Sep. 17, 2021.
International Search Report and Written Opinion received for Life Spine, Inc. for PCT app. PCT/US2021/026606 dated Jul. 15, 2021, 20 pages.
International Search Report and Written Opinion received for Life Spine, Inc., for PCT app. No. PCT/US2021026610 dated Jul. 20, 2021, 18 pages.

(56) References Cited

OTHER PUBLICATIONS

Bacfuse® Spinous Process Fusion Plate Surgical Technique, 2011, Pioneer Surgical, 12 pages.

Extended European Search Report for European Application No. 14159101.6, dated Jun. 18, 2014, 6 pages.

Extended European Search Report for European Application No. 16169890.7, dated Oct. 21, 2016, 7 pages.

International Preliminary Report on Patentability for Application No. PCT/US06/12060 dated Sep. 30, 2007, 3 pages.

International Search Report and Written Opinion for International Application No. PCT/US2012/057324, dated Dec. 20, 2012, 10 pages.

International Search Report for International Application No. PCT/US2018/029120, dated Jun. 28, 2018, 17 pages.

International Search Report for International Application No. PCT/US2018/029149, dated Jun. 25, 2018, 13 pages.

Written Opinion of the International Searching Authority for Application No. PCT/US06/12060, dated Apr. 5, 2007, 3 pages.

International Search Report for International Application No. PCT/US2019/037275, dated Sep. 24, 2019, 12 pages.

International Search Report on PCT/US2020/037020, dated Sep. 29, 2020, 20 pages.

Search Report for International Application No. PCT/US2018/041306, dated Sep. 28, 2018, 12 pages.

International Search Report and Written Opinion on PCT/US2020/036809 dated Sep. 14, 2020, 12 pages.

"MectaLIF Oblique & Posterior Intervertebral Body Fusion Device." Brochure. 2004, Medacta International, San Pietro, Switzerland.

"Webster's II New College Dictionary." Excerpts. 2005, Houghton Mifflin Co., p. 992.

"Wedge." Encyclopedia Brittanica. Aug. 14, 2008. britannica.com/print/article/638734. 2 pages.

International Search Report and Written Opinion in PCT/US2022/053230 dated May 3, 2023 (18 pages).

Kambin, P., et al., "Arthroscopic Discectomy of the Lumbar Spine." Clinical Orthopaedics and Related Research. Apr. 1997, No. 337, pp. 49-57.

Kim, D., et al. "Posterior Lumbar Interbody Fusion Using a Unilateral Single Cage and a Local Morselized Bone Graft in the Degenerative Lumbar Spine." Clinics in Orthopedic Surgery. 2009, vol. 1, No. 4, pp. 214-221.

Kim, Y., et al., "Clinical Applications of the Tubular Retractor on Spinal Disorders." Journal of Korean Neurosurgery, Nov. 2007, No. 42, pp. 244-250.

Moore, J., et al., "Mechanics Map—Wedges." Aug. 20, 2022, mechanicsmap.psu.edu/websites/7_friction/7-3_wedges/wedges.

Peltier, L. "Orthopedics: A History and Iconography" 1993, Norman Publishing, San Francisco, CA.

Sasso, R., et al., "Anterior Lumbar Interbody Fusion." Surgical Management of Low Back Pain. 2009, Chapter 10, pp. 87-95.

Tsuang, Y., et al., "Comparison of cage application modality in posterior lumbar interbody fusion with posterior instrumentation-A finite element study." Medical Engineering & Physics 31. 2009, pp. 565-570.

Virk, S., et al. "History of Spinal Fusion: Where We Came from and Where We Are Going." Current Concepts in Spinal Fusion. HSS Journal, 2020, No. 16, pp. 137-142.

Xiao, Y, et al., "Unilateral Transforaminal Lumbar Interbody Fusion: a Review of the Technique, Indications and Graft Materials." The Journal of International Medical Research. 2009, No. 37, pp. 908-917.

International Search Report and Written Opinion in PCT/US2023/021528 dated Aug. 24, 2023 (17 pages).

\* cited by examiner

EXPANDABLE IMPLANT ASSEMBLY

CROSS-REFERENCE TO RELATED PATENT APPLICATIONS

This application is a continuation in part of International Application No. PCT/US2018/041306, filed Jul. 9, 2018, which is a continuation-in-part of U.S. application Ser. No. 15/645,179 (now U.S. Pat. No. 10,154,911), filed Jul. 10, 2017 both of which are incorporated herein by reference in their entireties.

BACKGROUND

The present disclosure relates to expandable implants and devices, including spinal interbody and intravertebral body devices, and vertebral interbody and intravertebral devices that are expandable after spinal placement thereof.

Fusion cages, as well as other types of implants, bodies and/or devices, are frequently utilized in spinal surgery inside a vertebra (intravertebral) and/or between vertebrae of a patient (interbody), or adjacent other bone bodies. With interbody devices, one or more such spinal bodies are placed between vertebrae to provide support and promote fusion between adjacent vertebrae where such is necessary due to disease, injury, general deterioration or congenital problem. With intravertebral devices, one or more spinal bodies are placed within a vertebra. Spinal devices, such as fusion cages and/or the like, are inserted into a spinal space either anteriorly, posteriorly, laterally or posteriolaterally.

Some spinal interbody and intravertebral devices may be static in size. Static sized spinal devices may be fairly large in order to properly bridge the gap between adjacent vertebrae. This large size may not lend itself to microsurgery, arthroscopic surgery or the like.

Expandable interbody devices allow the device to be initially smaller than traditional non-expandable (static) interbody devices such that expandable interbody devices may be more easily inserted or implanted into the vertebral space. Moreover, expandable devices allow the surgeon to set the amount of expansion necessary for the particular patient rather than the static device dictating the spacing.

SUMMARY

One embodiment of the present disclosure is an expandable implant. The expandable implant includes an upper main support, a lower main support, an upper pivoting support, and a lower pivoting support. The upper main support is configured to engage a first portion of bone. The lower main support is coupled to the upper main support and configured to engage a second portion of bone. The upper main support is adjustable relative to the lower main support to adjust a height of the expandable implant. The upper pivoting support is configured to engage the first portion of bone. The upper pivoting support is rotatably movable relative to the upper main support. The lower pivoting support is coupled to the upper pivoting support and configured to engage the second portion of bone. Adjustment of the upper main support relative to the lower main support causes a corresponding adjustment of the upper pivoting support relative to the lower pivoting support. The lower pivoting support is rotatably movable relative to the lower main support.

Another embodiment of the present disclosure is an expandable implant. The expandable implant includes an upper support assembly, and a lower support assembly. The upper support assembly is configured to engage a first portion of bone and includes an upper main support and an upper pivoting support. The upper pivoting support is rotatably movable relative to the upper main support. The lower support assembly is coupled to the upper support assembly and is configured to engage a second portion of bone. The lower support assembly includes a lower main support and a lower pivoting support. The lower pivoting support is rotatably movable relative to the lower main support. The upper support assembly is adjustable relative to the lower support assembly to adjust a height of the expandable implant.

Another embodiment of the present disclosure is a method of using an expandable implant. The expandable implant includes an upper main support, a lower main support, an upper pivoting support, and a lower pivoting support. The method includes positioning an expandable implant in a desired position, rotating the upper and lower pivoting supports about the upper and lower main supports, and translating the upper main support and the upper pivoting support relative to the lower main support and the lower pivoting support.

BRIEF DESCRIPTION

The foregoing and other features of the present disclosure will become more apparent to one skilled in the art upon also reading the following description of embodiments with reference to the accompanying drawings.

Figure 1:
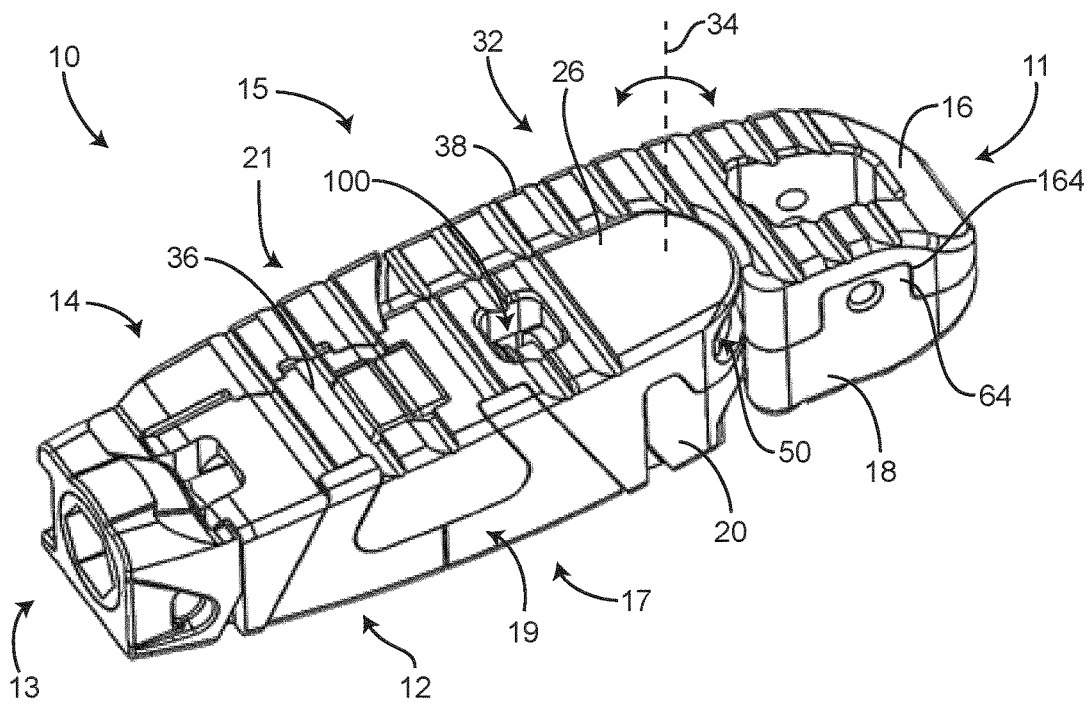
FIG. 1 is a perspective view of an implant, according to one embodiment.
Figure 8:
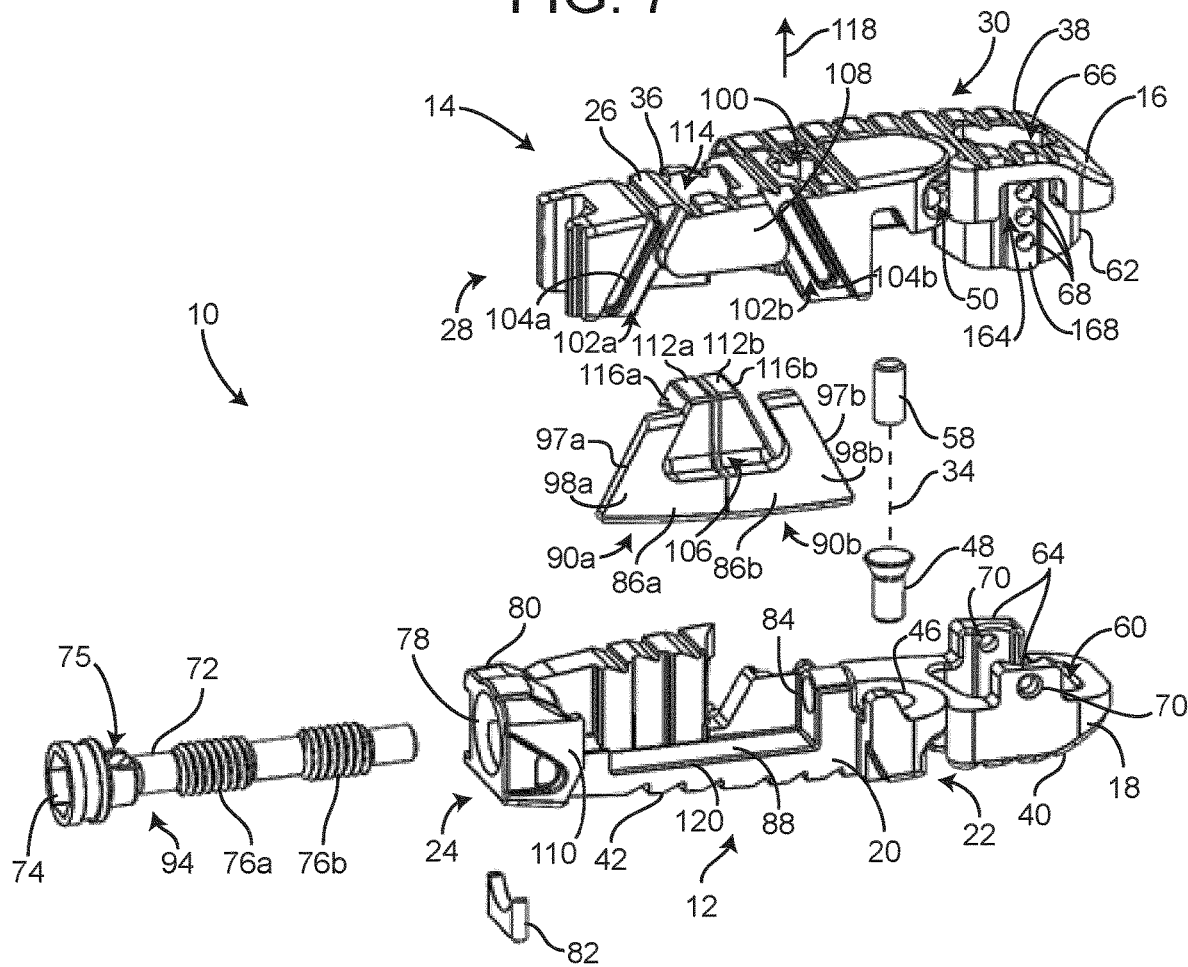

FIG. 8 in exploded perspective view of the implant of FIG. 1, according to one embodiment.

Figure 9:
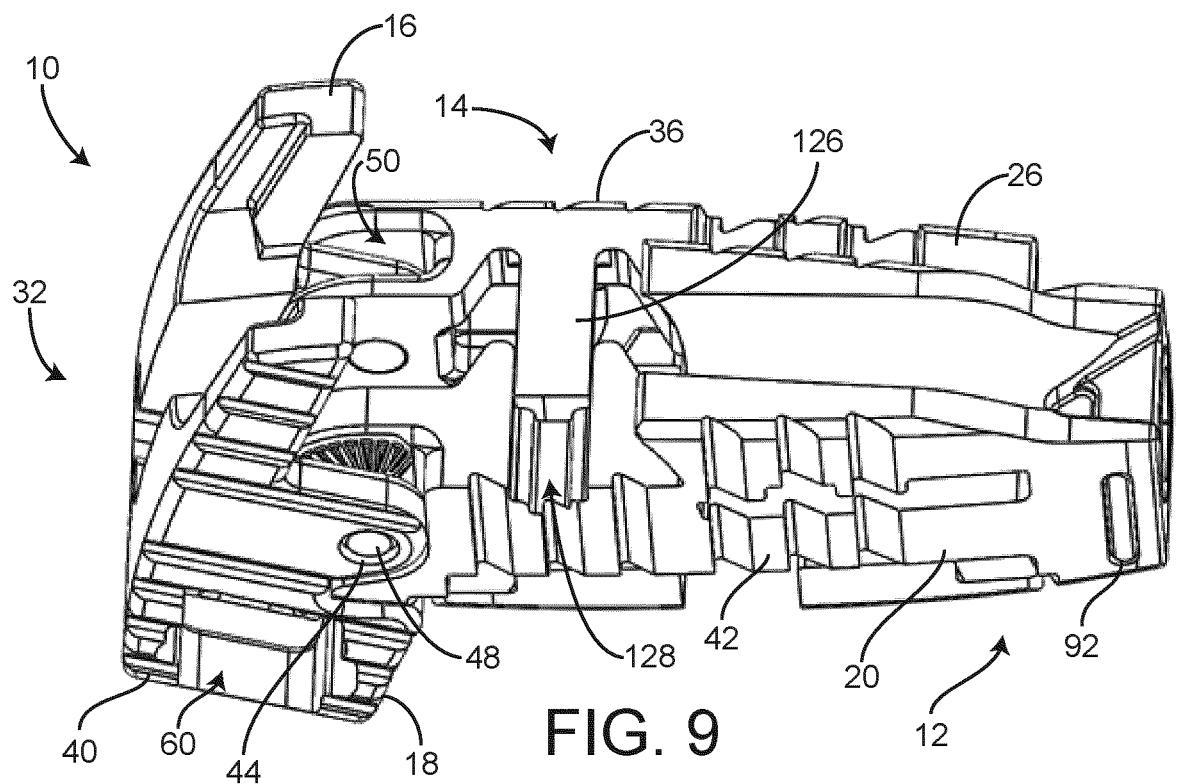

FIG. 9 is a perspective view of the implant of FIG. 1 in an expanded configuration, according to one embodiment.

Figure 10:
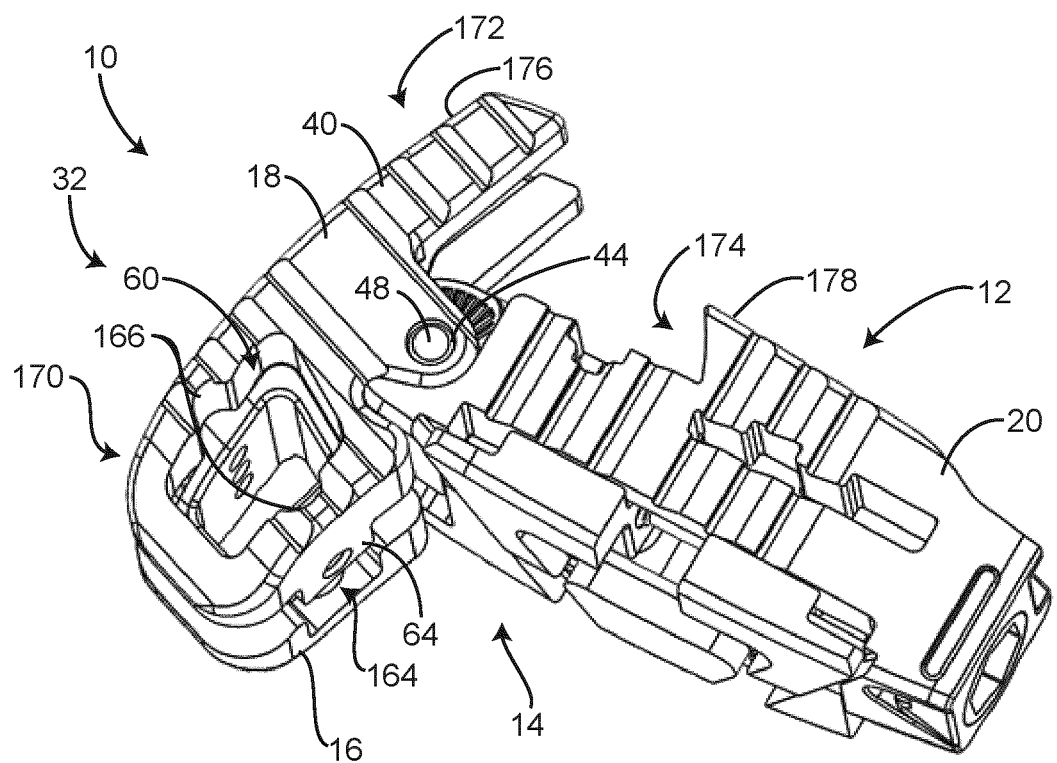

FIG. 10 is a perspective view of the implant of FIG. 1 in an expanded configuration, according to one embodiment.

Figure 11:
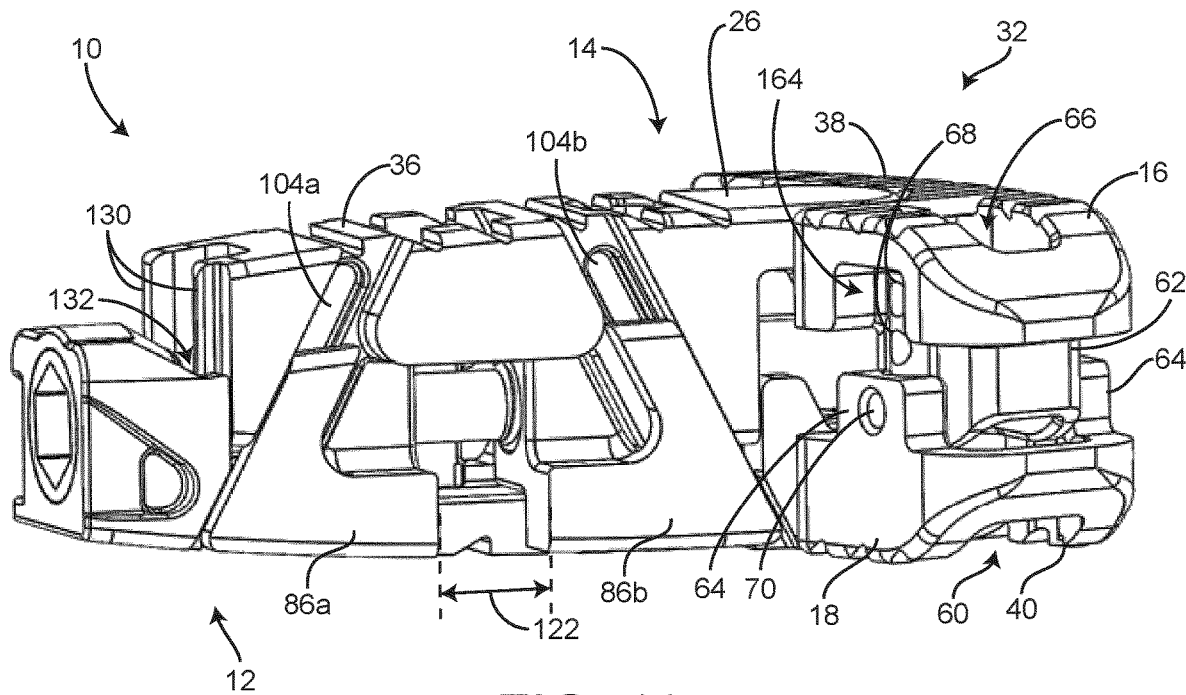

FIG. 11 is a perspective view of the implant of FIG. 1 in an expanded configuration, according to one embodiment.

Figure 12:
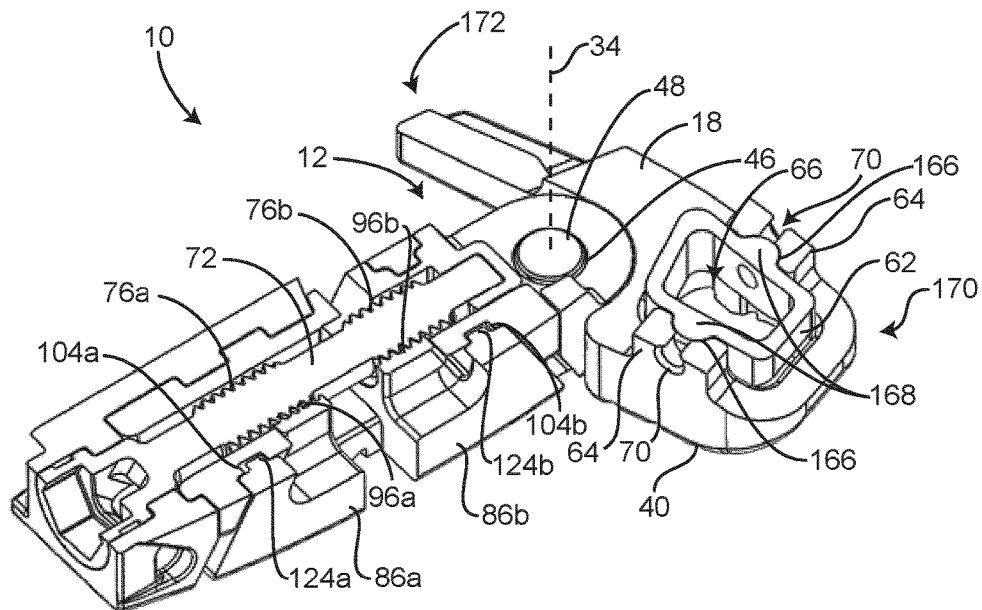
Figures 13A, 13B, 13C, 13D:
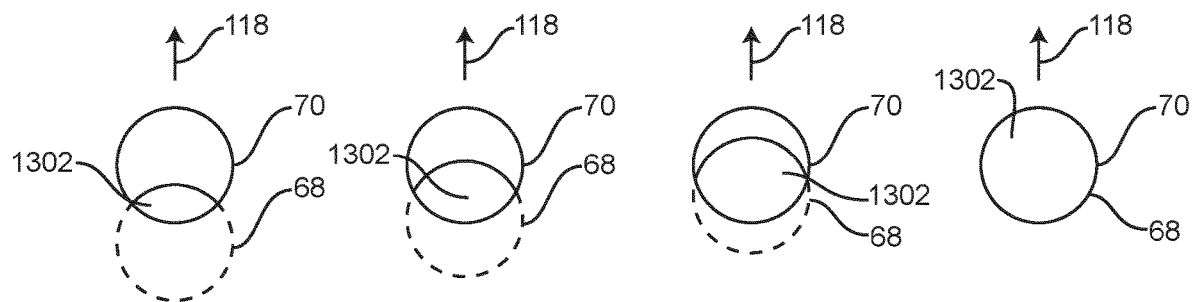

FIG. 12 is a sectional perspective view of the implant of FIG. 1, according to one embodiment.

FIGS. 13A-D are drawings of apertures of the implant of FIG. 1 in various stages of expansion, according to one embodiment.

Figure 14:
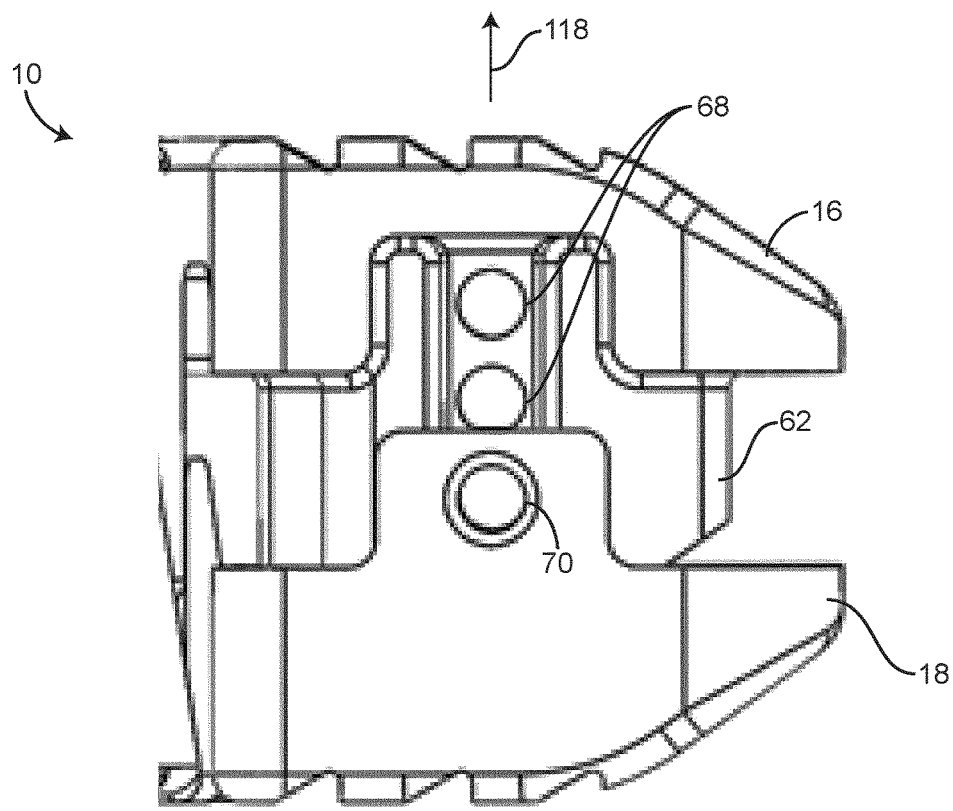

FIG. 14 is a side view of a portion of the implant of FIG. 1, according to some embodiments.

Figure 15:
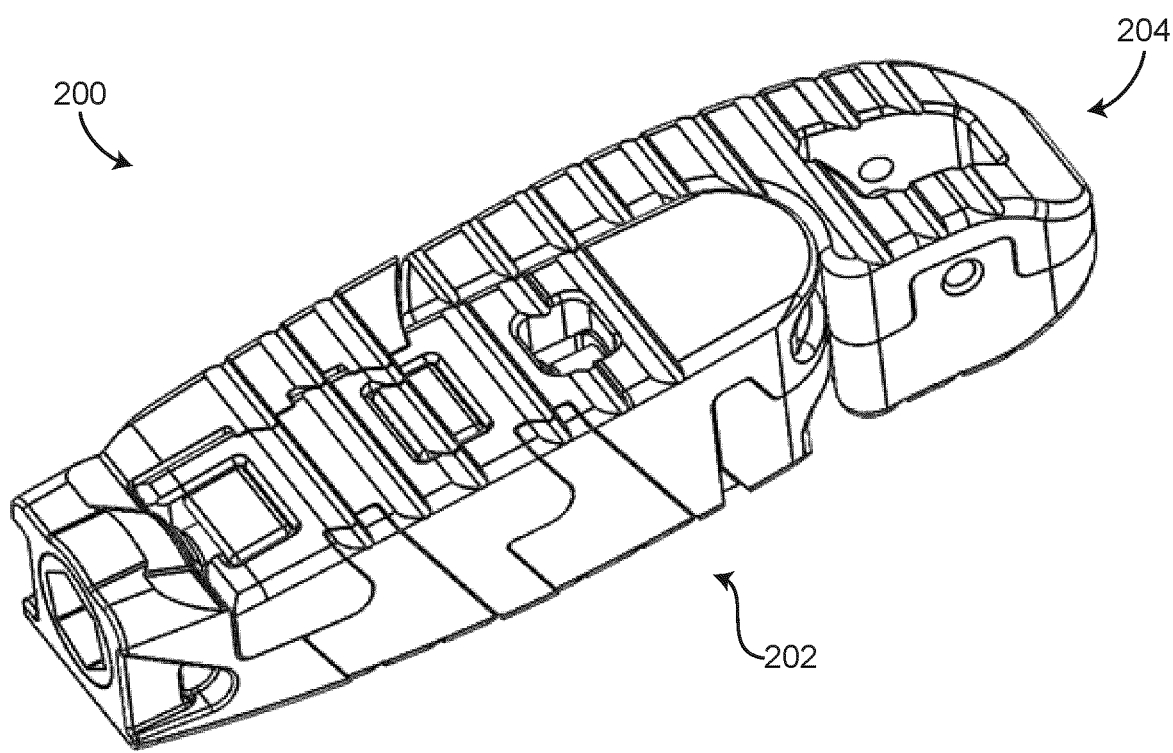

FIG. 15 is a perspective view of an implant, according to another embodiment.

Figure 16:
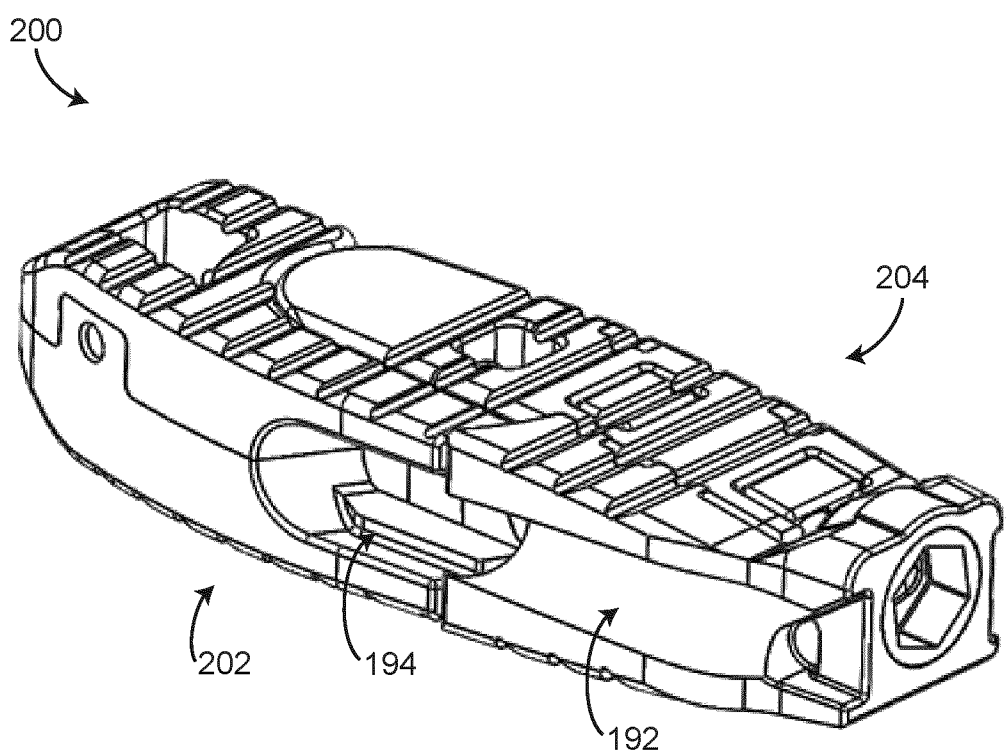

FIG. 16 is a perspective view of an implant, according to another embodiment.

Figure 17:
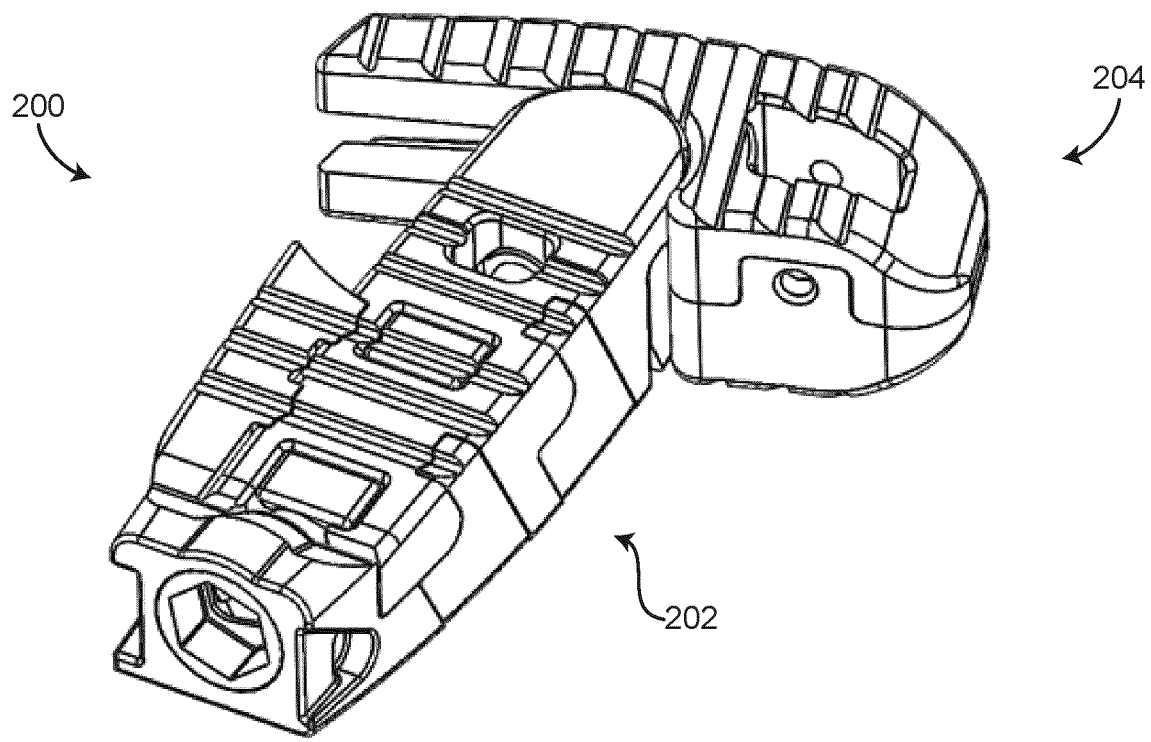

FIG. 17 is a perspective view of the implant of FIGS. 15-16 in a rotated configuration, according to one embodiment.

Figure 18:
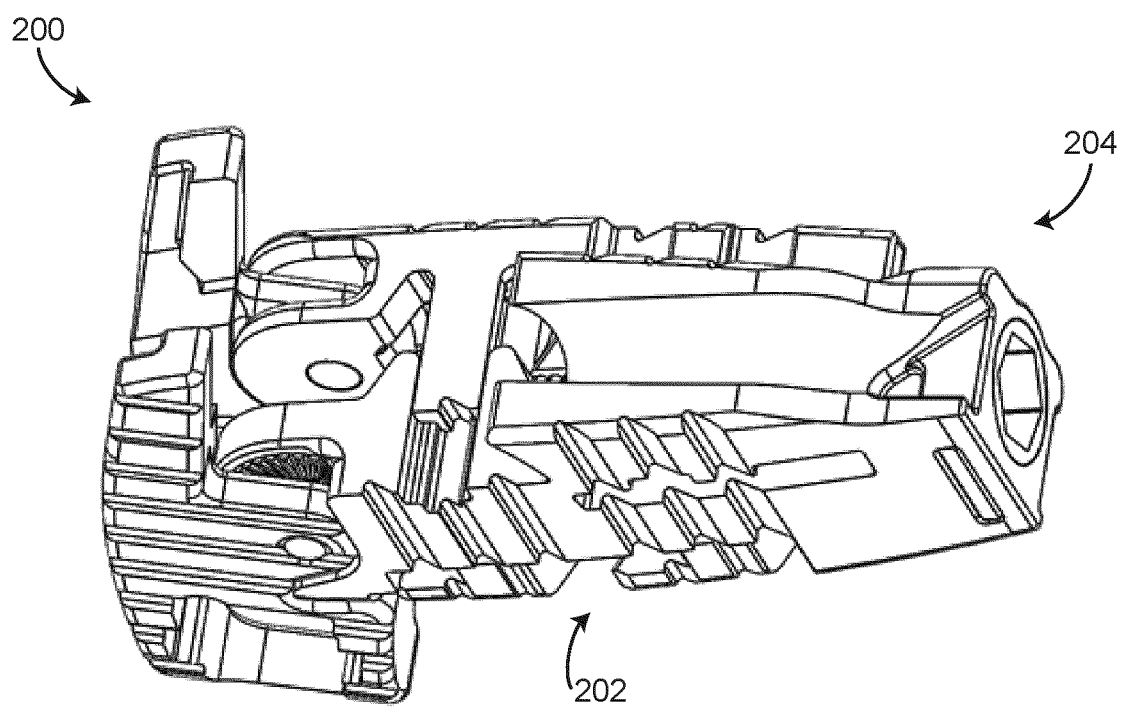

FIG. 18 is a perspective view of the implant of FIGS. 15-16 in a rotated and expanded configuration, according to one embodiment.

Figure 19:
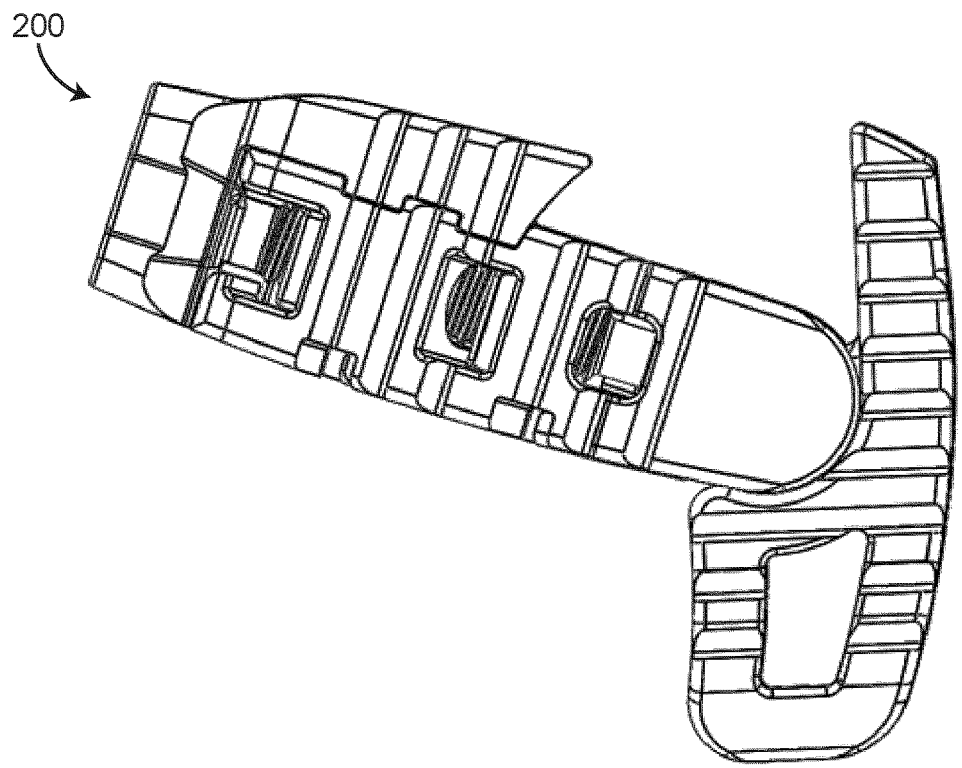

FIG. 19 is a top view of the implant of FIGS. 15-16 in the rotated configuration, according to one embodiment.

Figure 20:
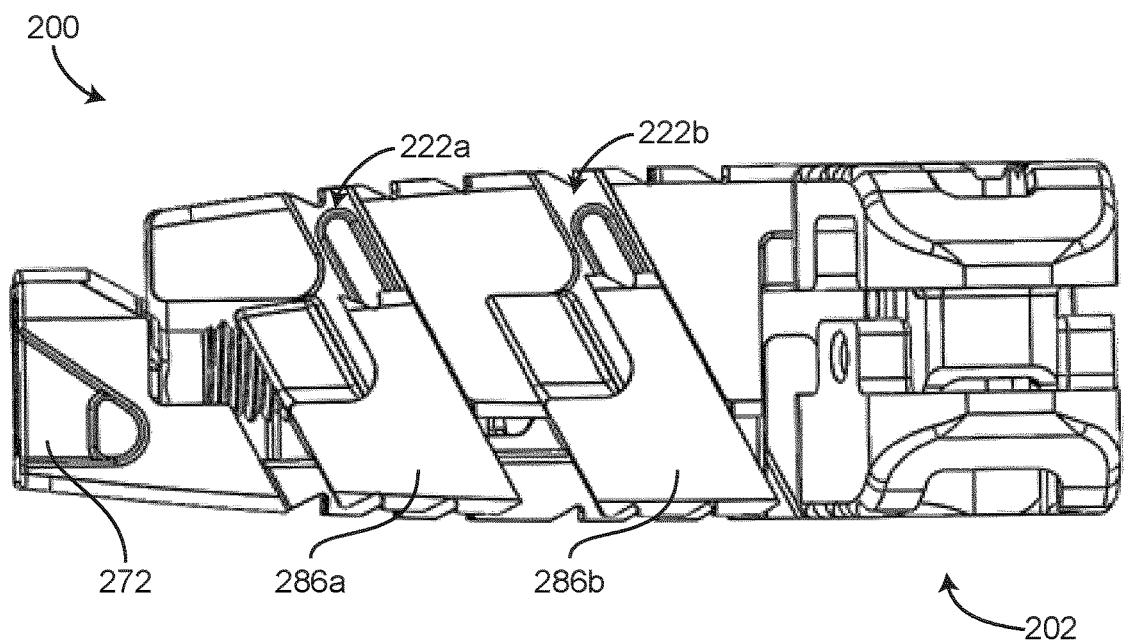

FIG. 20 is a side view of the implant of FIGS. 15-16 in a rotated and expanded configuration, according to one embodiment.

Figure 21:
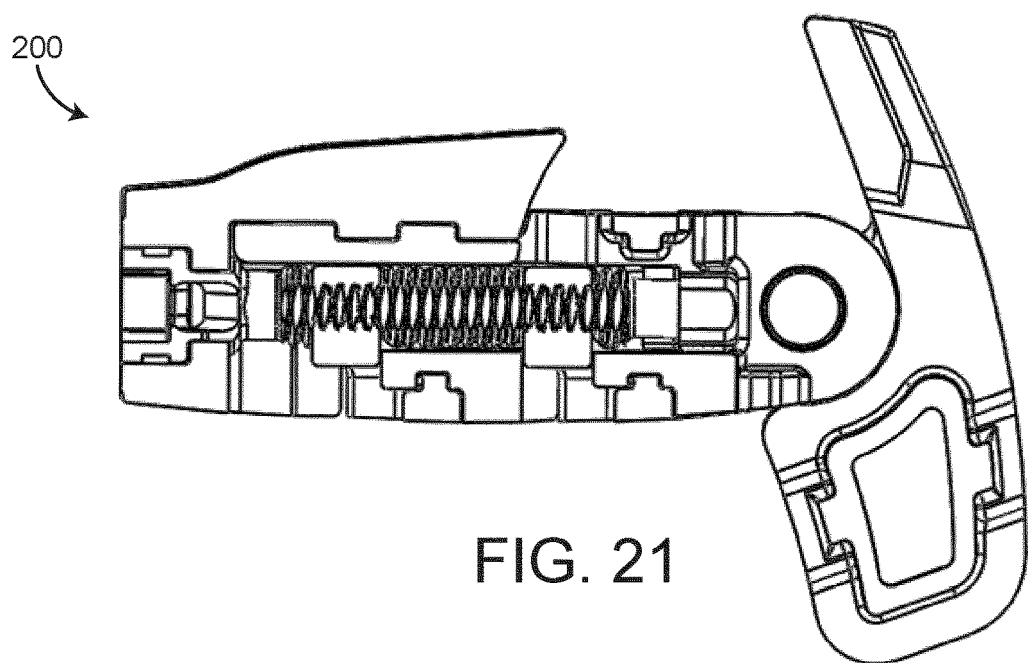

FIG. 21 is a top sectional view of the implant of FIGS. 15-16 in a rotated configuration, according to one embodiment.

Figure 22:
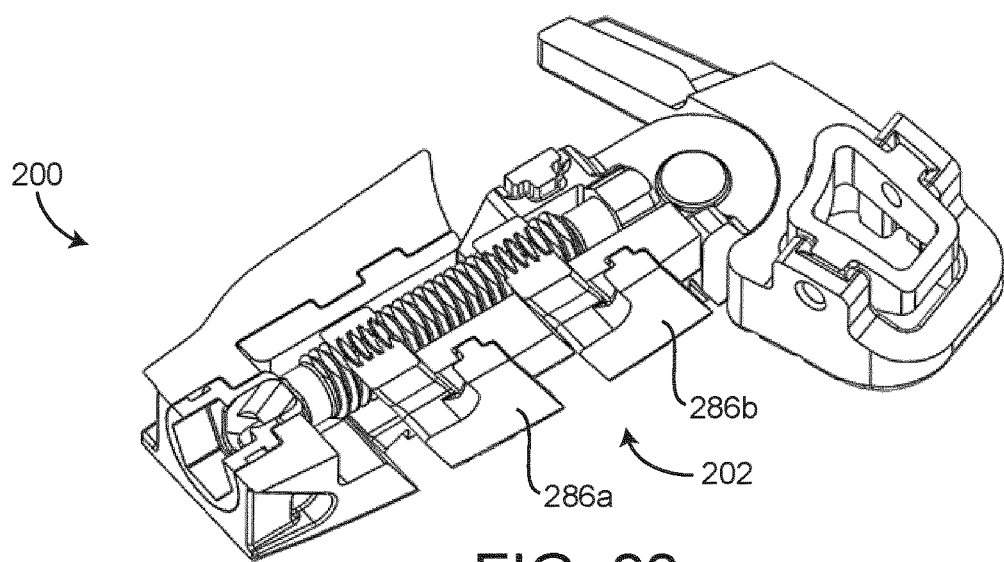

FIG. 22 is a perspective sectional view of the implant of FIGS. 15-16 in a rotated configuration, according to one embodiment.

Figure 23:
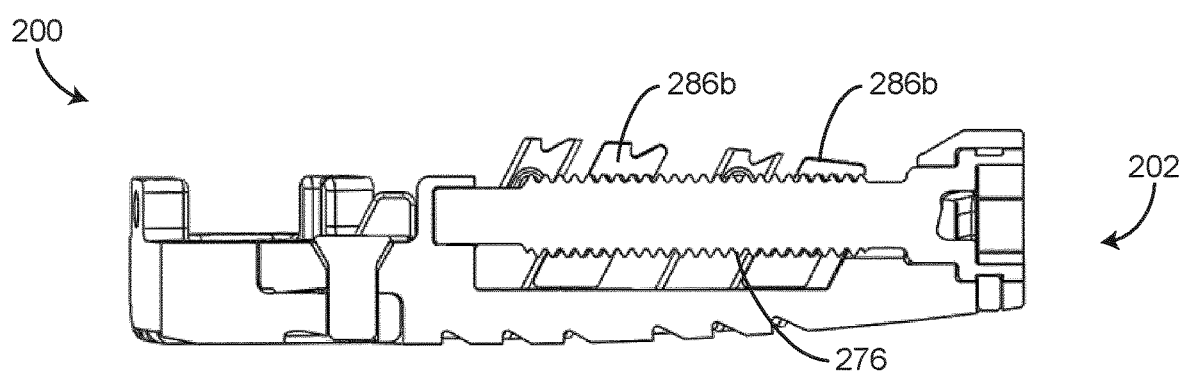

FIG. 23 is a side sectional view of the implant of FIGS. 15-16 and various members configured to expand and retract the implant, according to one embodiment.

Figure 24:
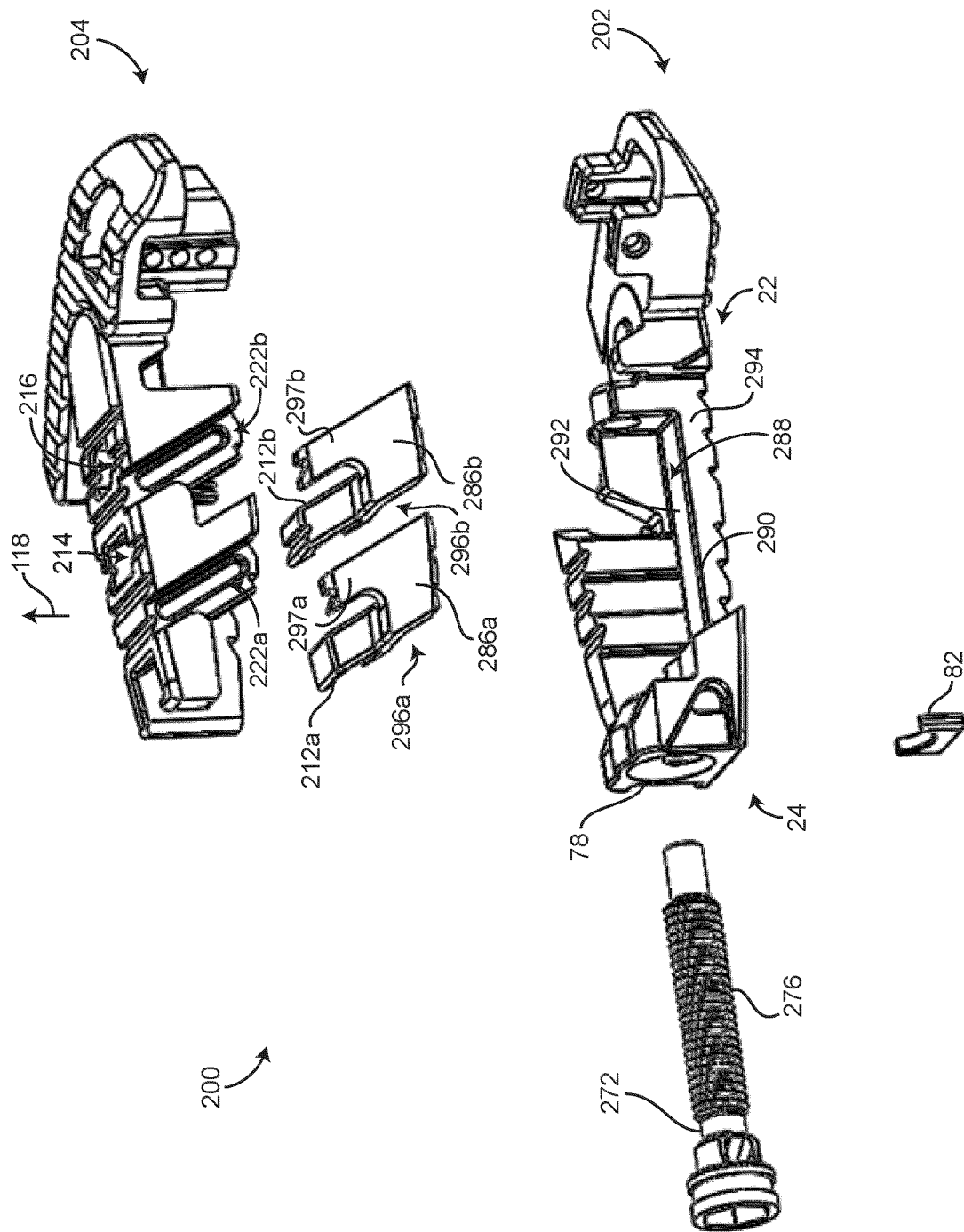

FIG. 24 is a perspective exploded view of the implant of FIGS. 15-16, according to one embodiment.

Figure 25:
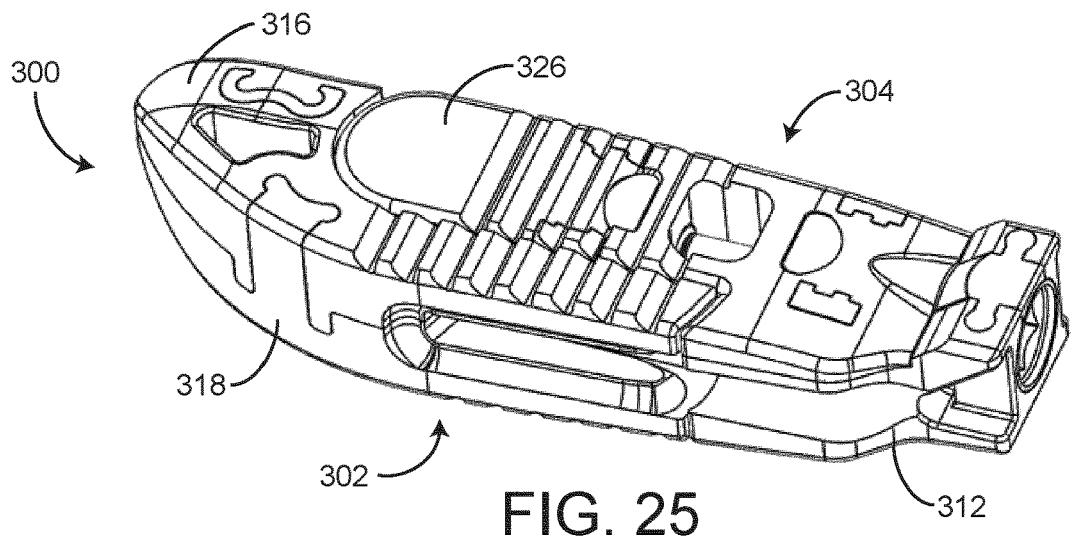

FIG. 25 is a perspective view of an implant, according to another embodiment.

Figure 26:
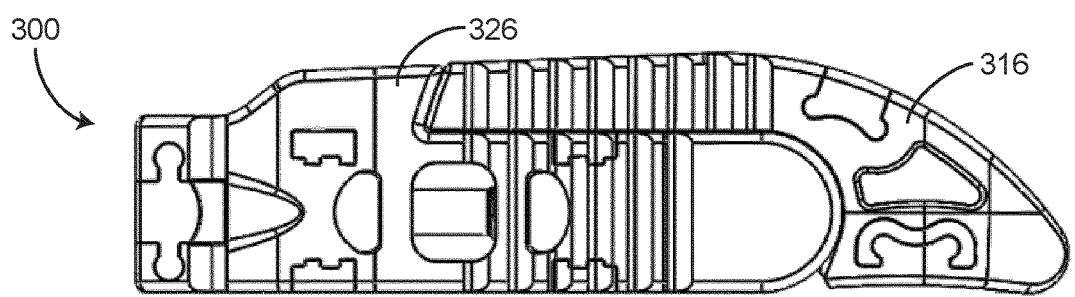

FIG. 26 is a top view of the implant of FIG. 25, according to one embodiment.

Figure 27:
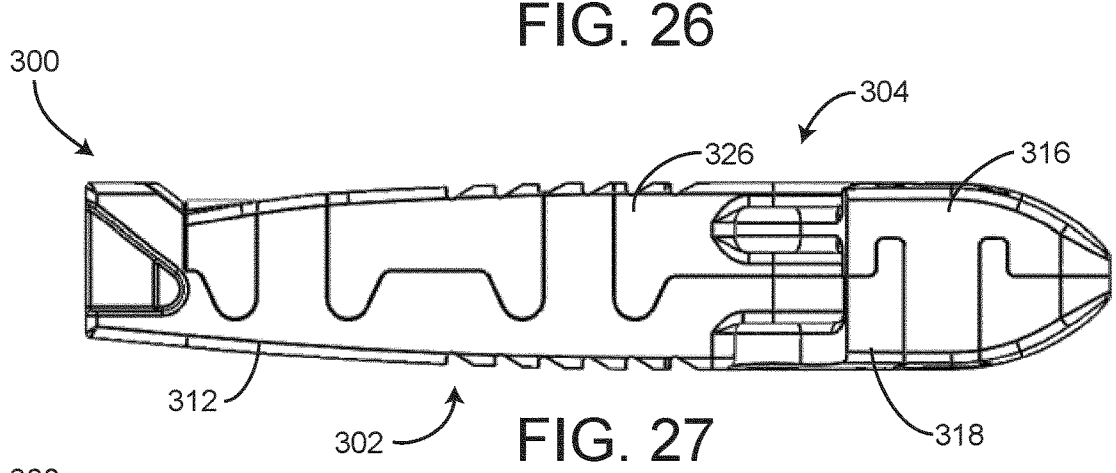

FIG. 27 is a side view of the implant of FIG. 25, according to one embodiment.

Figure 28:
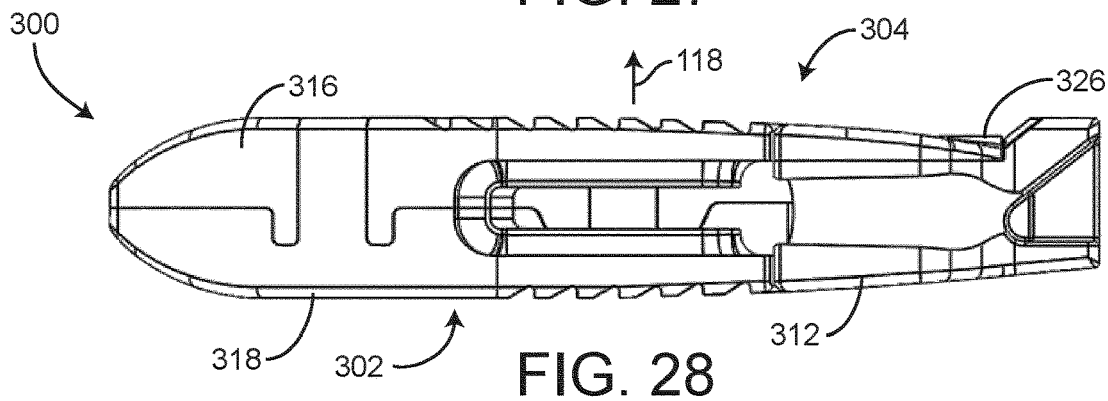

FIG. 28 is a side view of the implant of FIG. 25, according to one embodiment.

Figure 29:
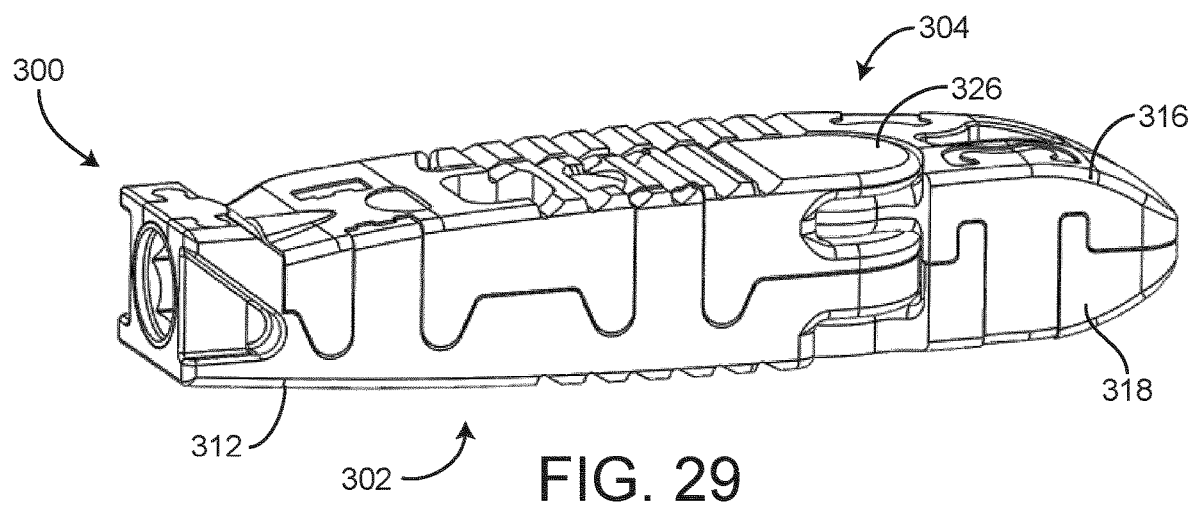

FIG. 29 is a perspective view of the implant of FIG. 25, according to one embodiment.

Figure 30:
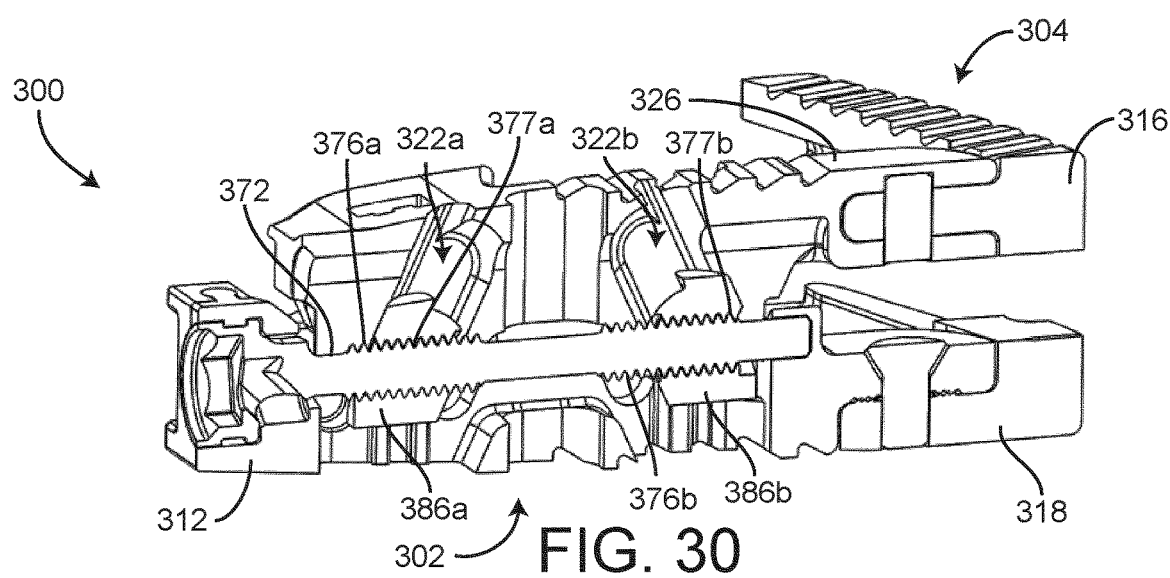

FIG. 30 is a perspective sectional view of the implant of FIG. 25 in an expanded and rotated configuration, according to one embodiment.

Figure 31:
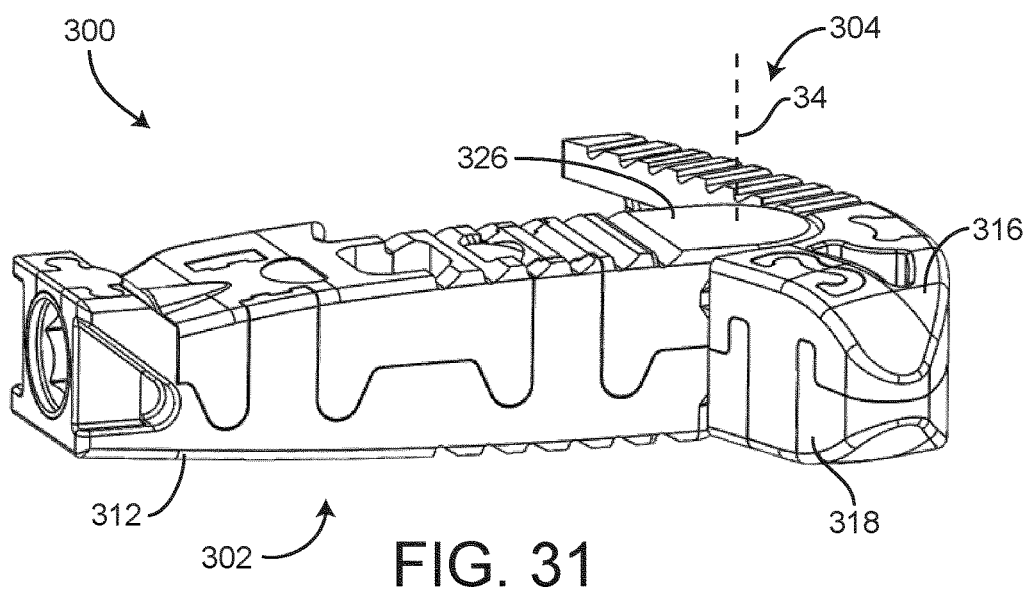

FIG. 31 is a perspective view of the implant of FIG. 25 in a rotated configuration, according to one embodiment.

Figure 32:
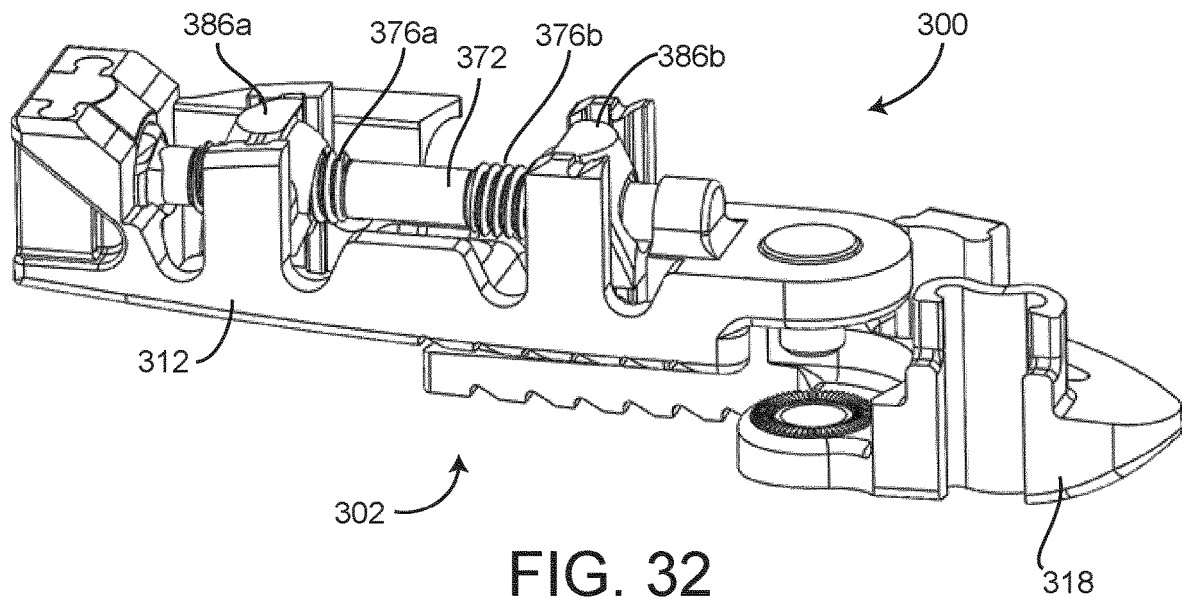

FIG. 32 is an exploded perspective view of a bottom assembly of the implant of FIG. 25, according to one embodiment.

Figure 33:
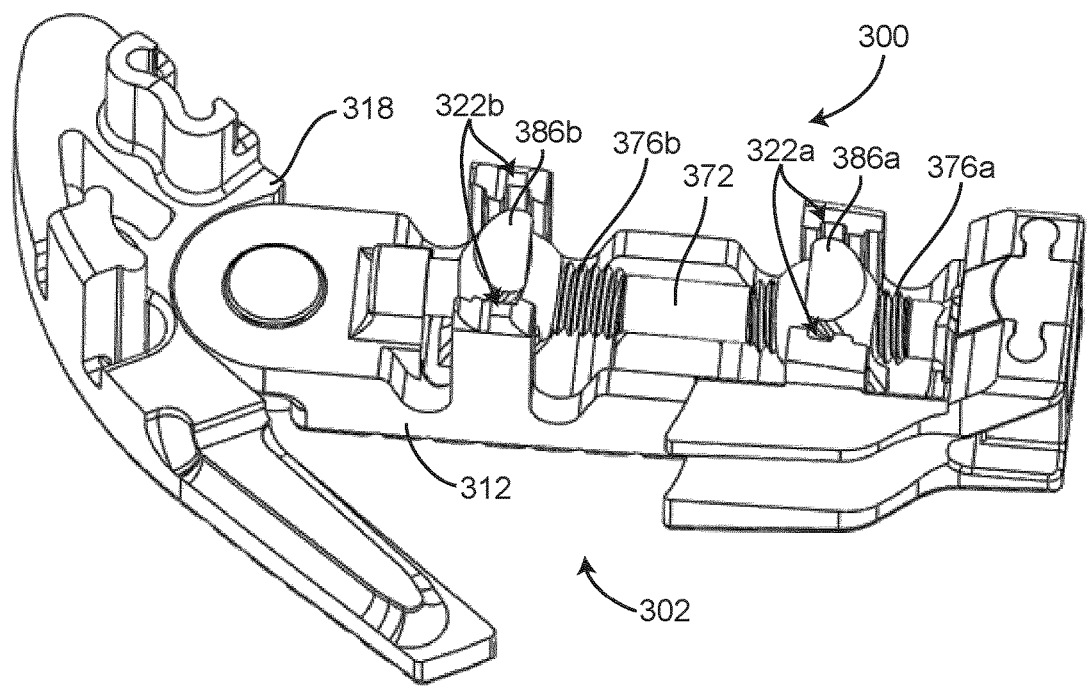

FIG. 33 is a perspective view of the bottom assembly of FIG. 32 of the implant of FIG. 25, according to one embodiment.

Figure 34:
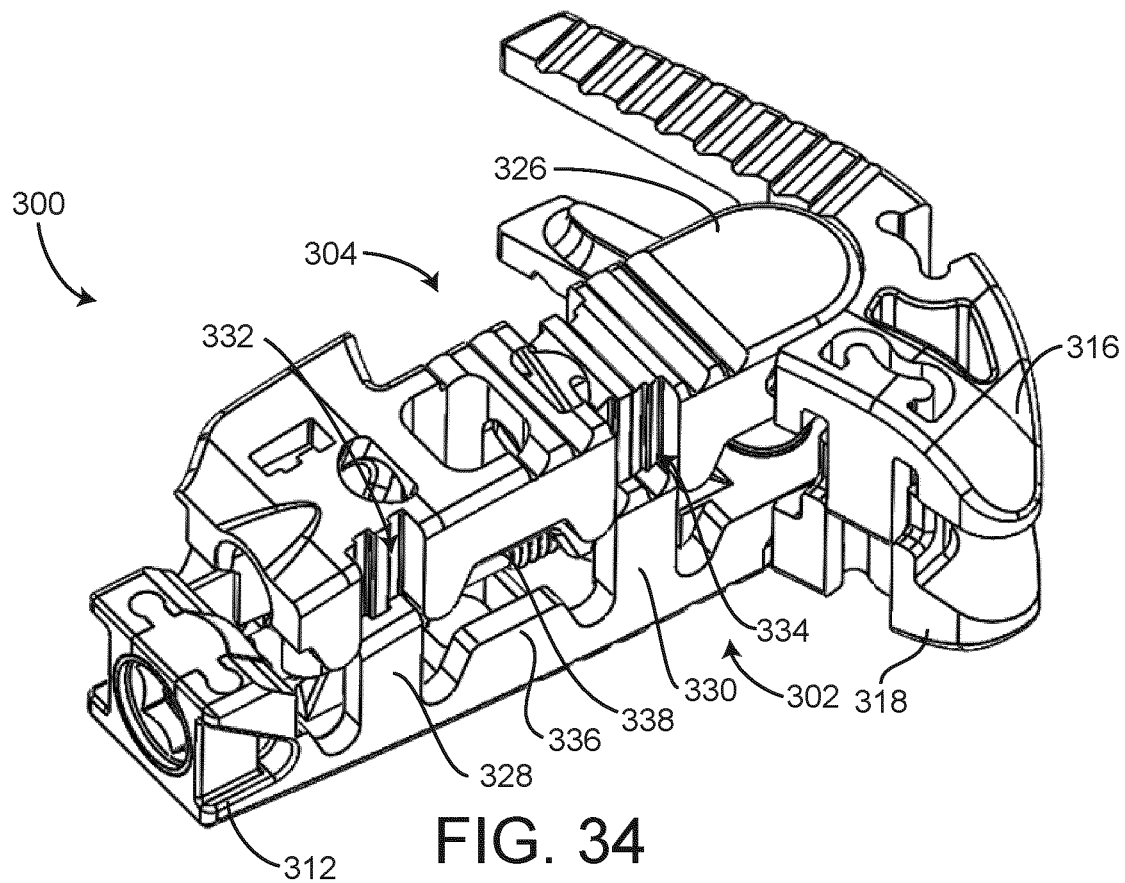

FIG. 34 is a perspective view of the implant of FIG. 25 in a rotated and expanded configuration, according to some embodiments.

Figure 35:
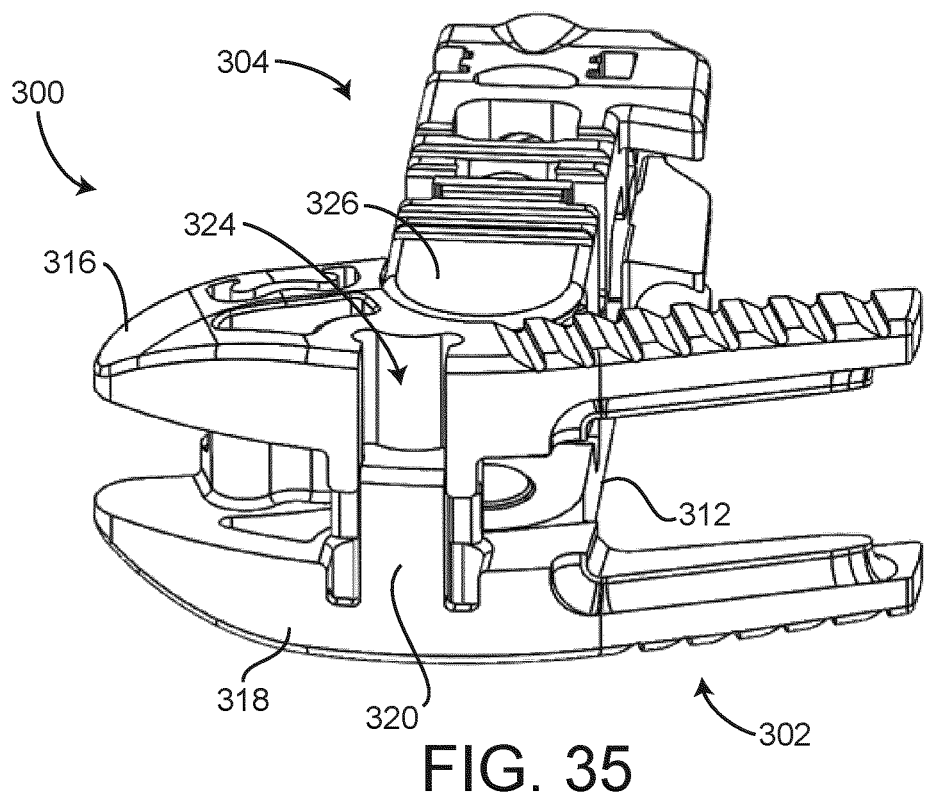

FIG. 35 is a perspective view of the implant of FIG. 25 in a rotated and expanded configuration, according to some embodiments.

Figure 36:
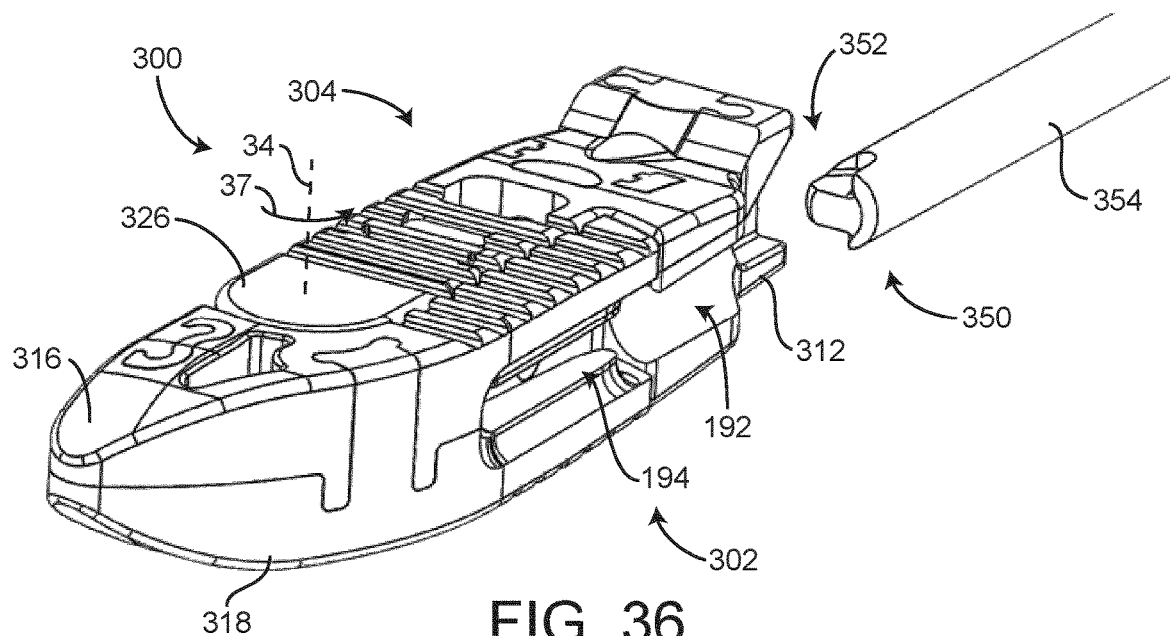

FIG. 36 is a perspective view of the implant of FIG. 25 being transitioned into a rotated configuration with a first adjustment tool, according to some embodiments.

Figure 37:
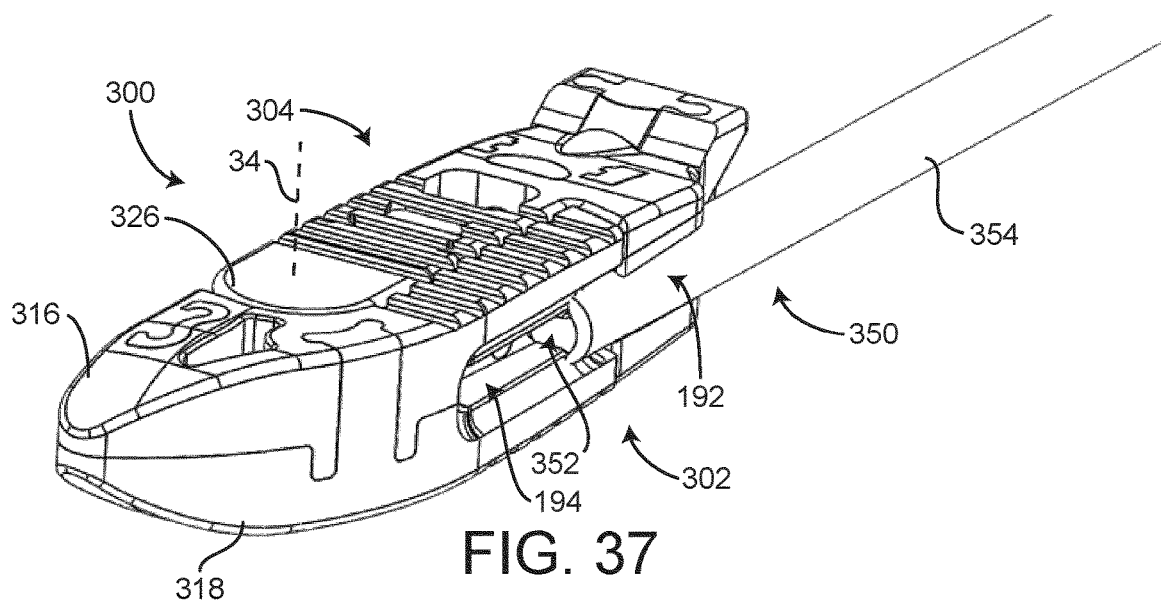

FIG. 37 is a perspective view of the implant of FIG. 25 being transitioned into a rotated configuration with a first adjustment tool, according to some embodiments.

Figure 38:
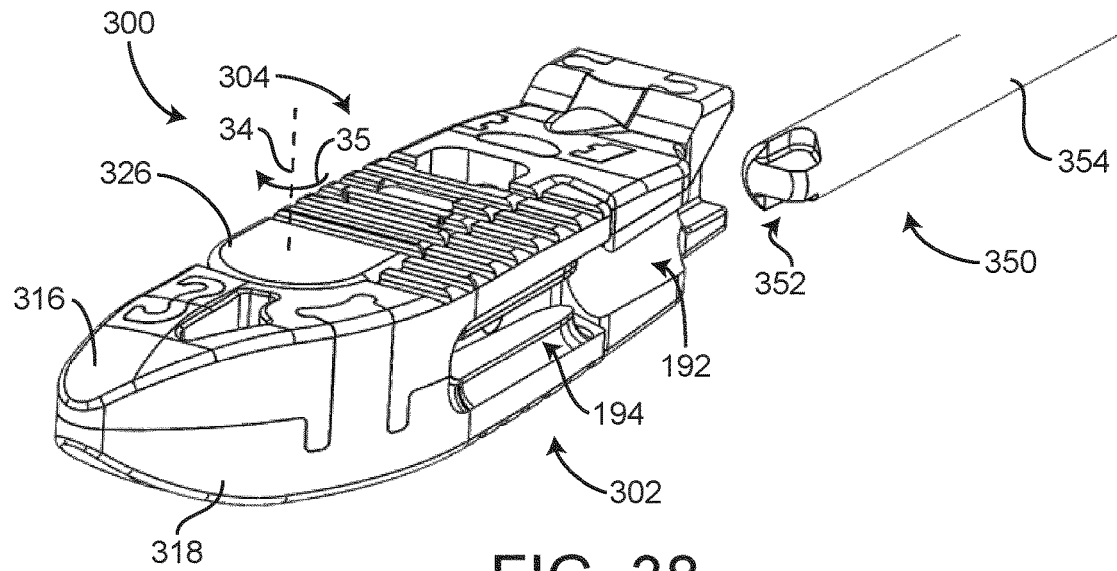

FIG. 38 is a perspective view of the implant of FIG. 25 being transitioned into a rotated configuration with a first adjustment tool, according to some embodiments.

Figure 39:
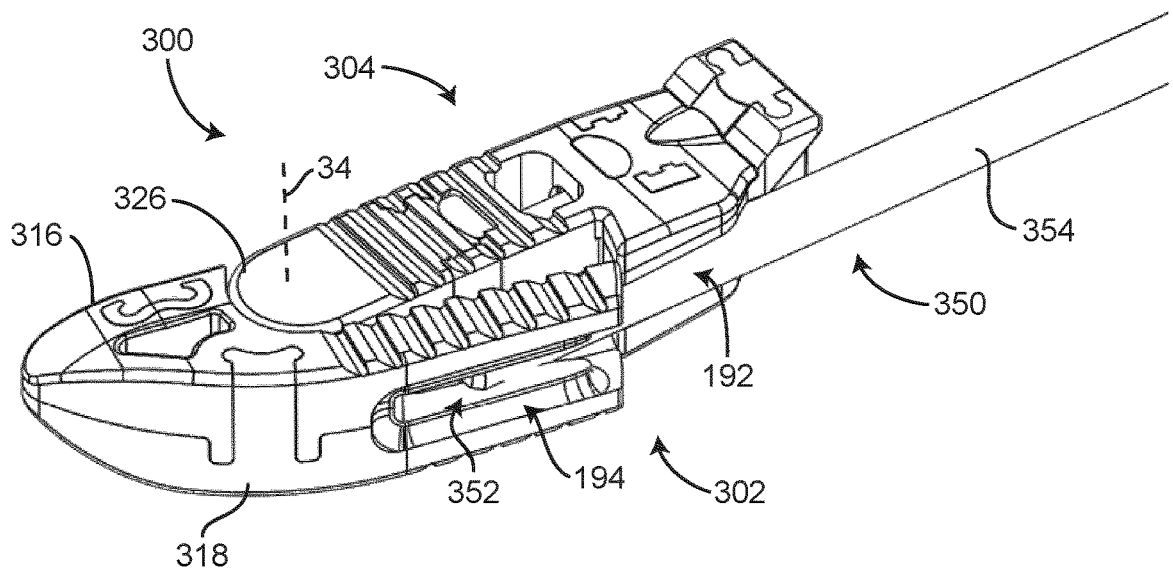

FIG. 39 is a perspective view of the implant of FIG. 25 being transitioned into a rotated configuration with a first adjustment tool, according to some embodiments.

Figure 40:
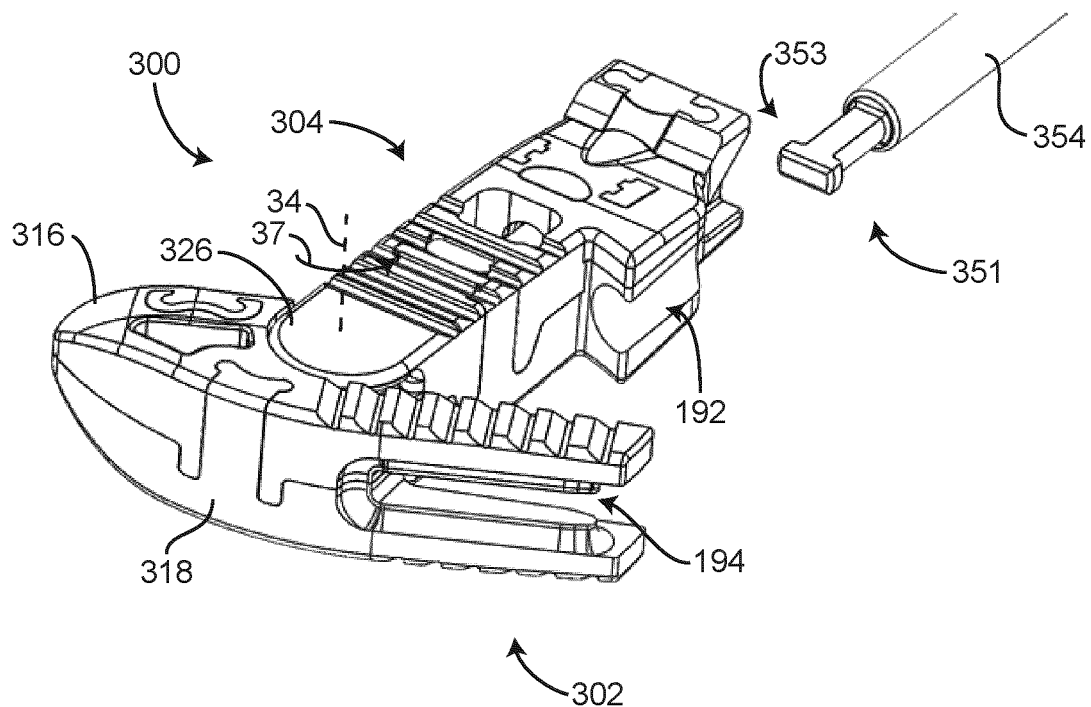

FIG. 40 is a perspective view of the implant of FIG. 25 being transitioned into a rotated configuration with a second adjustment tool, according to some embodiments.

Figure 41:
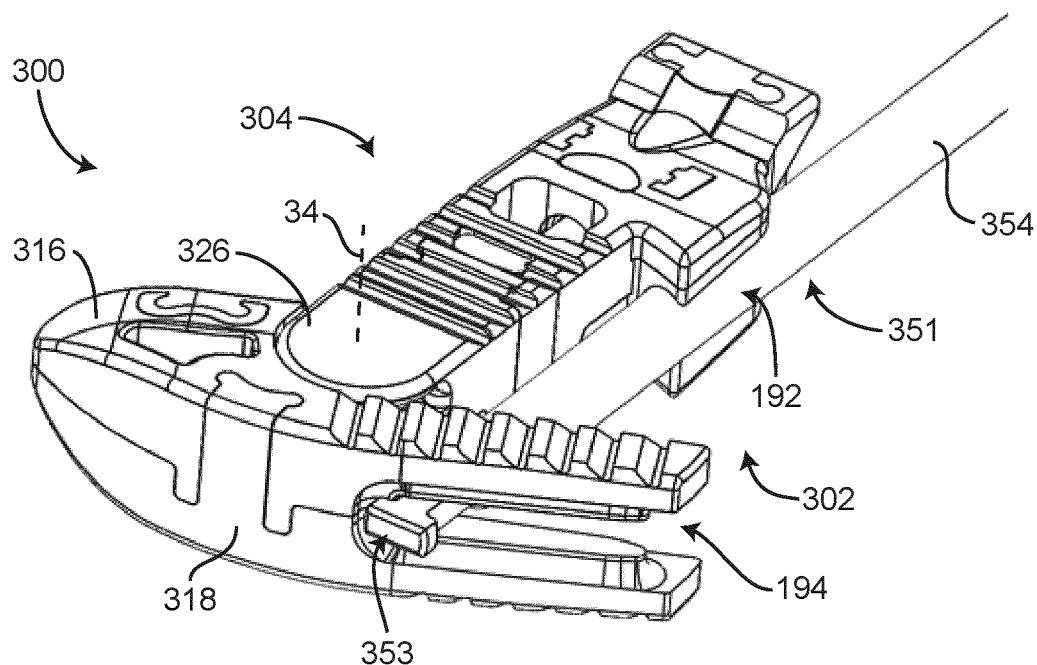

FIG. 41 is a perspective view of the implant of FIG. 25 being transitioned into a rotated configuration with a second adjustment tool, according to some embodiments.

Figure 42:
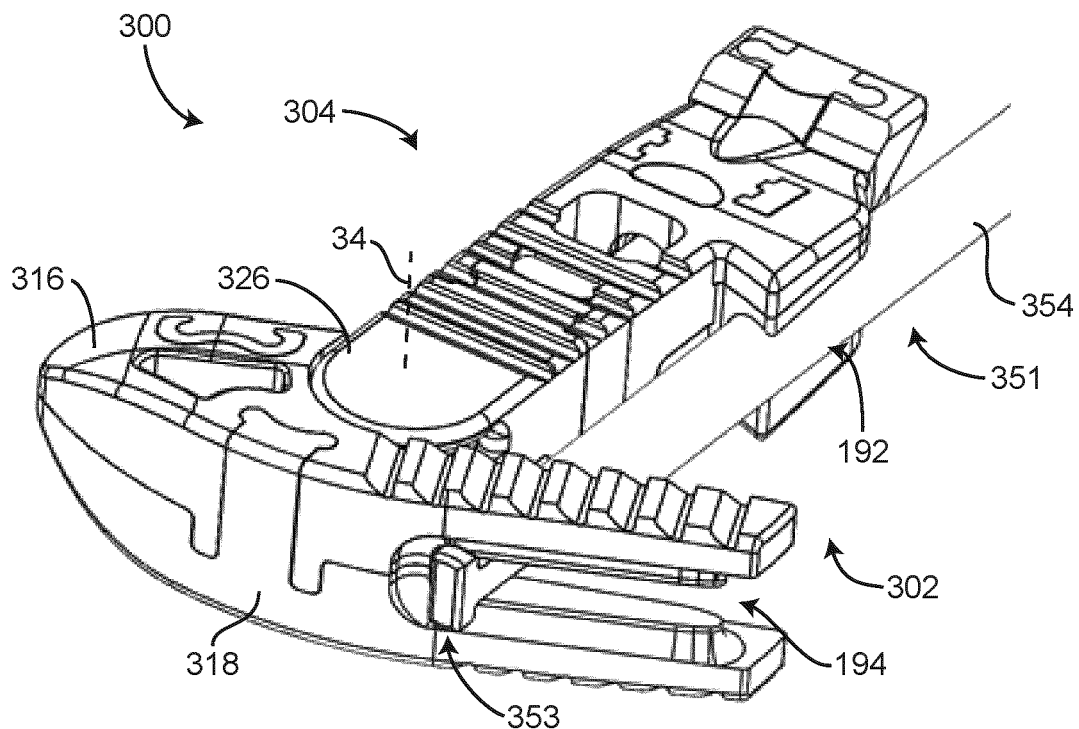

FIG. 42 is a perspective view of the implant of FIG. 25 being transitioned into a rotated configuration with a second adjustment tool, according to some embodiments.

Figure 43:
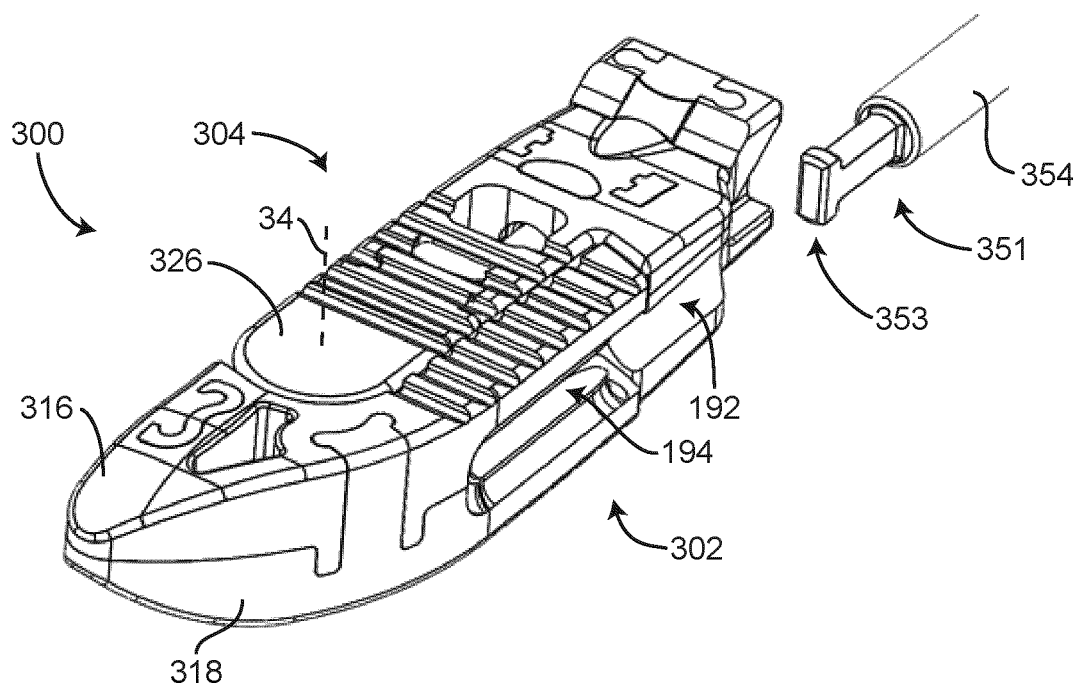

FIG. 43 is a perspective view of the implant of FIG. 25 being transitioned into a rotated configuration with a second adjustment tool, according to some embodiments.

Figure 44:
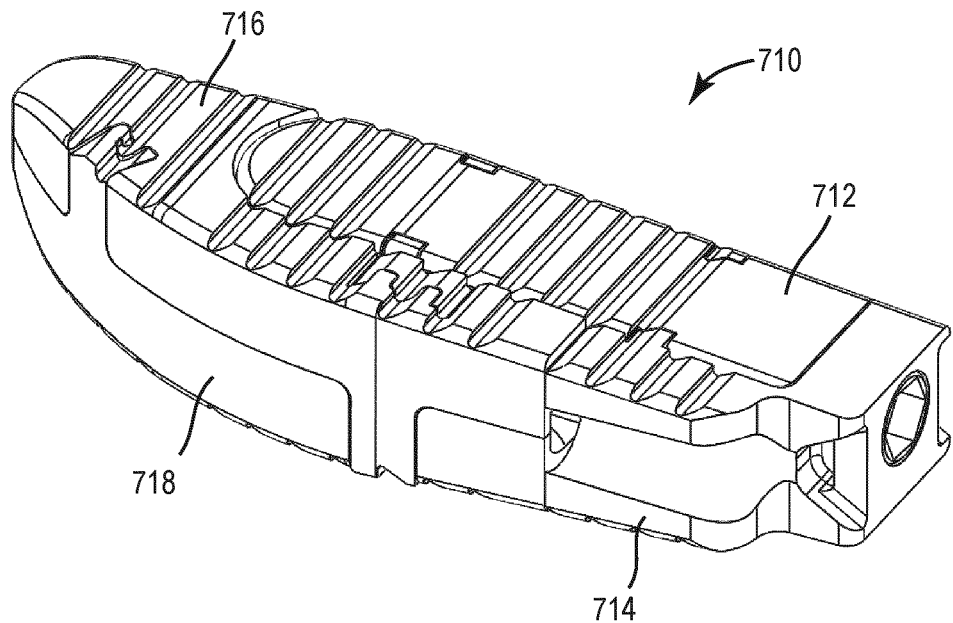

FIG. 44 is a perspective view of an implant according to another embodiment.

Figure 45:
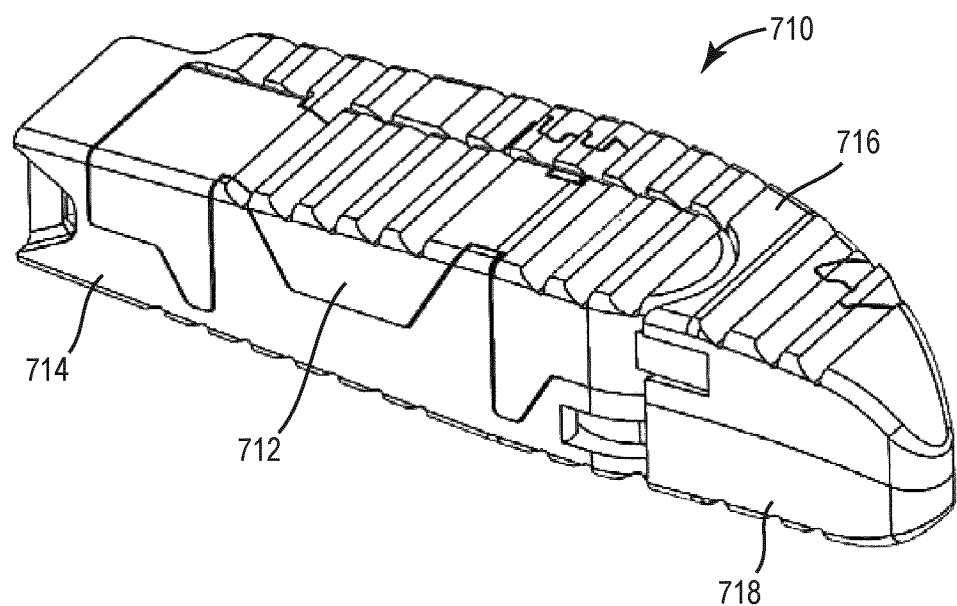

FIG. 45 is another perspective view of the implant of FIG. 44 according to one embodiment.

Figure 46:
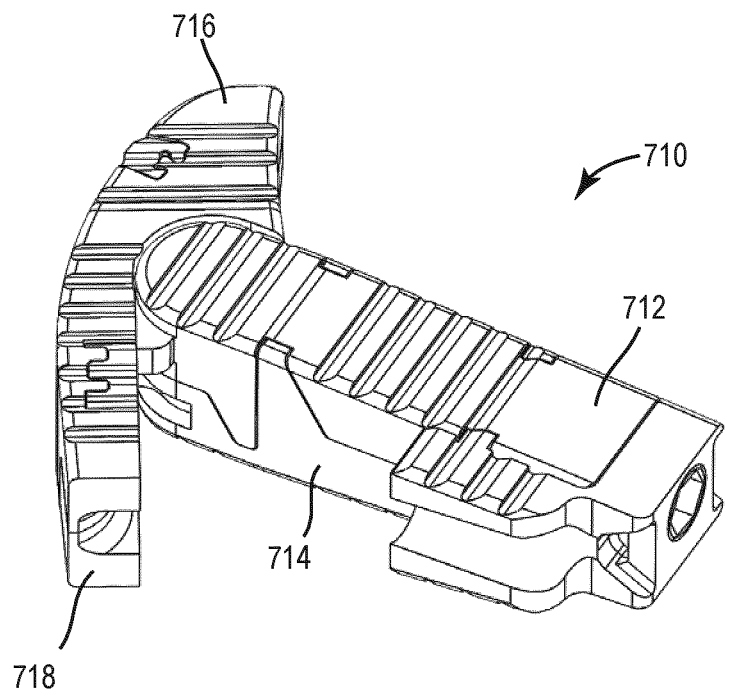

FIG. 46 is a perspective view of the implant of FIG. 44 in a rotated configuration according to one embodiment.

Figure 47:
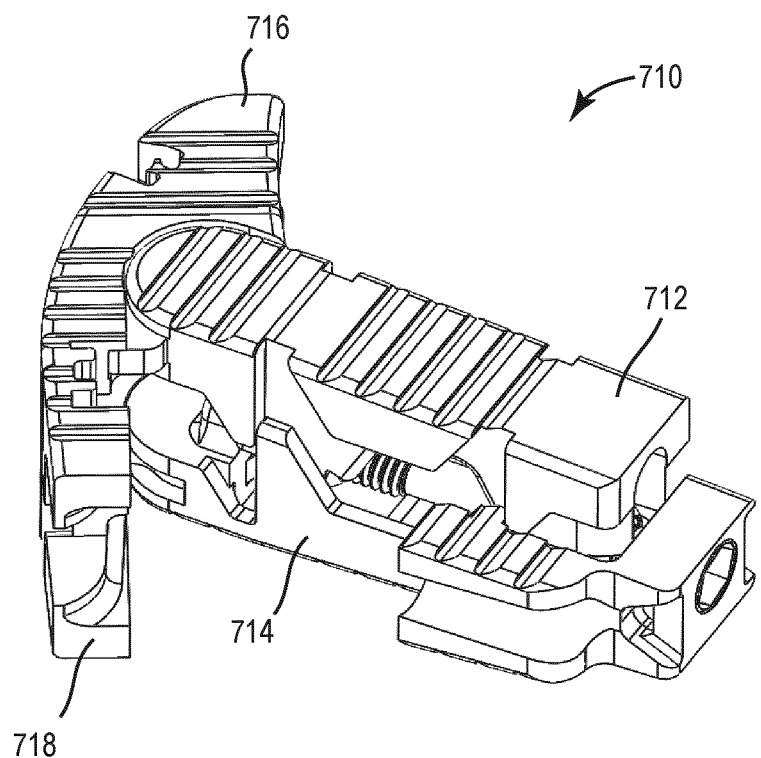

FIG. 47 is a perspective view of the implant of FIG. 44 in a rotated and expanded configuration according to one embodiment.

Figure 48:
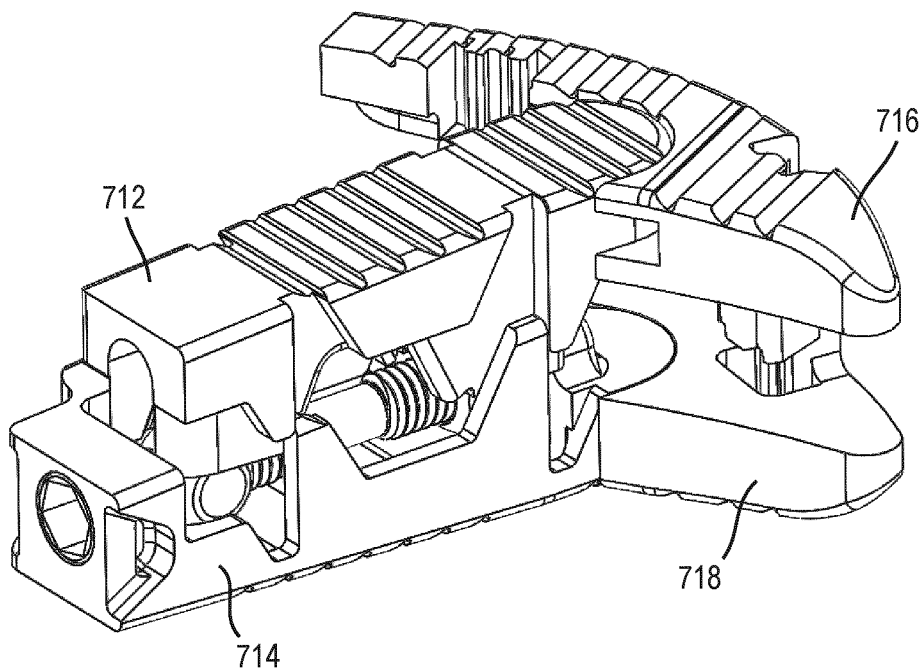

FIG. 48 is another perspective view of the implant of FIG. 44 in a rotated and expanded configuration according to one embodiment.

Figure 49:
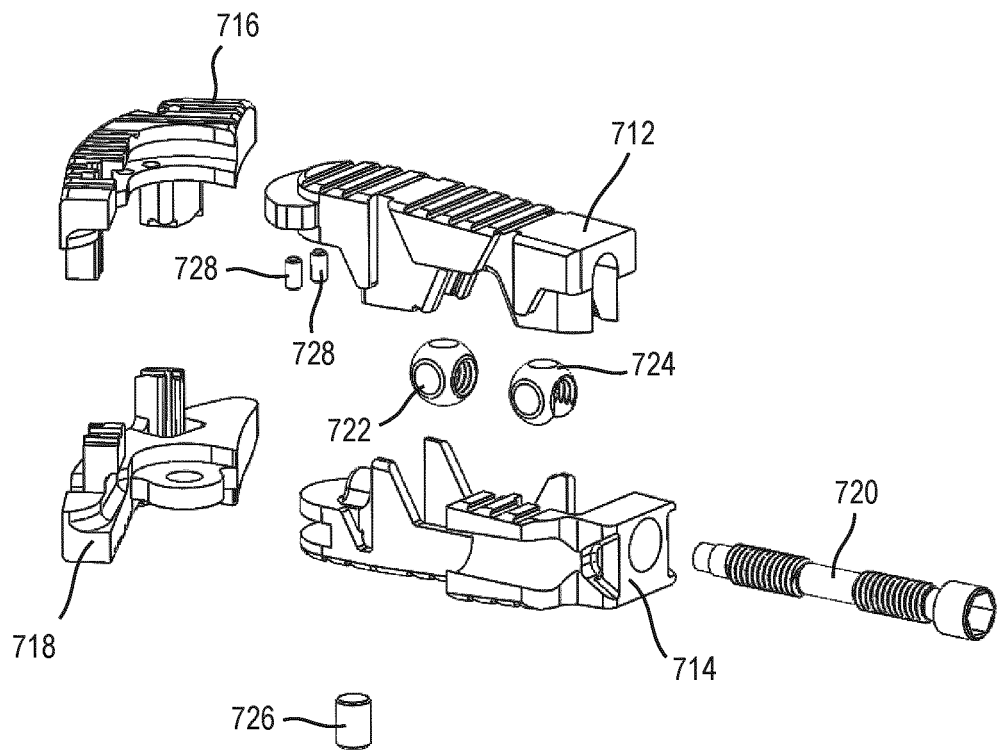

FIG. 49 is an exploded perspective view of the implant of FIG. 44 according to one embodiment.

Figure 50:
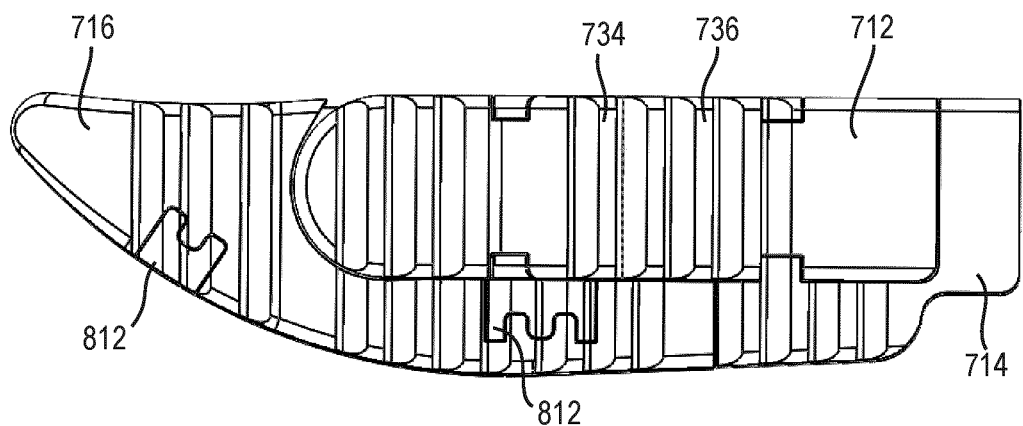

FIG. 50 is a top view of the implant of FIG. 44 according to one embodiment.

Figure 51:
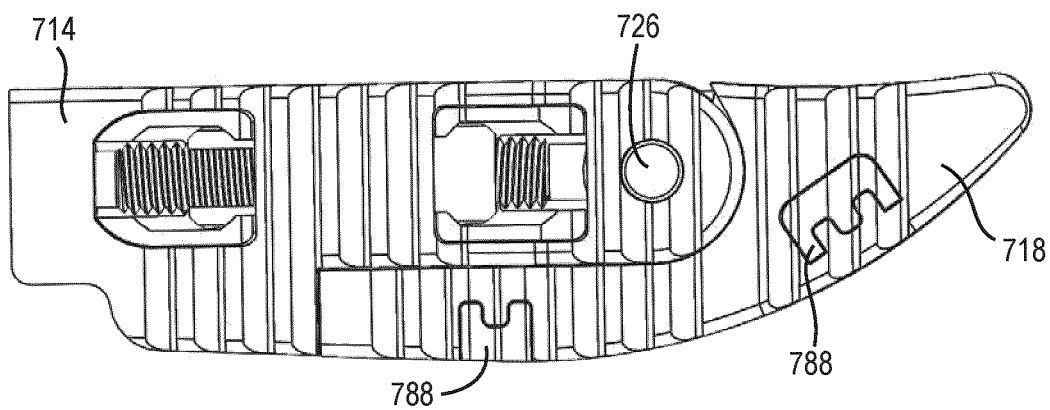

FIG. 51 is a bottom view of the implant of FIG. 44 according to one embodiment.

Figure 52:
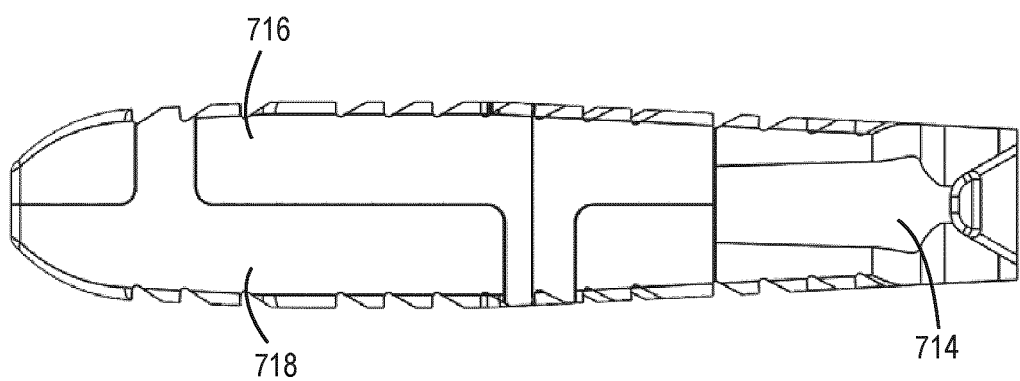

FIG. 52 is a side view of the implant of FIG. 44 according to one embodiment.

Figure 53:
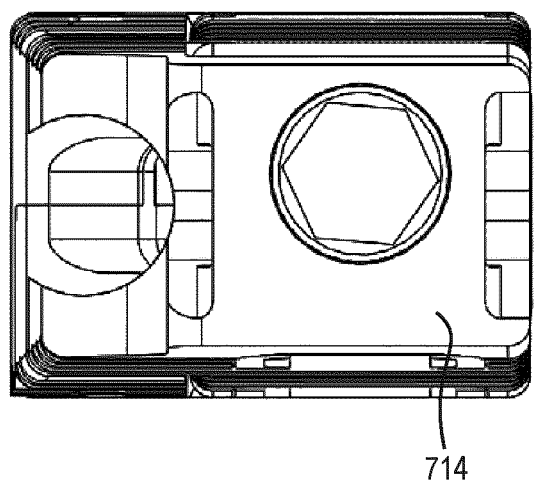

FIG. 53 is a front view of the implant of FIG. 44 according to one embodiment.

Figure 54:
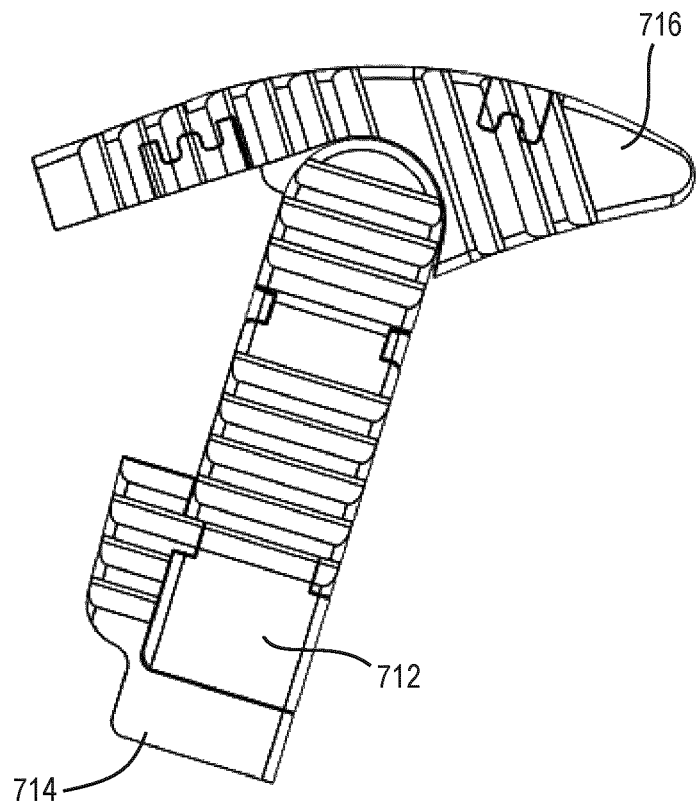

FIG. 54 is a top view of the implant of FIG. 44 in a rotated configuration according to one embodiment.

Figure 55:
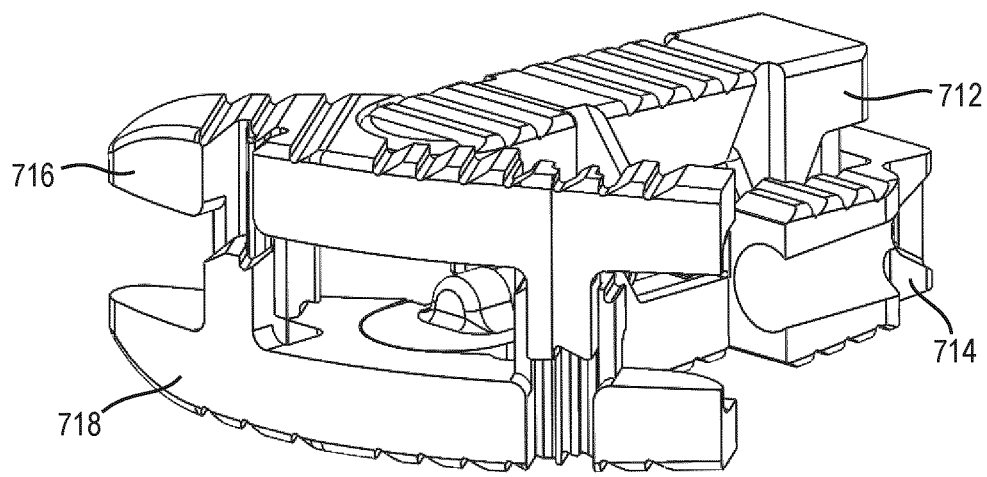

FIG. 55 is another perspective view of the implant of FIG. 44 in a rotated and expanded configuration according to one embodiment.

Figure 56:
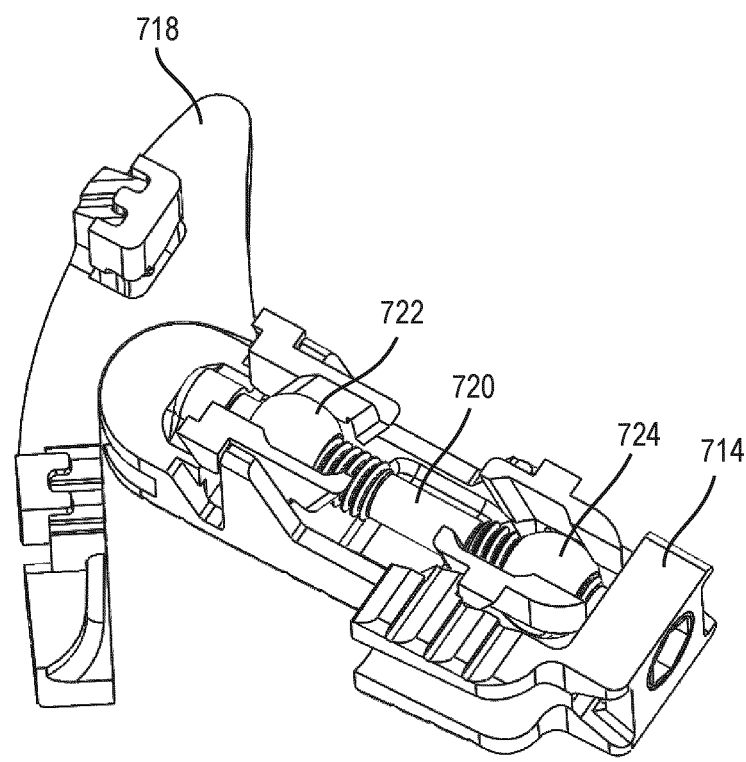

FIG. 56 is a cutaway perspective view of a portion of the implant of FIG. 44 according to one embodiment.

Figure 57:
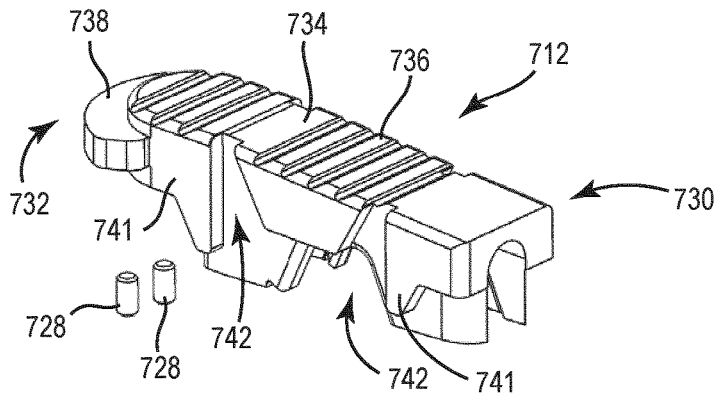

FIG. 57 is a perspective of an upper main support of the implant of FIG. 44 according to one embodiment.

Figure 58:
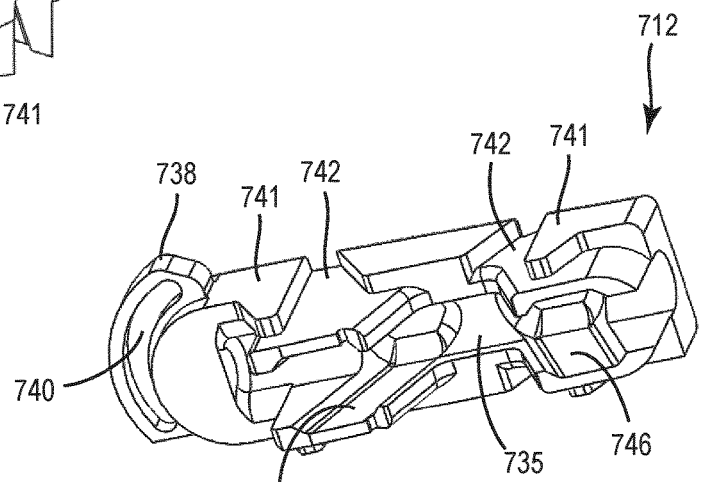

FIG. 58 is another perspective view of the upper main support of FIG. 57 according to one embodiment.

Figure 59:
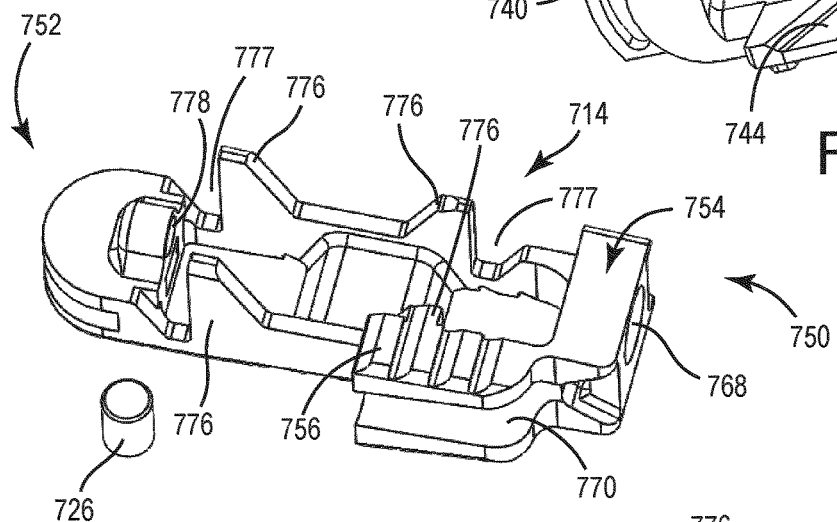

FIG. 59 is a perspective view of a lower main support of the implant of FIG. 44 according to one embodiment.

Figure 60:
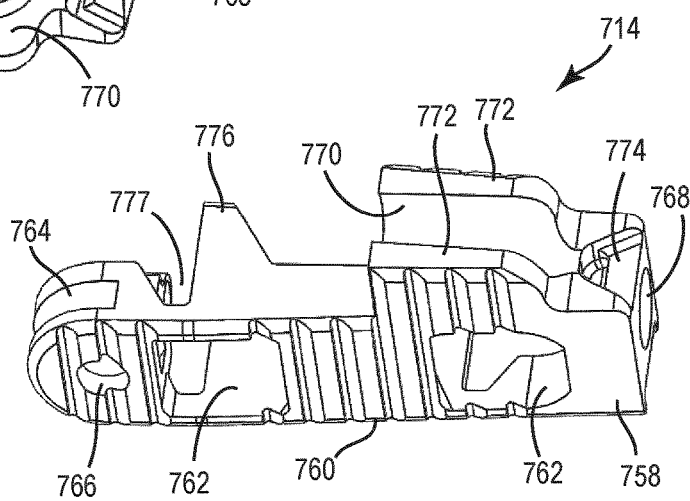

FIG. 60 is another perspective view of the lower main support of FIG. 59 according to one embodiment.

Figure 61:
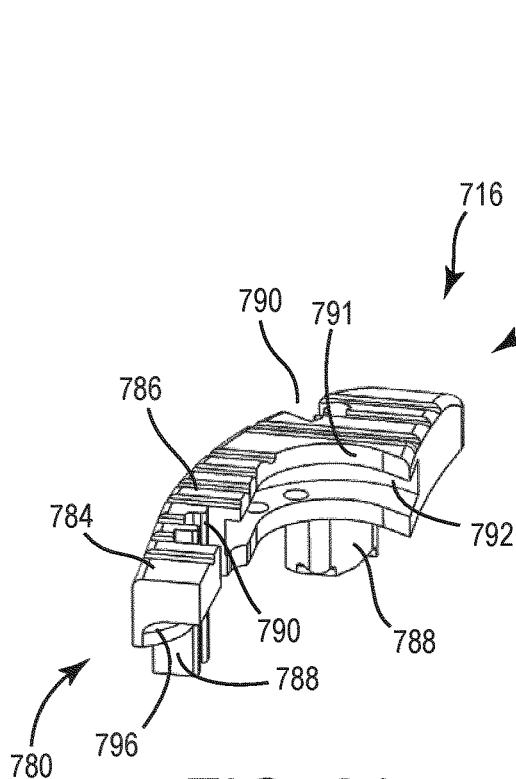

FIG. 61 is a perspective view of an upper pivoting support of the implant of FIG. 44 according to one embodiment.

Figure 62:
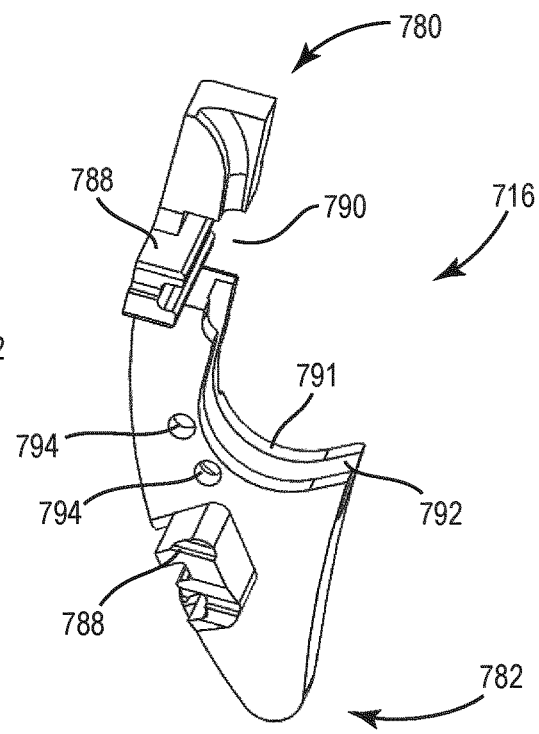

FIG. 62 is another perspective view of the upper pivoting support of FIG. 61 according to one embodiment.

Figure 63:
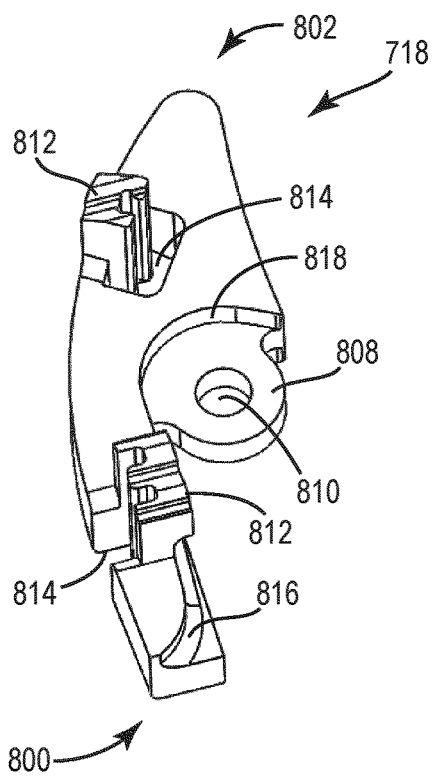

FIG. 63 is a perspective view of a lower pivoting support of the implant of FIG. 44 according to one embodiment.

Figure 64:
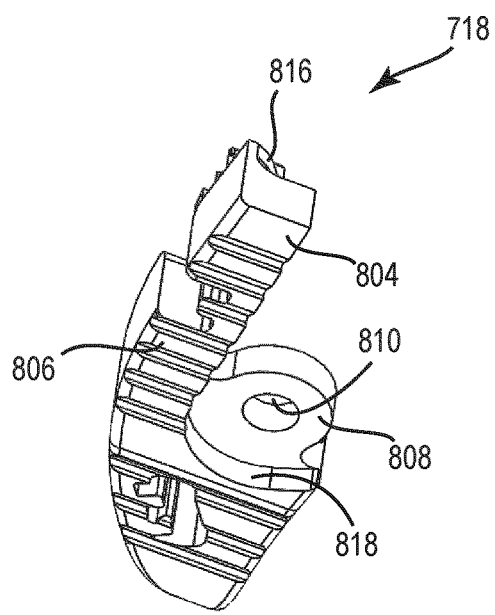

FIG. 64 is another perspective view of the lower pivoting support of FIG. 63 according to one embodiment.

Figure 65:
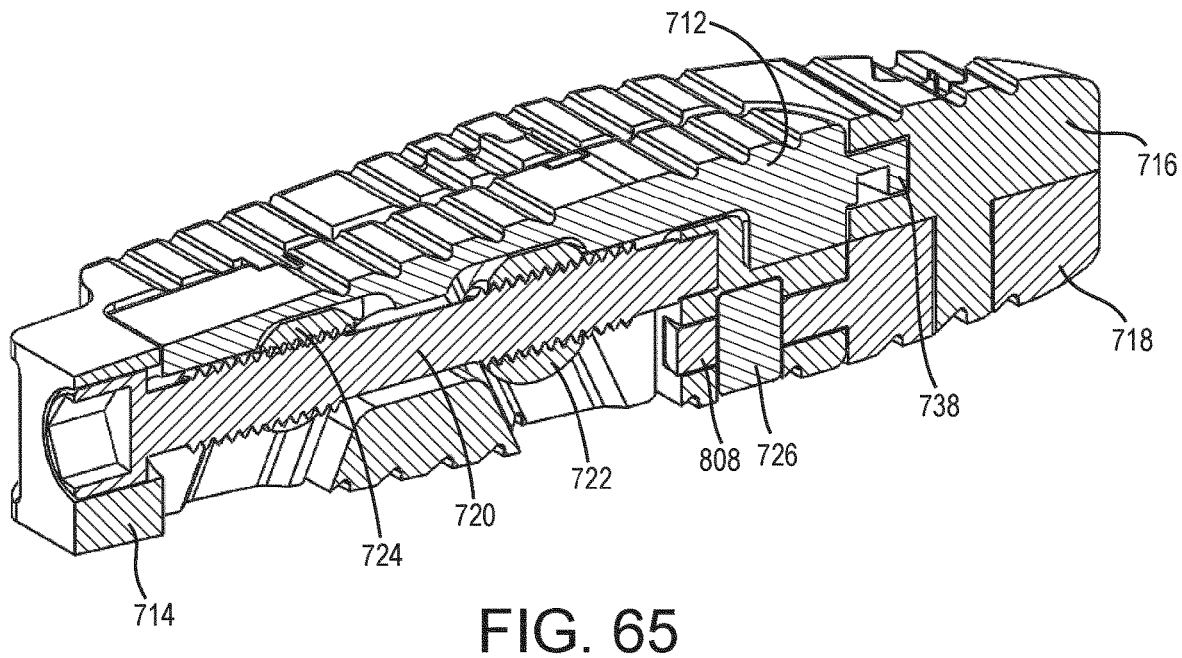

FIG. 65 is a cross sectional perspective view of the implant of FIG. 44 according to one embodiment.

Figure 66:
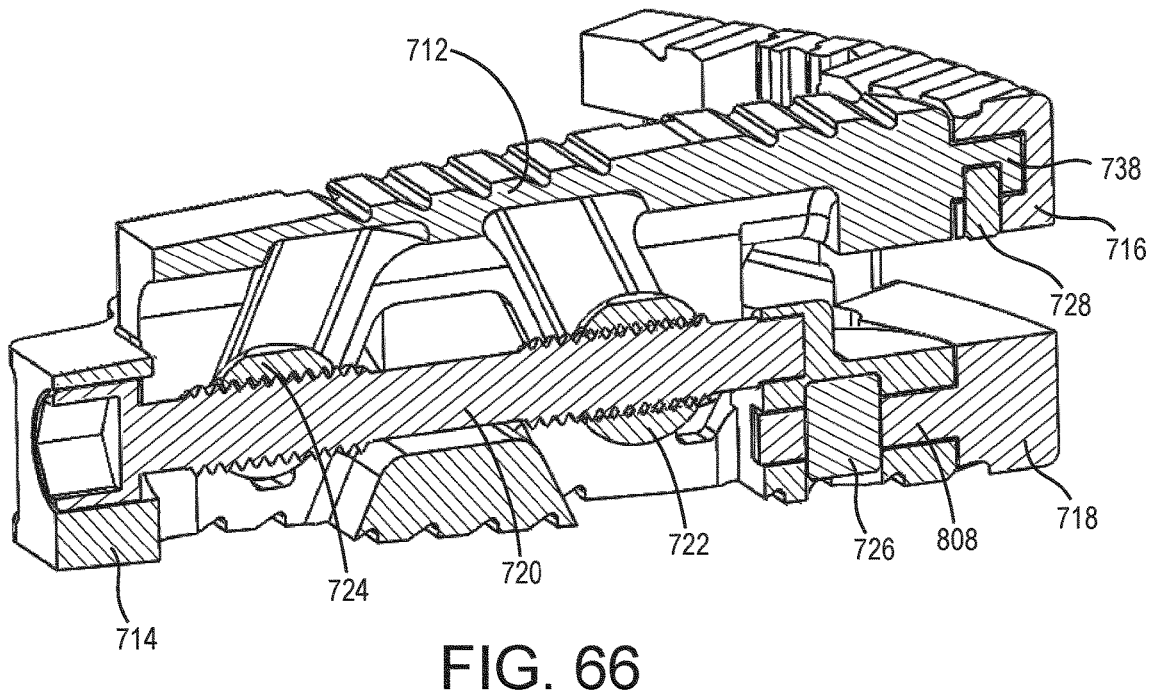

FIG. 66 is a cross sectional perspective view of the implant of FIG. 44 in a rotated and expanded configuration according to one embodiment.

Figure 67:
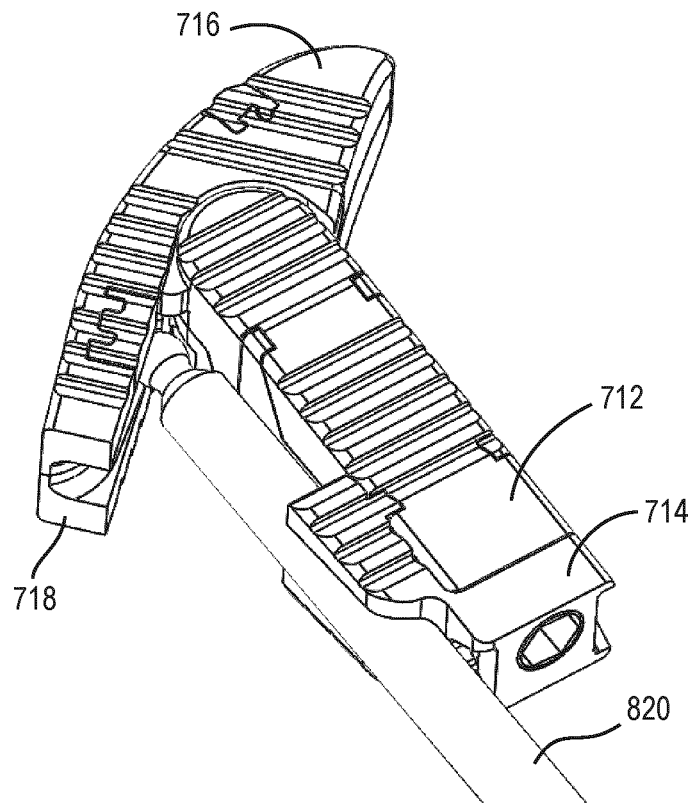

FIG. 67 is a perspective view of a tool and the implant of FIG. 44 according to one embodiment.

Figure 68:
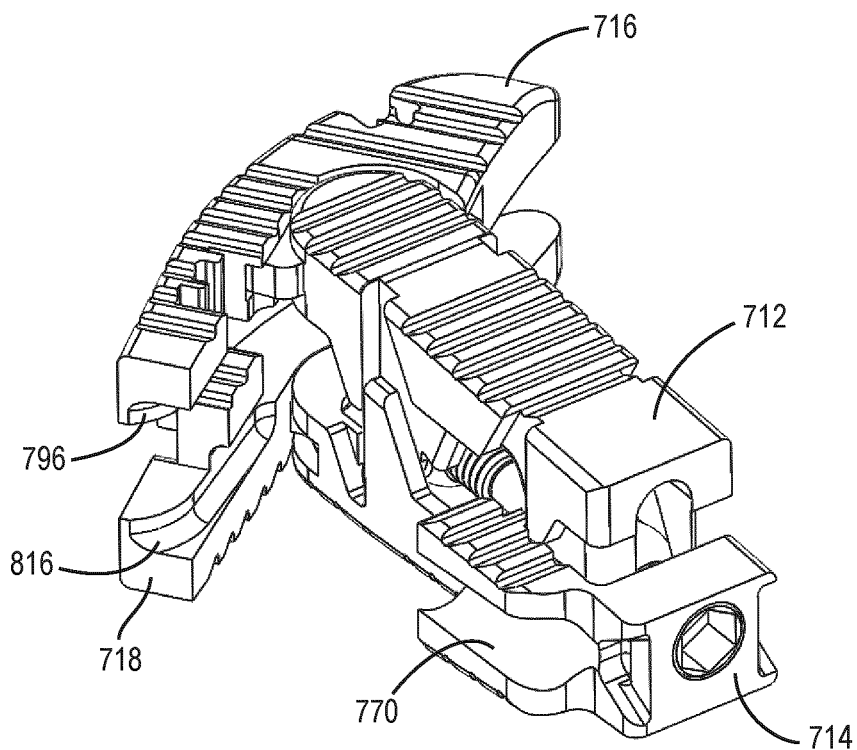

FIG. 68 is a perspective view of the implant of FIG. 44 in a rotated and expanded configuration according to one embodiment.

Figure 69:
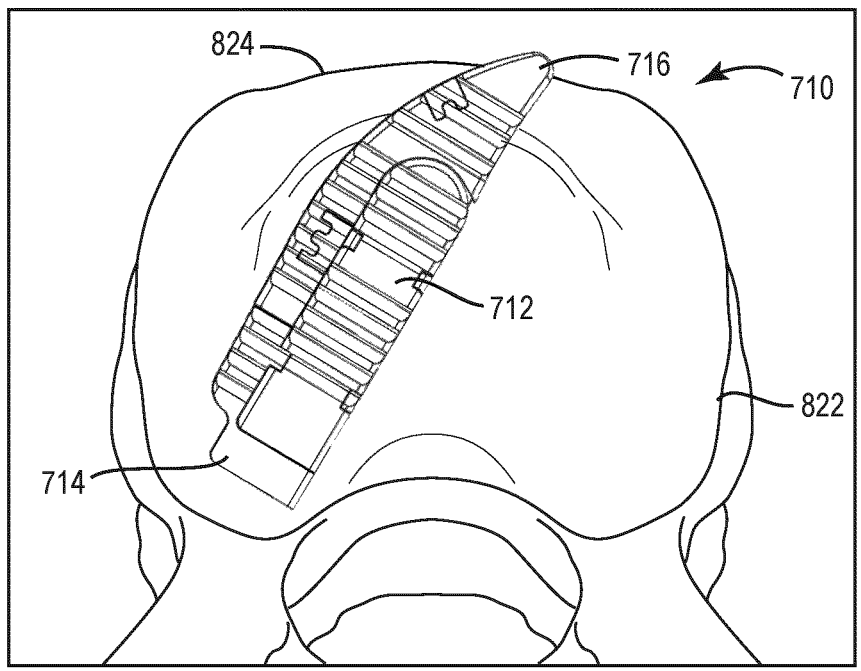

FIG. 69 is a top view of the implant of FIG. 44 in an implanted position according to one embodiment.

Figure 70:
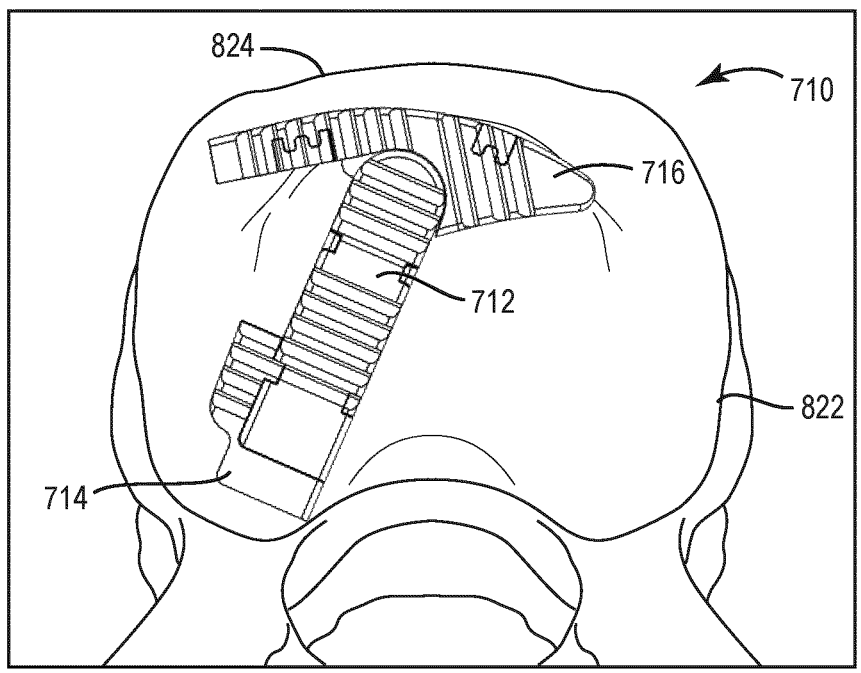

FIG. 70 is a top view of the implant of FIG. 44 in a rotated configuration and in an implanted position according to one embodiment.

Figure 71:
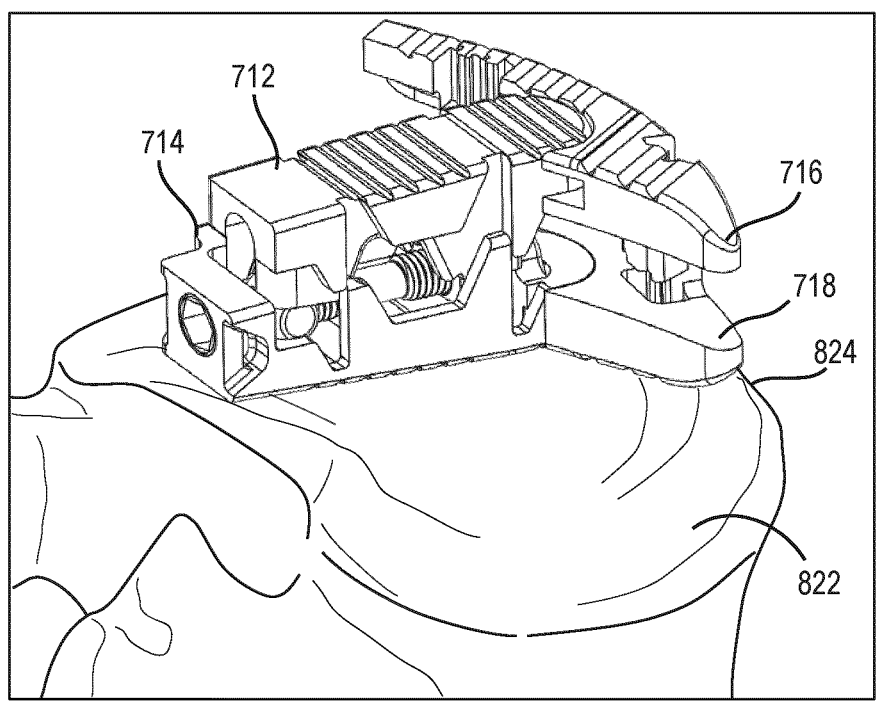

FIG. 71 is a perspective view of the implant of FIG. 44 in a rotated and expanded configuration and in an implanted position according to one embodiment.

Corresponding reference characters indicate corresponding parts throughout the several views. Although the drawings represent embodiments of the disclosure, the drawings are not necessarily to scale and certain features may be exaggerated in order to better illustrate and explain the principles of the present disclosure. The exemplifications set out herein illustrate several embodiments, but the exemplifications are not to be construed as limiting the scope of the disclosure in any manner.

DETAILED DESCRIPTION

The present disclosure relates to expandable and/or dynamic implants, including, but not limited to, interbody (between adjacent vertebrae), intravertebral-body (inside the vertebrae) and/or spinal stabilization devices that may or may not be used as interbody fusion cages or devices, interbody/intravertebral bodies/body stabilization devices and/or the like (e.g., spinal device(s)) for providing support, stabilization and/or promoting bone growth between or inside vertebrae or other portions of bone that have been destabilized or otherwise due to injury, illness and/or the like. Particularly, the present disclosure provides various versions of dynamic (expandable and/or expandable and retractable) interbody/intravertebral body devices that are usable in a spinal column or other areas of a human.

Various embodiments disclosed herein are directed to expandable implants that are implantable between adjacent bodies of bone. For example, the implant may be implanted or inserted into a human spine adjacent upper and lower vertebrae of the spine. According to various exemplary embodiments, the components of the implants disclosed herein may be made of any suitable material(s), including a variety of metals, plastics, composites, or other suitable bio-compatible materials. In some embodiments, one or more components of the implants disclosed herein may be made of the same material, while in other embodiments, different materials may be used for different components of the various implants.

Referring now to the FIGURES generally, various embodiments disclosed herein provide expandable implants including a base member, an adjustable member adjustably coupled to the base member and movable between a first, collapsed position, and a second, expanded position, and a control shaft rotatably received by the base member, where rotation of the control shaft cause relative movement of the adjustable member relative to the base member. At least one control member is received on the control shaft and by the control channel, and rotation of the control shaft causes the control member to translate along the control shaft and along the control channel.

In some embodiments, the adjustable member moves in a linear fashion relative to the base member. In other embodiments, the adjustable member moves in a non-linear fashion relative to the base member. In further embodiments, the adjustable member pivots about a pivot axis relative to the base member. The pivot axis may be provided by a pivot pin extending through one or both of the adjustable member and the base member.

In some embodiments, a single control member and control channel are utilized. In other embodiments, multiple (e.g., 2) control members and control channels are utilized. In some embodiments, the multiple control channels are parallel and straight. In other embodiments, the control channels are non-parallel and straight (e.g., angled toward each other). In further embodiments, the control channels are non-parallel and non-straight such that the adjustable member moves in a non-linear fashion relative to the base member.

In some embodiments, the control shaft includes a control thread corresponding to each control member. As such, while in some embodiments the control shaft includes a single control thread, in other embodiments the control shaft includes multiple (e.g., first and second) control threads. In some embodiments, the control threads are like-threaded. In other embodiments, the control threads have different threads. For example, in some embodiments, a first control thread is opposite-handed from a second control thread. In further embodiments, a first control thread has a different pitch from a second control thread. In yet further embodiments, a first control thread is different handed and has a different pitch from a second control thread.

In some embodiments, one or both of the adjustable member and the base member include projections/grooves to provide a gripping surface intended to facilitate gripping adjacent portions of bone. In further embodiments, one or both of the adjustable member and the base member include one or more apertures and/or cavities configured to promote bone growth in and around the adjustable member and the base member. In some embodiments, the apertures extend from a top, bottom, and/or side surface of the adjustment member or the base member and to a central cavity of the implant.

According to any of the embodiments disclosed herein, one or more bone screws may be included and positioned to extend through one or both of the adjustable member and the base member and into adjacent portions of bone. In some embodiments, multiple bone screws are used. A first bone screw may extend through the adjustable member and into a first portion of bone, and a second bone screw may extend through the base member and into a second portion of bone. In further embodiments, multiple bone screws are accessible and manipulatable by way of a front face of the implant defined by one or both of the adjustable member and the base member. A head and tool port of the control shaft may further be accessible by way of the front face of the implant.

In various embodiments, any suitable configuration of the control shaft/control member(s)/control channel(s) may be utilized. In some embodiments, an at least partially spherical control member threadingly engages a threaded control shaft and translates both along the control shaft and within the control channel. In other embodiments, the control member is non-spherical and is received at least partially on or in a control rail or control channel provided by the adjustable member, such that the control member translates along both the control shaft and the control channel or control rail. Various configurations of control shafts/control members/control channels are illustrated in U.S. Pat. No. 10,154,911, incorporated by reference herein in its entirety.

Referring now to FIGS. 1-12, an expandable implant 10 is shown according to an exemplary embodiment. Implant 10 is usable, for example, between and/or within vertebral bodies of the spine, and may share many of the features of the other inter/intra-body implants discussed elsewhere herein. It should be understood that implant 10 may in some embodiments be usable in other portions of the body in addition to the spine, and all such applications are to be understood to be within the scope of the present disclosure.

According to an exemplary embodiment, implant 10 includes a base assembly 12 and an adjustable assembly 14 adjustably coupled with base assembly 12. Adjustable assembly 14 can be adjusted to increase an overall height or thickness of implant 10 by translating (e.g., raising, lowering) relative to base assembly 12. In some embodiments, adjustable assembly 14 can be adjustably translated relative to base assembly 12 to expand or retract (e.g., collapse) implant 10. FIGS. 1-4 show implant 10 in a fully retracted state (e.g., a fully collapsed state), according to some embodiments. FIGS. 6, 7, 9, 10, and 11 show implant 10 in an at least partially expanded state, according to various other embodiments.

Implant 10 includes a front end, a front portion, a front side, etc., shown as front 11, a rear end, a rear portion, a back portion, a back end, a back side, a rear side, etc., shown as back 13, a right portion, a right side, a right end, etc., shown as right side 19, a left portion, a left side, a left end, etc., shown as left side 21, an upper end, an upper portion, an upper side, a top end, a top portion, a top side, etc., shown as top 15, and a bottom portion, a bottom end, a bottom side, etc., shown as bottom 17. Base assembly 12 is positioned below adjustable assembly 14. Adjustable assembly 14 is configured to raise/lower relative to base assembly 12.

Base assembly 12 can include a base member 20 (e.g., a lower main support), and an end member, a rotatably coupled member, a lower pivoting support, a pivotally coupled member, etc., shown as rotatable base member 18. Rotatable base member 18 and base member 20 are rotatably coupled and at least partially form base assembly 12. Base member 20 includes a first portion, shown as front portion 22, and a second portion, shown as rear portion 24 (see FIG. 8). Rotatable base member 18 is rotatably coupled with base member 20 at front portion 22. Likewise, adjustable assembly 14 includes a body portion, an upper main support, etc., shown as body member 26 that corresponds to base member 20. Body member 26 is rotatably coupled with a rotatable member 16 (e.g., an upper pivoting support) at a first portion, shown as front portion 30 of body member 26.

Rotatable member 16 of adjustable assembly 14 and rotatable base member 18 of base assembly 12 are configured to rotate together (e.g., in unison) about a central axis 34 (e.g., a pivoting axis). Central axis 34 extends between the rotatable/pivotal coupling between rotatable member 16 and body member 26, as well as the rotatable/pivotal coupling between rotatable base member 18 and base member 20. In this way, rotatable member 16 of adjustable assembly 14 and rotatable base member 18 of base assembly 12 rotate together about central axis 34 relative to base member 20 and/or body member 26. In some embodiments, central axis 34 is translationally fixed relative to base member 20 and/or body member 26. In some embodiments, central axis 34 translates relative to base member 20 and/or body member 26 as rotatable base member 18 and/or rotatable member 16 pivot/rotate relative to base member 20 and/or body member 26. In other words, the relative movement between components may be rotational, translational, or a combination thereof. Rotatable member 16 and rotatable base member 18 can define or form a head assembly, a nose assembly, a rotatable assembly, a pivoting assembly, a pivotal assembly, shown as pivotal nose 32. Likewise, base member 20 and body member 26 can define or form a body assembly, a main assembly. Pivotal nose 32 is configured to pivot or rotate relative to the body assembly formed by base member 20 and body member 26. In some embodiments, pivotal nose 32 is configured to pivot or rotate about central axis 34 relative to the main assembly. For example, pivotal nose 32 can be configured to pivot about a stationary axis that extends through a pin. In other embodiments, pivotal nose 32 is free to translate relative to the main assembly as pivotal nose 32 pivots or rotates relative to the main assembly. For example, pivotal nose 32 and the base assembly can be pivotally and translatably coupled with each other through a track, a groove, a set of grooves, a set of channels, etc., such that pivotal nose 32 translates relative to the main or body assembly as pivotal nose 32 rotates/pivots.

Body member 26 of adjustable assembly 14 includes a rear end, a distal end, a second end, a second portion, shown as rear portion 28. Rear portion 28 is an opposite portion of front portion 30 of body member 26. Body member 26 includes a cavity 100 (e.g., a hole, an aperture, a blind hole, a recess, etc.) therebetween front portion 30 and rear portion 28. Cavity 100 can extend substantially through an entire thickness of body member 26. In other embodiments, cavity 100 extends only partially through the entire thickness of body member 26. Cavity 100 can provide surface area and volume for bone tissue to grow into and thereby facilitates stability between implant 10 and the bones that implant 10 is implanted into or between. Body member 26 of adjustable assembly 14 can include any number of cavities, recessions, apertures, holes, grooves, etc., similar to cavity 100 to facilitate bone growth and facilitate stability between implant 10 and the bones that implant 10 is implanted into or between.

Body member 26 can include any number of projections, grooves, ridges, protrusions, etc., shown as projections 36 along an exterior surface of body member 26. Projections 36 can be defined between adjacent grooves of the exterior (e.g., upper, top, outer, etc.) surface of body member 26. Projections 36 can cover substantially an entirety (or part of) the exterior surface of body member 26. Projections 36 are configured to engage adjacent portions of bone.

Rotatable member 16 can also include any number of projections, grooves, ridges, protrusions, etc., shown as projections 38 along an exterior surface of rotatable member 16. Projections 38 can be defined between adjacent grooves of the exterior surface (e.g., upper, top, outer, etc.) of body member 26. Projections 38 can cover substantially an entirety (or part of) of the exterior surface of rotatable member 16. Projections 38 are configured to engage adjacent portions of bone.

Rotatable base member 18 can also include any number of projections, grooves, ridges, protrusions, etc., shown as projections 40 along an exterior surface of rotatable base member 18. Projections 40 can be defined between adjacent grooves of the exterior surface (e.g., lower, bottom, outer, etc.) of rotatable base member 18. Projections 40 can cover substantially an entirety (or part of) the exterior surface of rotatable base member 18. Projections 40 are configured to engage adjacent portions of bone.

Base member 20 can also include any number of projections, grooves, ridges, protrusions, etc., shown as projections 42 along an exterior surface of base member 20. Projections 42 can be defined between adjacent grooves of the exterior surface (e.g., a lower, bottom, outer, etc.) of base member 20. Projections 42 can cover substantially an entirety (or part of) the exterior surface of base member 20. Projections 42 are configured to engage adjacent portions of bone.

Referring particularly to FIG. 8, base member 20 can include an aperture, a bore, a through-hole, a blind hole, etc., shown as receiving aperture 46. Receiving aperture 46 can extend substantially through an entire thickness of base member 20 or only partially through the entire thickness of base member 20. Receiving aperture 46 is configured to receive a pin, an elongated member, a cylindrical member, a post, a cylinder, a shaft, etc., shown as pin 48 therethrough. Receiving aperture 46 of base member 20 can correspond to (e.g., be co-linear with) an aperture, bore, through-hole, blind hole, etc., of rotatable base member 18, shown as aperture 44 (see FIG. 7). Receiving aperture 46 and aperture 44 can be concentric with each other and receive pin 48 therethrough. Pin 48 extends into receiving aperture 46 and aperture 44 to rotatably couple base member 20 and rotatable base member 18. Pin 48 can include a chamfered end to facilitate maintaining pin 48 in receiving aperture 46 and aperture 44 (e.g., to prevent pin 48 from sliding through receiving aperture 46 and aperture 44). Pin 48 can be press fit, slip fit, etc., into receiving aperture 46 and aperture 44. In some embodiments, pin 48 is press fit (e.g., interference fit) with aperture 44 of rotatable base member 18 and is slip fit with receiving aperture 46 of base member 20. Rotatable base member 18 can be slidably coupled with an exterior surface (e.g., a bottom surface) of base member 20.

Referring particularly to FIGS. 1, 7, 8, and 9, body member 26 of adjustable assembly 14 can include a slot, a receiving portion, a groove, a recession, etc., shown as receiving slot 50. Receiving slot 50 can be positioned at an outer end (e.g., at front portion 30) of body member 26. Receiving slot 50 is configured to receive a corresponding shaped extension, protrusion, elongated portion, generally flat protrusion, etc., of rotatable member 16, shown as protrusion 52 (see FIG. 7). Protrusion 52 is configured to be received within receiving slot 50. Protrusion 52 can be adjacent surfaces of slot 50. In some embodiments, protrusion 52 slidably interfaces with the adjacent (e.g., opposite surfaces that define slot 50) surfaces of slot 50 to facilitate rotatable or pivotal coupling between body member 26 and rotatable member 16. In some embodiments, a gap is formed between exterior surfaces of protrusion 52 and opposite/offset surfaces of slot 50 that define slot 50.

A bottom portion, a lower portion, a tab, a protrusion, etc., shown as protrusion 56 that defines a bottom end of receiving slot 50 of body member 26 includes an aperture 54 therethrough. Protrusion 52 can include a corresponding aperture that is concentric with aperture 54. The corresponding aperture of protrusion 52 and aperture 54 are configured to receive a pin, a post, an elongated member, a shaft, a cylinder, a cylindrical member, etc., shown as pin 58 therethrough. In some embodiments, pin 58 facilitates the rotatable coupling between rotatable member 16 and body member 26. Pin 58 can be press fit with at least one of aperture 54 of protrusion 56 and the corresponding aperture of protrusion 52, and slip fit (e.g., rotatably coupled) with the other one of aperture 54 and the corresponding aperture of protrusion 52. In this way, pin 58 facilitates rotatable coupling between rotatable member 16 and body member 26. Pin 58 can be a hollow cylindrical member, a solid cylindrical member, etc. Pin 58 and pin 48 can be substantially co-cylindrical with each other and define central axis 34.

Referring particularly to FIGS. 8, 11, and 12, rotatable member 16 can include a hollow protrusion 62. Hollow protrusion 62 can extend in a direction substantially parallel with central axis 34. Hollow protrusion 62 can extend from an underside, an interior surface, etc., of rotatable member 16. Hollow protrusion 62 can have an exterior perimeter that is smaller than a corresponding exterior perimeter of rotatable member 16. Hollow protrusion 62 includes an aperture, a recess, an opening, a window, etc., shown as cavity 66 that extends therethrough. In some embodiments, cavity 66 extends in a direction that is also substantially parallel with central axis 34.

Hollow protrusion 62 is configured to be received within a corresponding aperture, hole, recess, cavity, opening, window, etc., of rotatable base member 18, shown as cavity 60. Cavity 60 is configured to receive hollow protrusion 62 therewithin. Cavity 60 can have a shape (e.g., a perimeter) that corresponds to an outer perimeter or shape of hollow protrusion 62. An interior surface of cavity 60 (e.g., an inner side wall, an inner surface, etc.) can be configured to slidably interface with an exterior surface of hollow protrusion 62. In some embodiments, cavity 60 has a same shape/perimeter as hollow protrusion 62 that is greater than an exterior surface of hollow protrusion 62 such that hollow protrusion 62 can be received therewithin and a gap is formed between the exterior surface of hollow protrusion 62 and the interior surface of cavity 60.

Hollow protrusion 62 can include one or more apertures, holes, through-holes, etc., shown as aperture 68. Apertures 68 can extend substantially through both sidewalls of hollow protrusion 62. In some embodiments, aperture 68 extend in a direction that is substantially perpendicular with central axis 34. Apertures 68 can be spaced apart a uniform distance along a direction parallel with central axis 34. Apertures 68 can be spaced apart along substantially an entire height of hollow protrusion 62.

Rotatable base member 18 includes one or more tabs, protrusions, etc., shown as protrusions 64. Protrusions 64 extend from one or more sides of an outer perimeter of cavity 60. Protrusions 64 can extend in a direction that is substantially parallel with central axis 34. Protrusions 64 can be integrally formed with rotatable base member 18. Protrusions 64 both include an aperture, a hole, a through-hole, a bore, etc., shown as apertures 70. Apertures 70 can be disposed on protrusions 64 on opposite sides of the perimeter of cavity 60. Apertures 70 can be concentric with each other to form a line of sight therethrough. Apertures 70 can have a size and shape corresponding to aperture 68.

Protrusions 64 are configured to be received within corresponding recesses, cavities, grooves, slots, etc., of rotatable member 16, shown as recesses 164. Recesses 164 can receive protrusions 64 completely therewithin when implant 10 is in the fully retracted position (as shown in FIGS. 1-5).

Protrusions 64 can include recesses, slots, grooves, channels, etc., shown as tracks 166 that extend along substantially an entire height of protrusions 64. In some embodiments, tracks 166 are semi-circular in their cross-sectional shape. In some embodiments, tracks 166 extend along substantially an entire overall height (e.g., an entire thickness) of rotatable base member 18. For example, tracks 166 can extend along an inner surface of protrusions 64 and cavity 60 (as shown best in FIG. 10).

Tracks 166 are configured to receive and slidably couple with correspondingly shaped protrusions, ridges, elongated protrusions, track members, etc., shown as protrusions 168 (shown in FIG. 12). As implant 10 is expanded and retracted/collapsed, protrusions 168 translate along tracks 166. The slidable coupling between protrusions 168 and tracks 166 facilitates stability between adjustable assembly 14 and base assembly 12 as implant 10 is expanded or retracted. Protrusions 168 can have a corresponding cross-sectional shape as tracks 166 (e.g., a semi-circular shape). Protrusions 168 can have any other cross-sectional shape (e.g., a square cross-sectional shape, a rectangular cross sectional shape, an irregular cross-sectional shape, etc.) that is configured to slidably couple with correspondingly shaped tracks 166. Protrusions 168 can extend along substantially an entire height of hollow protrusion 62 (as best shown in FIG. 8).

As adjustable assembly 14 is driven to translate relative to base assembly 12, apertures 68 may move across apertures 70, forming a line of sight therethrough. For example, apertures 68 may translate past apertures 70, and overlapping areas of apertures 68 and 70 allow light to pass therethrough. In some embodiments, this can be viewed on an x-ray. This facilitates allowing a surgeon that is implanting implant 10 to know/see a degree of extension/expansion and retraction/collapsing of implant 10. The function of apertures 68 and 70 is described in greater detail below with reference to FIGS. 13A-13D.

Referring particularly to FIGS. 8 and 12, implant 10 can include a control shaft 72. Control shaft 72 is configured to be driven (e.g., rotated clockwise, rotated counter-clockwise) to extend and retract adjustable assembly 14 relative to base assembly 12. Specifically, rotating/driving control shaft 72 translates (e.g., expands or retracts/collapses) body member 26 and rotatable member 16 in unison relative to base assembly 12 (e.g., relative to base member 20 and rotatable base member 18). Control shaft 72 can be driven to expand adjustable assembly 14 relative to base assembly 12 after rotatable member 16 and rotatable base member 18 have been rotated about central axis 34 to a desired angular position.

Base member 20 includes a receiving portion 80 at rear portion 24 (e.g., at a rear end of base member 20). Receiving portion 80 includes an aperture, shown as control bore 78. Control bore 78 is configured to rotatably interface with a corresponding portion of control shaft 72. Control shaft 72 includes an interfacing portion 74. Interfacing portion 74 is configured to interface with (e.g., removably couple with) an adjustment tool and facilitates the transfer of rotation from the adjustment tool to control shaft 72. Interfacing portion 74 can be a hexagonal shaped recess, a cross-shaped recess, a slot shaped recess, a star shaped recess, etc., or any other recess or protrusion configured to interface with a correspondingly shaped protrusion or recess of the adjustment tool. Interfacing portion 74 can include a port, a cavity, a recess, a channel, etc., shown as bone graft port 75 that extends therethrough. Bone graft port 75 is configured to receive gone tissue that can grow therethrough and facilitates fusion or connection between implant 10 and adjacent bone.

Control shaft 72 includes one or more sets of threads 76 (e.g., control threads). A first set of threads 76a is configured to threadingly couple with a first control member 86a and a second set of threads 76b is configured to threadingly couple with a second control member 86b. First control member 86a can include threads 96a configured to threadingly couple (e.g., threadingly interface) with first set of threads 76a. Second control member 86b can include threads 96b configured to threadingly couple (e.g., threadingly interface) with second set of threads 76b.

Base member 20 includes a shelf, a groove, a recess, a track, a surface, etc., shown as track 88. Track 88 extends at least partially along a length of base member 20. Track 88 can have the form of a shelf. Track 88 is configured to slidably couple with a corresponding engagement or receiving portion 90 of each of control members 86. For example, first control member 86a can include receiving portion 90a that slidably couples with track 88 and facilitates translation of first control member 86a along track 88. Likewise, second control member 86b can include receiving portion 90b that slidably couples with track 88 and facilitates translation of second control member 86b along track 88.

Control shaft 72 can drive first control member 86a and second control member 86b to translate along track 88 through the threaded coupling between threads 76 of control shaft 72 and threads 96 of control members 86. Threads 76a and threads 76b can be oppositely oriented threads to facilitate translation of first control member 86a and second control member 86b in opposite directions along track 88 in response to rotation of control shaft 72. For example, threads 76a may be right-hand oriented threads, while threads 76b may be left-hand oriented threads, or vice versa. Likewise, threads 96a and threads 96b can be oppositely oriented threads (with respect to each other) that correspond to and are configured to threadingly interface with threads 76a and threads 76b, respectively.

In some embodiments, interfacing portion 74 of control shaft 72 is configured to be received within control bore 78. An end of control shaft 72 that is opposite interfacing portion 74 is configured to be received within an aperture, shown as support bore 84 of base member 20. Support bore 84 can be positioned at a front portion 22 (e.g., a front end 22) of track 88 or base member 20. Control shaft 72 can be supported at interfacing portion 74 through the slidably rotatable coupling of interfacing portion 74 at control bore 78 and supported at an opposite end with support bore 84. The end of control shaft 72 that is received within control bore 78 may slidably couple with support bore 84.

Control shaft 72 extends along substantially an entire length of track 88. Control shaft 72 can be rotated to drive first control member 86a and second control member 86b to translate in opposite directions along track 88. For example, rotating control shaft 72 in a first direction (e.g., clockwise) can drive first control member 86a and second control member 86b to translate towards each other (e.g., to translate closer together), while rotating control shaft 72 in a second direction that is opposite the first direction (e.g., counterclockwise) can drive first control member 86a and second control member 86b to translate away from each other (e.g., to translate farther apart). Control shaft 72 can be configured to remain translatably stationary (e.g., to rotate but not translate). For example, an engagement member 82 can be configured to be received within a receiving slot 92 (see FIG. 9). Engagement member 82 can extend into receiving slot 92 and interface with (e.g., couple with) a correspondingly shaped portion 94 of control shaft 72. Engagement member 82 can include a recess (e.g., a semi-circular recess) that is configured to interface with a shoulder defined by interfacing portion 74 of control shaft 72.

First control member 86a and second control member 86b include angled protrusions 97. First control member 86a includes angled protrusion 97a and second control member 86b includes angled protrusion 97b. Angled protrusions 97 are configured to be received within and translate relative to correspondingly shaped/angled tracks, grooves, recessions, control channels, channels, etc., shown as tracks 102 of body member 26. Tracks 102 can each include a slot, a recession, a track, etc., shown as slots 104. Slots 104 are configured to slidably couple with a corresponding tab, protrusion, post, pin, etc., of first control member 86a and second control member 86b, shown as pin 124 (see FIG. 12). Specifically, angled protrusions 97 can include a first surface, shown as exterior surface 98, and a second surface that is opposite exterior surface 98 (e.g., an interior surface). Pins 124 of first and second control members 86 extend from the second/interior surface of first and second control members 86. Pins 124 are configured to be received within slots 104 and can slidably engage with slots 104 (see FIG. 12).

First control member 86a and second control member 86b can cooperatively define an opening, a space, a cavity, a recess, a window, etc., shown as window 106 therebetween. For example, angled protrusion 97a and angled protrusion 97b can cooperatively define window 106 therebetween. In some embodiments, window 106 defined therebetween angled protrusion 97a and angled protrusion 97b corresponds in shape to interfacing protrusion 108 of body member 26. Interfacing protrusion 108 of body member 26 is configured to be received therewithin window 106. Interfacing protrusion 108 facilitates maintaining relative stability between adjustable assembly 14 and base assembly 12 even as adjustable assembly 14 is expanded relative to base assembly 12. Interfacing protrusion 108 also defines tracks 102 (e.g., opposite sides of interfacing protrusion 108 define one side of tracks 102).

In some embodiments, first control member 86a and second control member 86b are configured to slidably engage and translate along track 88 such that exterior surfaces 98a and 98b are flush (e.g., extend outwards to) with an outer most surface of base member 20. For example, exterior surfaces 98 of first control member 86a and second control member 86b can be substantially flush with (e.g., parallel with, extend outwards to, etc.) an exterior surface 110 of base member 20. In some embodiments, exterior surfaces 98a and 98b are sub-flush with exterior surface 110 of base member 20. In some embodiments, first control member 86a and second control member exterior surfaces 98a and 98b are sub-flush with exterior surface 110 of base member 20. In some embodiments, first control member 86a and second control member 86b are substantially parallel with each other. For example, exterior surface 98a and exterior surface 98b of first control member 86a and second control member 86b can be substantially parallel with each other.

First control member 86a and second control member 86b can be substantially similar to each other. For example, first control member 86a and second control member 86b may be mirror images of each other. Angled protrusion 97a and angled protrusion 97b can be angled at a same angle. For example, angled protrusion 97a can be angled at 60 degrees relative to a central (e.g., a longitudinal) axis that track 88 extends along and control members 86 are configured to translate along. Likewise, angled protrusion 97b can be angled at 60 degrees in an opposite direction relative to the central (e.g., the longitudinal) axis that track 88 extends along and control members 86 are configured to translate along.

First control member 86a and second control member 86b can include protrusions 112 that form a generally square frustum. Protrusions 112 can be configured to be received within and slidably interface with a correspondingly shaped cavity 114 of body member 26. Cavity 114 of body member 26 is positioned between rear portion 28 and front portion 30. Cavity 114 can have a generally square frustum shape and is configured to receive protrusions 112 therewithin. Cavity 114 and protrusions 112 can be slidably coupled with each other. Cavity 114 facilitates stability between adjustable assembly 14 and base assembly 12. In some embodiments, cavity 114 facilitates stability between adjustable assembly 14 and base assembly 12 despite a current degree of expansion of implant 10. The slidable coupling between cavity 114 and protrusions 112 can facilitate expansion and retraction of implant 10.

For example, protrusions 112 can each include an angled surface 116. Angled surface 116a and 116b are configured to slidably interface with correspondingly angled surfaces of cavity 114. As first control member 86a and second control member 86b are driven to translate apart from each other along track 88 (due to rotation of control shaft 72), the slidable coupling/interface between angled surfaces 116 of protrusions 112 and the correspondingly angled surfaces of cavity 114 drives adjustable assembly 14 to translate (e.g., expand, raise, etc.) relative to base assembly 12 in direction 118. Likewise, as first control member 86a and second control member 86b are driven to translate towards each other along track 88 (due to rotation of control shaft 72), the slidable coupling/interface between angled surfaces 116 of protrusions 112 and the correspondingly angled surfaces of cavity 114 drives adjustable assembly 14 to translate (e.g., retract, lower, compress, etc.) relative to base assembly 12 in a direction opposite direction 118.

When implant 10 is fully retracted (e.g., fully compressed, collapsed, fully collapsed, etc.), an upper surface of protrusions 112 may be substantially flush (e.g., co-planar with) an upper/exterior surface of body member 26. In some embodiments, when implant 10 is fully retracted (e.g., fully compressed), the upper surface of protrusions 112 is sub-flush the upper/exterior surface of body member 26.

In some embodiments, angled protrusions 97a and 97b overhang a shoulder 120 of track 88. For example, a bottom portion of angled protrusions 97a and 97b may project/protrude downwards in a direction opposite direction 118. In some embodiments, track 88 is a shelf including shoulder 120 and first control member 86a and second control member 86b slidably couple with and overhang the shelf (e.g., overhang track 88 at shoulder 120).

The slidable coupling between pins 124 that extend from the second surface that is opposite exterior surfaces 98 and slots 104 also facilitates expansion/retraction of adjustable assembly 14 relative to base assembly 12. For example, as control shaft 72 is rotated in a first direction (e.g., by a surgeon), first control member 86a and second control member 86b are driven to translate apart from each other along track 88. Pins 124 that extend from the second surface opposite exterior surfaces 98 of each of the first control member 86a and the second control member 86b are thereby driven to translate apart from each other. As pins 124 that extend from the second surface opposite exterior surfaces 98 translate apart from each other, adjustable assembly 14 is driven to translate (e.g., expand) in direction 118 relative to base assembly 12. Pins 124 slide along slots 104 as first control member 86a and second control member 86b are driven to translate apart from each other along track 88, thereby raising (e.g., expanding implant 10) adjustable assembly 14 relative to base assembly 12. Likewise, control shaft 72 can be rotated in an opposite direction to translate first control member 86a and second control member 86b towards each other (e.g., to decrease distance 122 between first control member 86a and second control member 86b), thereby translating pins 124 that extend from the second surface opposite exterior surfaces 98 along slots 104 and lowering (e.g., retracting implant 10) adjustable assembly 14 relative to base assembly 12.

Exterior surfaces of angled protrusions 92 are slidably coupled with correspondingly angled and oriented interior surfaces of tracks 102. The slidable and angled orientation of the exterior surfaces of angled protrusions 92 and the correspondingly angled and oriented interior surfaces of tracks 102 also facilitates expansion and retraction of adjustable assembly 14 relative to base assembly 12. For example, as first control member 86a and second control member 86b are driven to translate apart from each other along track 88, the exterior surfaces of angled protrusions 97a and 97b also translate apart from each other. This results in adjustable assembly 14 expanding (e.g., translating in direction 118) relative to base assembly 12, due to the slidable coupling between the exterior surfaces of angled protrusions 97 and the correspondingly angled and oriented interior surfaces of tracks 102.

In this way, control shaft 72 can be rotated in either direction to raise/lower adjustable assembly 14 relative to base assembly 12, thereby expanding or retracting implant 10. Advantageously, this allows a surgeon to implant 10 in the fully retracted state (shown in FIGS. 1-5), and then expand implant 10 by rotating control shaft 72 to translate adjustable assembly 14 in direction 118 relative to base assembly 12. The surgeon may rotate control shaft 72 to expand implant 10 to a fully expanded position (as shown in FIGS. 7, 9, 10, and 11) or to a partially expanded position, as desired.

Referring particularly to FIG. 9, body member 26 includes a protrusion, a column, a post, a guide post, etc., shown as guide protrusion 126, according to some embodiments. Guide protrusion 126 of body member 26 is configured to slidably couple with a corresponding groove, channel, track, recession, etc., of base member 20, shown as guide channel 128. Guide protrusion 126 and guide channel 128 can have corresponding cross-sectional shapes to facilitate slidable coupling therebetween. In some embodiments, guide protrusion 126 translates along guide channel 128 as implant 10 is expanded and retracted. Guide protrusion 126 and guide channel 128 facilitate stability between base assembly 12 and adjustable assembly 14 as implant 10 is expanded and retracted.

Figure 6:
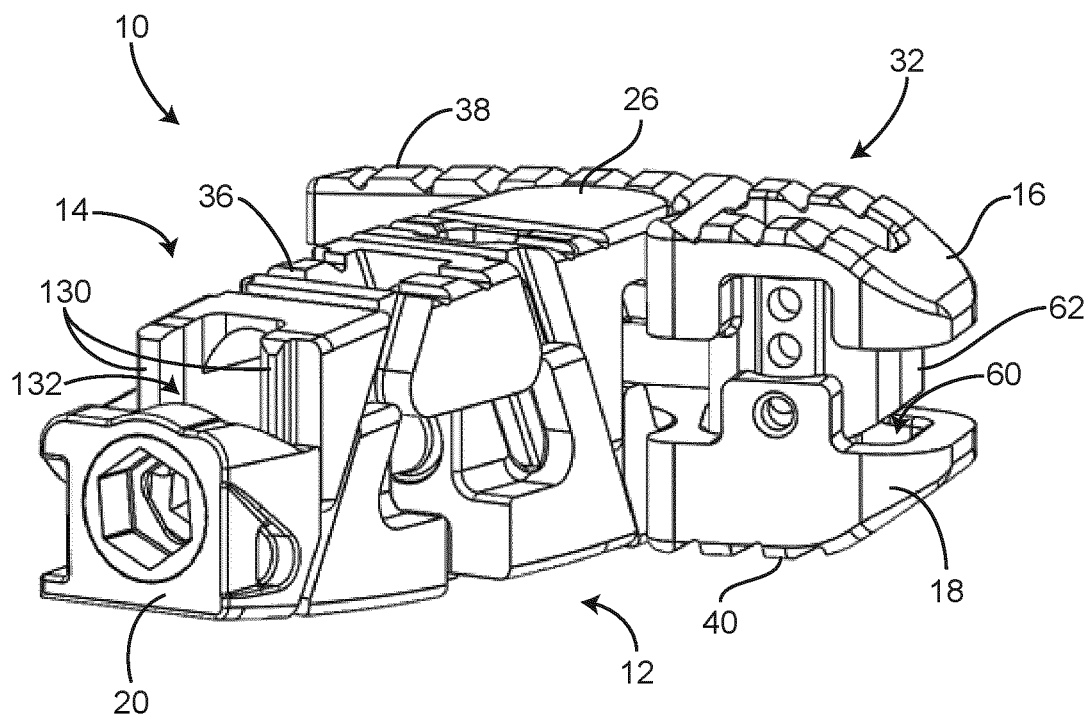
FIG. 6 is a perspective view of the implant of FIG. 1 in an expanded configuration, according to one embodiment
Figure 7:
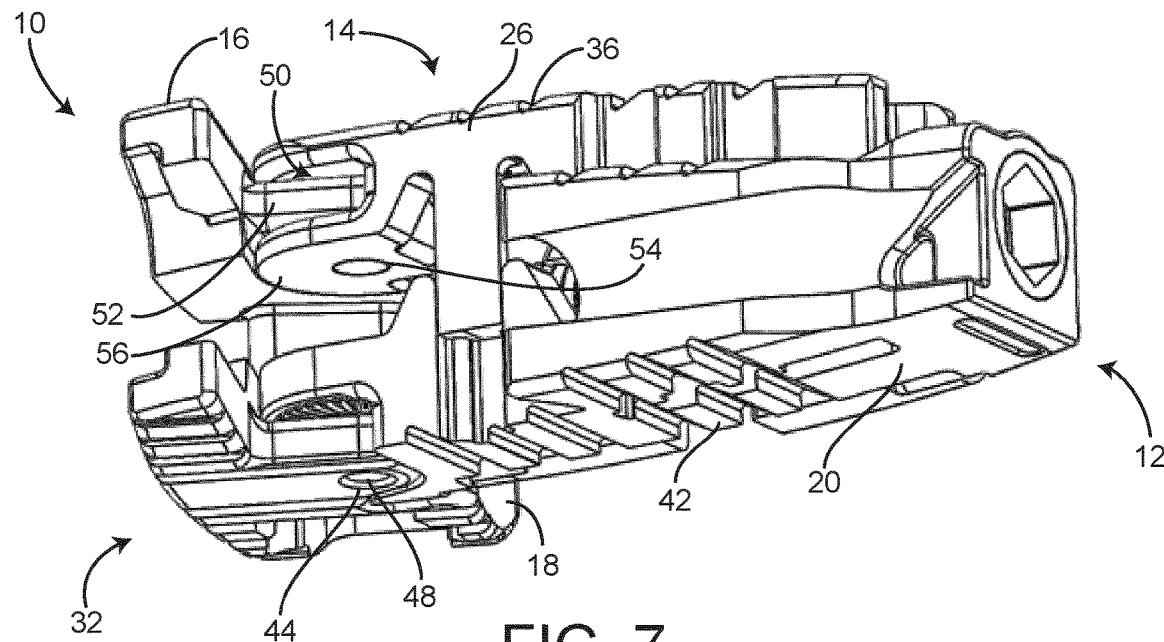
FIG. 7 is a perspective view of the implant of FIG. 1 in an expanded configuration, according to one embodiment.

Referring particularly to FIGS. 6 and 11, body member 26 includes one or more (e.g., a pair) of protrusions, track members, ridges, elongated protrusions, etc., shown as guide members 130. Guide members 130 of body member 26 are configured to slidably interface with correspondingly shaped grooves, channels, tracks, recesses, etc., of base member 20, shown as channels 132. Guide members 130 and channels 132 can be slidably coupled with each other. Guide members 130 can translate along channels 132 as implant 10 is expanded and retracted. The slidable coupling between guide members 130 and channels 132 facilitates stability between base assembly 12 and adjustable assembly 14 as implant 10 is expanded and retracted.

Referring particularly to FIG. 10, rotatable base member 18 can include a first portion 170 and a second portion 172. In some embodiments, first portion 170 and second portion 172 are positioned on opposite sides of the rotatable/pivotal coupling between rotatable base member 18 and base member 20. In some embodiments, second portion 172 and first portion 170 extend in opposite directions. Second portion 172 can have an overall curved profile, a straight profile, etc. Second portion 172 is configured to facilitate adjustment of angular orientation of rotatable base member 18 relative to base member 20. For example, second portion 172 can include geometry configured to interface with an adjustment tool to facilitate rotation/pivoting of rotatable base member 18 relative to base member 20. In some embodiments, when rotatable base member 18 is in a fully un-rotated orientation (shown in FIGS. 1-4), second portion 172 is configured to be received within a recess, a groove, a shoulder, etc., of base member 20, shown as receiving recess 174. In this way, an exterior surface 176 of second portion 172 can be substantially in-line (e.g., in a contoured line) with an exterior surface 178 of base member 20. First portion 170 includes cavity 60, tracks 166, protrusions 64, and apertures 70. Cavity 60 can be configured to facilitate growth and engagement of bone therewithin.

Figure 5:
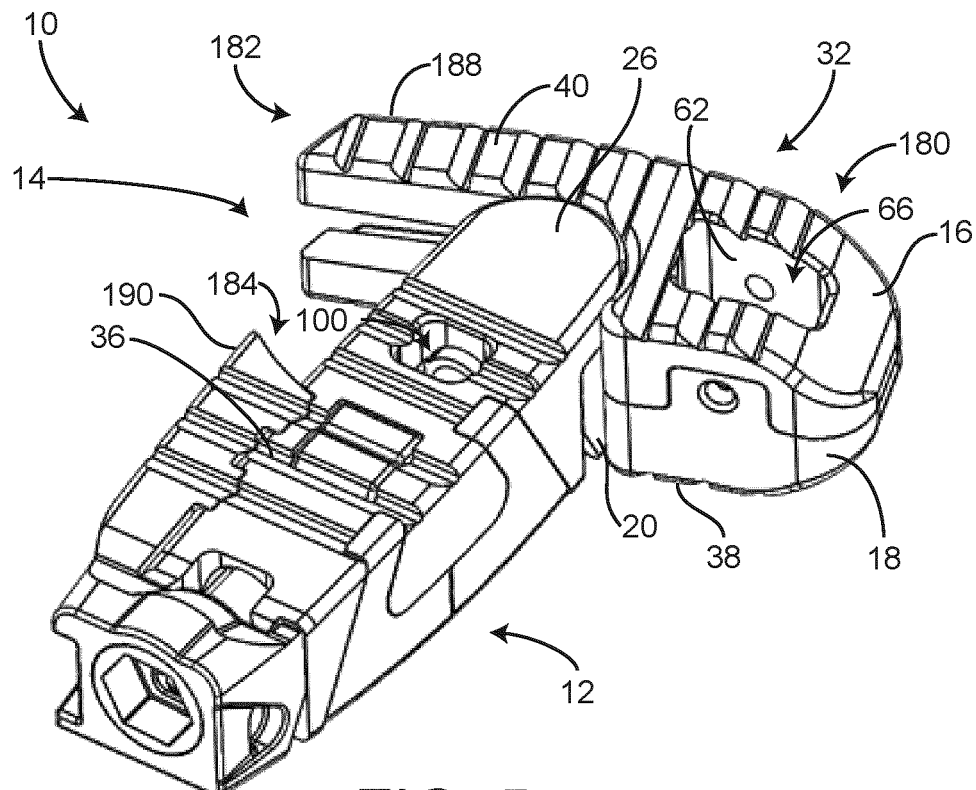
FIG. 5 is a perspective view of the implant of FIG. 1, according to one embodiment.

Referring particularly to FIG. 5, rotatable member 16 can have a similar shape or outer profile as rotatable base member 18. In some embodiments, rotatable member 16 has a same outer profile as rotatable base member 18. Rotatable member 16 includes a first portion 180 and a second portion 182. First portion 180 of rotatable member 16 can be similar to first portion 170 of rotatable base member 18. Likewise, second portion 182 of rotatable member 16 can be similar to second portion 172 of rotatable base member 18. First portion 180 of rotatable member 16 can include hollow protrusion 62, and cavity 66 that extends therethrough hollow protrusion 62 (e.g., the hollow portion of hollow protrusion 62).

Figure 3:
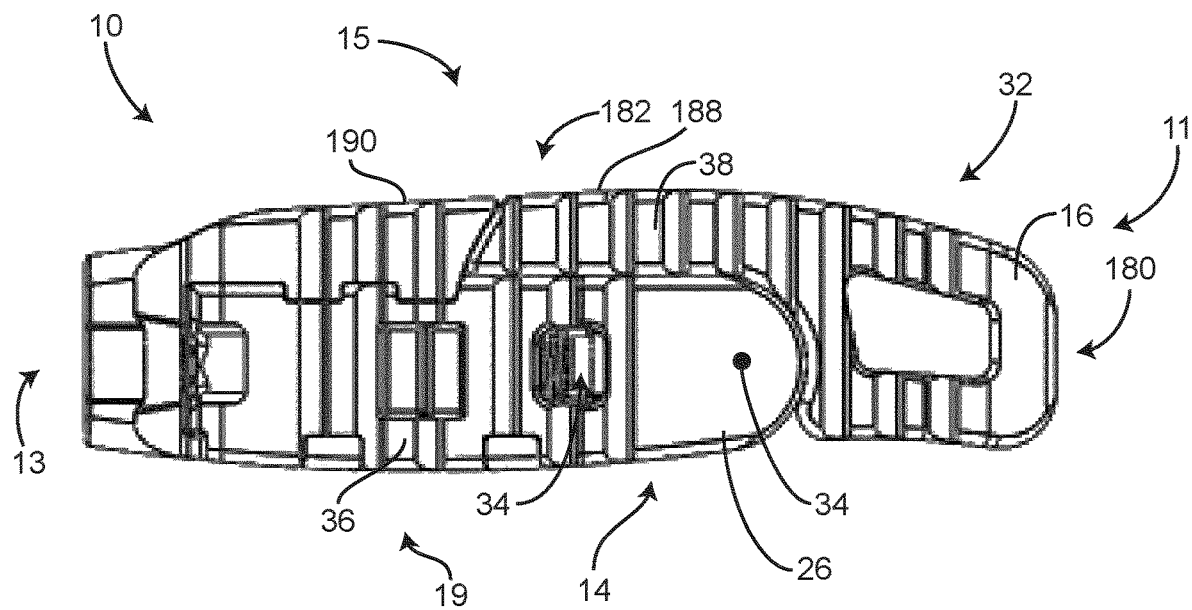
FIG. 3 is a top view of the implant of FIG. 1, according to one embodiment.
Figure 4:
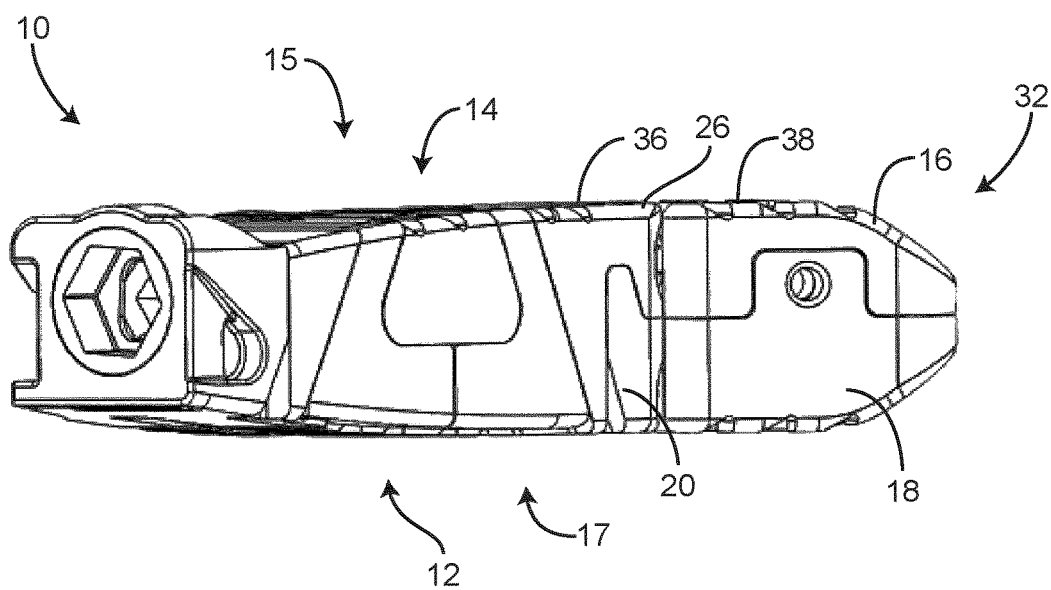
FIG. 4 is a perspective view of the implant of FIG. 1, according to one embodiment.

Second portion 182 of rotatable member 16 is configured to be received at a shoulder, a groove, a recess, etc., shown as receiving recess 184 of body member 26. Receiving recess 184 of body member 26 can receive second portion 182 of rotatable member 16 therewithin such that an exterior surface 188 of second portion 162 is substantially in-line (e.g., along a contoured line) with an exterior surface 190 of body member 26 (as shown in FIG. 3).

Referring particularly to FIGS. 13A-D and 14, the function of apertures 68 and apertures 70 is shown. Apertures 68 translate in direction 118 relative to apertures 70. As apertures 68 are driven to translate in direction 118 due to expansion of implant 10 (or in a direction opposite direction 118 due to retraction of implant 10), an area 1302 is formed therebetween apertures 68 and apertures 70. Area 1302 represents a line of sight through which light can pass through. As implant 10 is expanded, apertures 68 translate in direction 118 and area 1302 increases. Area 1302 may be visible through an x-ray. When apertures 68 and apertures 70 overlap, area 1302 is substantially circular. A surgeon can monitor the shape and size of area 1302 on an x-ray while adjusting (e.g., expanding) implant 10 to monitor a degree of extension/retraction of implant 10. Since apertures 68 are spaced apart at known distances, watching the size and shape of area 1302 provides the surgeon with knowledge regarding the current degree of extension/retraction of implant 10.

Figure 2:
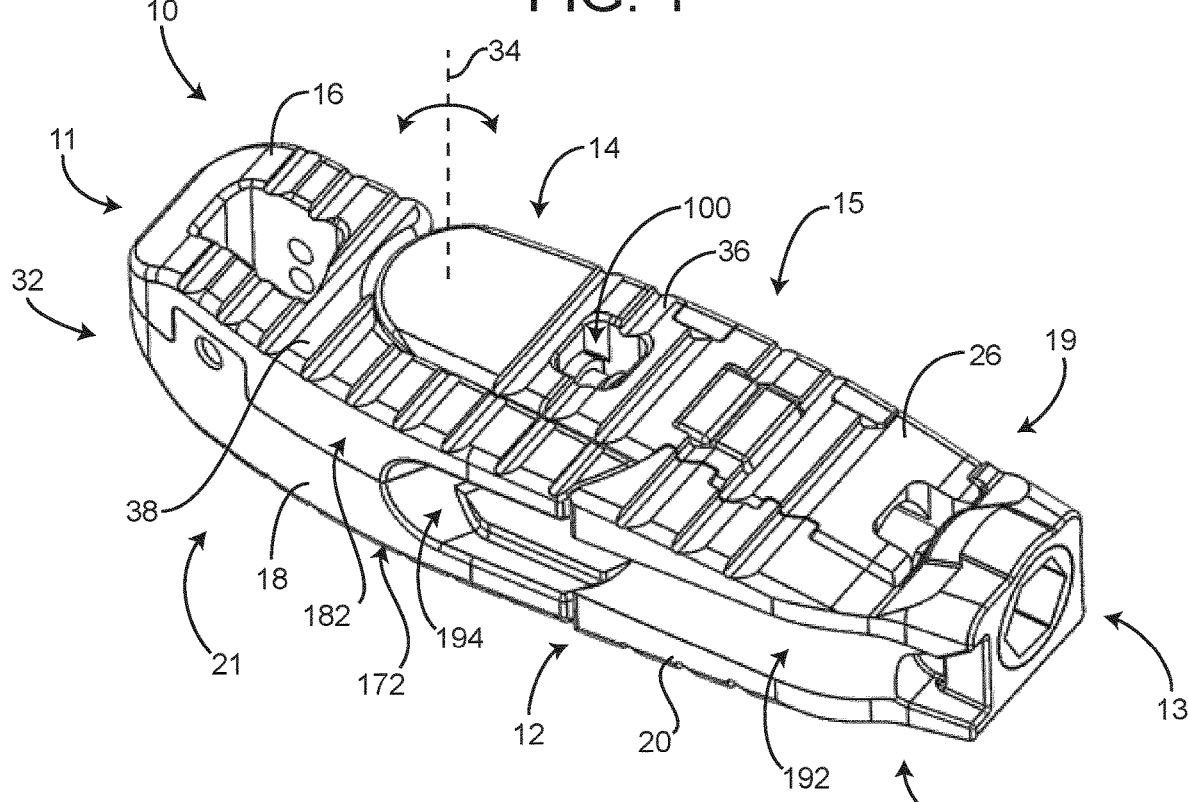
FIG. 2 is a perspective view of the implant of FIG. 1, according to one embodiment.

Referring particularly to FIG. 2, base member 20 of base assembly 12 and body member 26 of adjustable assembly 14 can define a channel, a groove, a track, a tool channel, a receiving recess, etc., therebetween, shown as receiving groove 192. Receiving groove 192 is configured to slidably interface with an adjustment tool therethrough.

Rotatable base member 18 of base assembly 12 and rotatable member 16 of adjustable assembly 14 similarly define a channel, a groove, a track, a receiving recess, etc., therebetween, shown as receiving groove 194. Receiving groove 194 can be defined between second portion 172 and second portion 182 of rotatable base member 18 and rotatable member 16, respectively. Receiving groove 194 can include channels, tracks, protrusions, recessions, etc., configured to removably couple rotatable base member 18 and rotatable member 16 with an adjustment tool. In some embodiments, a first adjustment tool is used to adjust an orientation of rotatable base member 18 and rotatable member 16 from the fully un-rotated configuration (as shown in FIG. 2) to a partially or completely rotated configuration (as shown in FIG. 5). In some embodiments, the first adjustment tool can be inserted into receiving groove 192 to adjust implant 10 from the fully un-rotated configuration. Receiving groove 192 can guide an end of the first adjustment tool to be received within receiving groove 194. The end of the first adjustment tool can be configured to interface with receiving groove 194 to exert a force on rotatable member 16 and rotatable base member 18, thereby producing rotation of rotatable member 16 and rotatable base member 18 in unison. The surgeon can then continue inserting the first adjustment member and providing a force to the portions of rotatable base member 18 and rotatable member 16 that form receiving groove 194 until rotatable base member 18 and rotatable member 16 are angled to a desired position. Insertion of the first adjustment tool can facilitate rotation of rotatable member 16 and rotatable base member 18 in a clockwise or first direction about central axis 34 (from the view of implant 10 shown in FIG. 2).

In order to rotate rotatable member 16 and rotatable base member 18 in a counter-clockwise direction or a second direction that is opposite the first direction, the surgeon can insert a second adjustment tool into receiving groove 192 and receiving groove 194. The surgeon can insert the second adjustment tool into receiving groove 192 in a first orientation until an end of the second adjustment tool interfaces with receiving groove 194. After the surgeon has fully inserted the second adjustment tool into receiving groove 192 in the first orientation such that the end of the second adjustment tool interfaces with receiving groove 194, the surgeon can rotate the second adjustment tool into a second orientation (e.g., rotate the second adjustment tool 90 degrees about its longitudinal axis) to removably couple the end of the second adjustment tool with receiving groove 194. The surgeon can then slide or draw back the second adjustment tool to rotate rotatable member 16 and rotatable base member 18 in the second (opposite) direction. The surgeon can continue sliding or drawing back the second adjustment tool until rotatable base member 18 and rotatable member 16 are in a desired angular configuration.

It should be noted that implant 10 may share various features with the other implants described herein, and be made of the same, similar, or different materials. For example, various components of implant 10 may be made of metal, plastic, composites, or other suitable bio-compatible materials. Further, implant 10 may be usable in connection with the spine or other parts of the body.

Referring now to FIGS. 15-24, an implant 200 is shown according to some embodiments. In some embodiments, implant 200 shares features, components, geometry, configurations, functionality, etc., with implant 10 as described in greater detail above with reference to FIGS. 1-14. Implant 200 can be operated (e.g., adjusted, expanded, rotated, etc.) similar to implant 10 and vice versa.

Referring particularly to FIGS. 15-19, implant 200 includes a base assembly 202 and an adjustable assembly 204, according to an exemplary embodiment. Base assembly 202 can be the same as or similar to base assembly 12 and may share various features with base assembly 12. Likewise, adjustable assembly 204 can be the same as or similar to adjustable assembly 14 and may share various features with adjustable assembly 14.

Referring particularly to FIGS. 20-24, implant 200 includes first control member 286a and second control member 286b. First control member 286a and second control member 286b of implant 200 can be similar to first control member 86a and second control member 86b. Particularly, both first control member 286a and second control member 286b of implant 200 can be the same as or similar to second control member 86b of implant 10.

First control member 286a and second control member 286b are configured to slidably couple with track 288 (see FIG. 24). Track 288 can be the same as or similar to track 88 of implant 10, according to some embodiments. Track 288 can have the form of a shelf, a groove, a surface, etc. First control member 286a and second control member 286b can be configured to slidably engage with a surface 292 of track 288. For example, a corresponding under-surface of first control member 286a and second control member 286b can slidably couple with surface 292. Surface 292 can be generally or substantially perpendicular with a vertical surface 294 of track 288. Surface 292 and vertical surface 294 define shoulder 290 therebetween. First control member 286a and second control member 286b can have a corresponding shaped portion 296 that slidably couples with at least one of surface 292, shoulder 290, and vertical surface 294. First control member 286a and second control member 286b can overhand shoulder 290 similar to how first control member 86a and second control member 86b overhand shoulder 120 of implant 10.

The slidable coupling between first and second control members 286 and track 288 is similar to the slidable coupling between first and second control members 86 and track 88 of implant 10. However, first and second control members 286 are configured to translate along track 88 in a same direction to expand or retract adjustable assembly 204 relative to base assembly 202.

First control member 286a and second control member 286b are driven to translate along track 288 by control shaft 272. Control shaft 272 can share any of the features, geometry, configuration, etc., of control shaft 72 of implant 10. For example, control shaft 272 can be configured to slidably couple with control bore 78. However, control shaft 272 includes threads 276 (e.g., control threads). Threads 276 can be right hand oriented threads or left hand oriented threads. Threads 276 are configured to threadingly couple with first control member 286a and second control member 286b. As control shaft 272 is rotated by a surgeon (e.g., with an adjustment tool), both first control member 286a and second control member 286b are driven to translate along track 288 in a same direction. For example, rotating control shaft 272 in a first direction (e.g., clockwise) can drive both first control member 286a and second control member 286b to translate along track 288 towards rear portion 24, while rotating control shaft 272 in a second direction that is opposite the first direction (e.g., counter-clockwise) can drive both first control member 286a and second control member 286b towards front portion 22 of track 288.

In some embodiments, translation of first and second control members 286 in a first direction along track 288 (e.g., towards rear portion 24 of track 288) drives adjustable assembly 204 to expand (e.g., translate upwards in direction 118 relative to base assembly 202), while translation of first and second control members 286 in a second direction that is opposite the first direction along track 288 drives adjustable assembly 204 to retract (e.g., to translate downwards in a direction opposite direction 118).

First and second control members 286 can each include an angled protrusion 297. For example, first control member 286a includes angled protrusion 297a and second control member 286b includes angled protrusion 297b. Angled protrusion 297a and angled protrusion 297b can function similarly as angled protrusion 97 of implant 10 to facilitate expansion and retraction of implant 200. However, angled protrusion 297a and angled protrusion 297b are both oriented at a same angle and are not symmetrically angled (as angled protrusions 97 are in implant 10). Angled protrusions 297 are configured to slidably couple/engage with correspondingly shaped and angled tracks, recesses, channels, control channels, etc., shown as tracks 222 of adjustable assembly 204. Tracks 222 are configured to receive angled protrusions 297 therewithin and can slidably couple with angled protrusions 297. As angled protrusions 297 translate due to translation of control members 286 along track 288, the slidable coupling/engagement between angled protrusions 297 and tracks 222 drives adjustable assembly 204 to expand or retract relative to base assembly 202. Tracks 222 can be the same as or similar to tracks 102 of implant 10. Tracks 222 can include slots for receiving a corresponding pin, post, protrusion, etc., of angled protrusions 297.

Adjustable assembly 204 also includes cavities, recesses, square frustum recesses, etc., shown as angled recesses 214 and 216. Angled recesses 214 and 216 are configured to receive and slidably engage corresponding portions, protrusions, etc., shown as protrusions 212 of control members 286. Protrusions 212 can be the same as or similar to angled protrusions 297 and may function similarly to angled protrusions 297 to expand and retract implant 200. Specifically, first control member 286a includes first protrusion 212a, while second control member 286b includes second protrusion 212b. Protrusions 212 can be similar and may extend parallel to each other. First protrusion 212a of first control member 286a is received within and slidably couples with angled recess 214. Likewise, second protrusion 212b of second control member 286b is received within and slidably couples with angled recess 216.

As control members 286 translate along track 288, protrusions 212 can drive adjustable assembly 204 to translate in direction 118 or a direction opposite direction 118 through the slidable coupling/engagement therebetween protrusions 212 and angled recesses 214 and 216. Adjustable assembly 204 is driven to translate relative to base assembly 202 due to the translation of both first control member 286a and second control member 286b in the same direction.

It should be noted that implant 200 may share various features with the other implants described herein, and be made of the same, similar, or different materials. For example, various components of implant 200 may be made of metal, plastic, composites, or other suitable bio-compatible materials. Further, implant 200 may be usable in connection with the spine or other parts of the body.

Referring now to FIGS. 25-35, an implant 300 is shown, according to another exemplary embodiment. Implant 300 can be the same as or similar to any of the other implants (e.g., implant 10, implant 200, etc.), and can share any of the features of any of the implants described herein.

Implant 300 includes a base assembly 302 and an adjustable assembly 304, according to an exemplary embodiment. Base assembly 302 is similar to and can be the same as base assembly 202 of implant 200. Likewise, adjustable assembly 304 is similar to and can be the same as adjustable assembly 304. Adjustable assembly 304 is configured to translate in direction 118 or in a direction opposite direction 118 relative to base assembly 302 to expand and retract implant 300.

Base assembly 302 includes base member 312 (e.g., a lower main support) and rotatable base member 318 (e.g., a lower pivoting support). Rotatable base member 318 is configured to pivotally or rotatably couple with base member 312 and is configured to pivot/rotate relative to base member 312 about central axis 34. Rotatable base member 318 can be similar to rotatable base member 18 of implant 10 and may share any of the features, geometry, and functionality of rotatable base member 18. Likewise, base member 312 can be similar to base member 20 of implant 10 and may share any of the features, geometry, and functionality of rotatable base member 20.

Adjustable assembly 304 includes body member 326 (e.g., an upper main support) and rotatable member 316 (e.g., an upper pivoting support). Body member 326 can be similar to body member 26 of implant 10 and may share any of the features, geometry, and functionality of body member 26. Likewise, rotatable member 316 can be similar to rotatable member 16 of implant 10 and may share any of the features, geometry, and functionality of body member 26.

Rotatable member 316 and rotatable base member 318 are configured to rotatably couple (e.g., pivotally couple) with body member 326 and base member 312, respectively. Rotatable member 316 and rotatable base member 318 may pivot or rotate about central axis 34 (see FIG. 31) in unison. Body member 326 and rotatable member 316 are configured to translate in direction 118 or a direction opposite direction 118 to expand or retract implant 300.

Referring particularly to FIGS. 30 and 32-33, implant 300 includes a control shaft 372, according to an exemplary embodiment. Control shaft 372 can be the same as or similar to control shaft 72 of implant 10 and can be configured to expand and retract implant 300 similar to control shaft 72. Control shaft 372 includes a first set of threads 376a and a second set of threads 376b (e.g., control threads), configured to threadingly couple with inner threads 377a and 377b of first control member 386a and second control member 386b, respectively.

First set of threads 376a and second set of threads 376b can be reverse oriented threads. For example, first set of threads 376a can be right hand oriented threads while second set of threads 376b are left handed threads (or vice versa). Inner threads 377a and 377b are oriented/configured to threadingly couple with threads 376a and 376b, respectively.

Base member 312 includes include tracks, grooves, recesses, channels, control channels, etc., shown as tracks 322. First control member 386a and second control member 386b include correspondingly shaped and angled protrusions, ridges, projections, etc., configured to slidably couple with tracks 322. In some embodiments, tracks 322 correspond in shape to an outer shape of first control member 386a and second control member 386b and are configured to receive and slidably couple with a portion of first control member 386a and second control member 386b.

As control shaft 372 is rotated, first control member 386a and second control member 386b are configured to translate along control shaft 372. First control member 386a and second control member 386b can be configured to translate in opposite directions due to rotation of control shaft 372. For example, when control shaft 372 is rotated in a first direction (e.g., clockwise), first control member 386a and second control member 386b can translate towards each other (due to the threaded coupling therebetween), while rotating control shaft 372 in a second direction that is opposite the first direction (e.g., counter-clockwise) drives first control member 386a and second control member 386b to translate away from each other.

Tracks 322a and 322b are angled and can be symmetric to each other. For example, track 322a and track 322b can be mirror images of each other. In some embodiments, track 322a and track 322b extend at equal yet opposite (e.g., mirrored) angles. For example, track 322a can extend at an angle of 60 degrees relative to a longitudinal axis of control shaft 372, while track 322b extends at an angle of 120 degrees relative to the longitudinal axis of control shaft 372 (assuming angles measured clockwise from the longitudinal axis of control shaft 372 are positive angles).

The slidable coupling between tracks 322 and control members 386 facilitates expansion and retraction of implant 300. For example, as control shaft 372 is rotated such that control members 386 translate apart from each other along threads 376 of control shaft 372, the slidable coupling between tracks 322 and control members 386 facilitates expanding implant 300 (e.g., translating adjustable assembly 304 away from base assembly 302). Likewise, rotating control shaft 372 such that control members 386 translate towards each other along threads 376 of control shaft 372 facilitates retracting implant 300 (e.g., translating adjustable assembly 304 towards base assembly 302) due to the slidable coupling between tracks 322 and control members 386. In this way, rotating control shaft 372 can drive implant 300 to expand and retract.

Referring particularly to FIGS. 36-43, the rotatable adjustment of rotatable member 316 and rotatable base member 318 is shown, according to some embodiments. Any of the implants of the present disclosure can be adjusted similarly as shown in FIGS. 36-43. For example, any of the implants of the present disclosure can include similar geometry as shown in FIGS. 36-43 configured to couple/interface with various adjustment tools described herein.

Referring particularly to FIGS. 36-39, a first adjustment tool 350 can be used to rotate rotatable member 316 and rotatable base member 318 about central axis 34 relative to body member 326 and/or base member 312. First adjustment tool 350 can be used to rotate rotatable member 316 and rotatable base member 318 in unison about central axis 34 in a first direction 35 (see FIG. 38).

First adjustment tool 350 includes an end portion 352 and a body portion 354. End portion 352 is configured to slidably engage with receiving groove 194 formed therebetween rotatable member 316 and rotatable base member 318. Body portion 354 can have a generally circular shape that corresponds to receiving groove 192. First adjustment tool 350 can be inserted into and slidably couple with receiving groove 192. Specifically, an outer periphery of body portion 354 can slidably couple/engage with an inner periphery of receiving groove 192. Receiving groove 192 facilitates aligning first adjustment tool 350 such that end portion 352 properly engages and couples with receiving groove 194.

First adjustment tool 350 can be inserted into receiving grooves 192 and 194 in a first orientation (shown in FIGS. 36 and 37) or a second orientation (shown in FIGS. 38 and 39). When first adjustment tool 350 is inserted into receiving grooves 192 and 194 in the first orientation, end portion 353 can slidably engage an outer surface or an outer periphery of receiving groove 194 and drive rotatable member 316 and rotatable base member 318 to pivot about central axis 34 in a first direction 37.

When first adjustment tool 350 is inserted into receiving grooves 192 and 194 in the second orientation, end portion 353 can slidably engage an inner surface or an inner periphery of receiving groove 194 and drive rotatable member 316 and rotatable base member 318 to pivot about central axis 34 in second direction 37 (shown in FIGS. 38 and 39). First adjustment tool 350 can be used to lock or align rotatable member 316 and rotatable base member 318 with base member 312 and body member 326. First adjustment tool 350 can be used by a surgeon to rotate rotatable member 316 and rotatable base member 318 from the configuration shown in FIGS. 25-29 to the configuration shown in FIG. 31.

Referring particularly to FIGS. 40-43, a second adjustment tool 351 can be used to rotate/pivot rotatable member 316 and rotatable base member 318 about central axis 34 in direction 37. Second adjustment tool 351 includes body portion 354 configured to slidably engage with receiving groove 192. In some embodiments, body portion 354 of second adjustment tool 351 is the same as or similar to body portion 354 of first adjustment tool 350.

To rotate rotatable base member 318 and rotatable member 316 in direction 37 about central axis 34, second adjustment tool 351 can be inserted in a first orientation (shown in FIGS. 40 and 41). Body portion 354 of second adjustment tool 351 slidably engages with an inner surface or an inner periphery of receiving groove 192. Receiving groove 192 facilitates aligning and guiding end portion 353 of second adjustment tool 351 into proper alignment with receiving groove 194.

End portion 353 of second adjustment tool 351 can have the form of a hook and is configured to selectively and removably couple with corresponding portions (e.g., corresponding protrusions) of receiving groove 194. When second adjustment tool 351 is in the first orientation, end portion 353 can pass substantially through receiving groove 194 as it is inserted. Once end portion 353 is inserted through receiving groove 194, second adjustment tool 351 can be rotated (e.g., ninety degrees) to removably and selectively couple end portion 353 of second adjustment tool 351 with rotatable base member 318 and rotatable member 316 (as shown in FIG. 42). After end portion 353 is coupled (e.g., hooked) with rotatable base member 318 and rotatable member 316, second adjustment tool 351 can be pulled or drawn backwards to pivot/rotate rotatable base member 318 and rotatable member 316 in direction 37 about central axis 34. The surgeon can thereby use second adjustment tool 351 to rotate rotatable member 316 and rotatable base member 318 to a desired angular position in direction 37.

First adjustment tool 350 and second adjustment tool 351 can be different portions of one adjustment tool. For example, first adjustment tool 350 and second adjustment tools 351 may be opposite ends of a single adjustment tool.

Referring particularly to FIG. 35, rotatable base member 318 can include a column, a protrusion, an alignment member, an elongated member, etc., shown as alignment protrusion 320. Alignment protrusion 320 can slidably engage or slidably couple with a channel, a groove, a track, a recess, etc., shown as groove 324 of rotatable member 316. In some embodiments, alignment protrusion 320 is configured to be received within groove 324. The slidable coupling between groove 324 and alignment protrusion 320 facilitates stability between rotatable base member 318 and rotatable member 316 as adjustable assembly 304 is translated relative to base assembly 302 and as rotatable base member 318 and rotatable member 316 are pivoted about central axis 34.

Referring particularly to FIG. 34, base member 312 includes protrusions, alignment protrusions, extensions, alignment members, elongated members, etc., shown as alignment protrusions 328 and 330. Alignment protrusions 328 and 330 are configured to extend into and be received within tracks, receiving portions, grooves, recesses, etc., shown as grooves 332 and 334 of body member 326. Specifically, alignment protrusion 328 is configured to be received within and slidably engage/couple with groove 332. Likewise, alignment protrusion 330 is configured to be received within and slidably engage/couple with groove 334. The slidable coupling between alignment protrusions 328 and 330 and grooves 332 and 332 facilitates stability between base member 312 and body member 326 as implant 300 is expanded and retracted. Alignment protrusions 328 and 330 and the corresponding grooves 332 and 334 can be spaced apart from each other and may extend from a same side of base member 312.

Referring still to FIG. 34, base member 312 can include a protrusion, a ridge, a crest, an alignment protrusion, etc., shown as central alignment protrusion 336. Central alignment protrusion 336 can be positioned between alignment protrusions 328 and 330. Central alignment protrusion 336 can extend in a same direction (e.g., upwards) as alignment protrusions 328 and 330. Central alignment protrusion 336 is configured to be received within a corresponding groove, space, recess, etc., shown as recess 338 of body member 326. Central alignment protrusion 336 and recess 338 can be slidably coupled with each other. In some embodiments, recess 338 is correspondingly shaped to central alignment protrusion 336. Central alignment protrusion 336 and recess 338 facilitate stability between base member 312 and body member 326 as implant 300 is expanded and retracted.

It should be noted that implant 300 may share various features with the other implants described herein, and be made of the same, similar, or different materials. For example, various components of implant 300 may be made of metal, plastic, composites, or other suitable bio-compatible materials. Further, implant 300 may be usable in connection with the spine or other parts of the body.

Referring now to FIGS. 44-71, an expandable implant 710 is shown according to an exemplary embodiment. Implant 710 may share many of the features of the other inter/intrabody implants discussed elsewhere herein. All such combinations of features are to be understood to be within the scope of the present disclosure. While implant 710 shares various characteristics with the other implants disclosed herein in structure and function, implant 710 further includes pivoting members that enable expansion/modification of the "footprint" of implant 710. As such, implant 710 provides both height and width adjustment features to accommodate various implantation requirements.

According to an exemplary embodiment, implant 710 includes an upper main support 712 and a lower main support 714 that collectively form a main assembly. Implant 710 further includes an upper pivoting support 716 and a lower pivoting support 718 that collectively form a pivoting assembly. The main assembly is rotatably coupled to the pivoting assembly. As discussed in greater detail herein, upper main support 712, lower main support 714, upper pivoting support 716, and lower pivoting support 718 move relative to one another in particular manners to provide desired adjustment capabilities for implant 710. As shown in FIG. 46, upper pivoting support 716 and lower pivoting support 718 (e.g., the pivoting assembly) pivot together about upper main support 712 and lower main support 714 (e.g., the main assembly). Furthermore, as shown in FIGS. 47-48, upper main support 712 and upper pivoting support 716 move (e.g., linearly) relative to lower main support 714 and lower pivoting support 718. Referring to FIG. 49, a control shaft 720 is received by lower main support 714. First and second control members 722, 724 are received on control shaft 720 and are movable along control shaft 720 to adjust a position of implant 710 between a collapsed position, as shown in FIGS. 44-46, and an expanded position, as shown in FIGS. 47 and 48. Guide pins 728 facilitate pivotal movement between upper main support 712 and upper pivoting support 716, and a pivot pin 726 facilitates pivotal movement between lower main support 714 and lower pivoting support 718.

Referring now to FIGS. 57-58, in one embodiment, upper main support 712 includes a first or proximal end 730 and a second or distal end 732. A top surface 734 defines teeth or projections 736 formed by corresponding grooves. Projections 736 are configured to engage adjacent portions of bone. Upper main support 712 further includes an upper pivot plate 738 defining a pivot guide 740 in a lower surface of pivot plate 738. In one embodiment, pivot guide 740 is an arcuate groove that defines a path of travel for upper pivoting support 716 about upper main support 712. Pivot guide 740 receives guide pins 728, as discussed in further detail below and shown, for example, in FIGS. 65-66. It should be noted that the relative positions of the pivot plates, pivot recess, and similar components may be reversed according to various alternative embodiments, and all such combinations of features are to be understood to be within the scope of the present disclosure.

Upper main support 712 further includes alignment guides 741 and alignment recesses 742. Alignment guides 741 and alignment recesses 742 are received in corresponding recesses and guides (e.g., alignment recesses 777 and alignment guides 776) in lower main support 714 to maintain a desired degree of alignment between components (e.g., to provide for linear relative movement, non-linear or angled relative movement, etc.) (see, e.g., FIG. 47). Upper main support 712 further defines a central cavity 735. A first control channel 744 is configured to receive first control member 722 and a second control channel 746 is configured to receive second control member 724. In some embodiments, control members 722, 724 are received in control channels 744, 746 in a sliding manner such that control members 722, 724 are able to translate within control channels 744, 746. In further embodiments, control channels 744, 746 have a shape such that control channels 744, 746 surround control members 722, 724 and at least partially correspond in shape to control members 722, 724. Control channels 744, 746 may be configured to provide any desired form of relative movement between components, as discussed in greater detail herein. As such, control channels 744, 746 may have the same or different slopes, be parallel or non-parallel, etc. All such features discussed elsewhere herein are to be understood to be applicable to the embodiment of implant 710.

Referring now to FIGS. 59-60, in one embodiment, lower main support 714 includes a first or proximal end 750 and a second or distal end 752. An upper surface 754 includes teeth or projections 756 formed by corresponding grooves, and a lower surface 758 includes teeth or projections 760 formed by corresponding grooves. Projections 756, 760 are configured to engage adjacent portions of bone. An aperture 762 provides fluid communication from an exterior of implant 710 to central cavity 735 to enable bone growth etc. Lower main support 714 includes a pivot recess 764 and a counterbore 766 that receives pivot pin 726 and extend to pivot recess 764. A proximal recess 768 and control bore 778 receive control shaft 720 and enable rotatable movement of control shaft 720 relative to lower main support 714. A tool recess 774 facilitates placement and repositioning of implant 710 in a desired position.

Lower main support 714 further includes extending portions 772 that define a tool channel 770. As shown in FIG. 60, extending portions 772 extend laterally from a remainder of lower main support 714 and provide an elongated channel to receive a tool (e.g., tool 820) usable to manipulate implant 710.

In some embodiments, lower main support 714 includes alignment guides 776 and alignment recesses 777. Alignment guides 776 and alignment recesses 777 are received in corresponding recesses and guides (e.g., alignment recesses 742 and alignment guides 741) in upper main support 712 to maintain a desired degree of alignment between components (e.g., to provide for linear relative movement, non-linear or angled relative movement, etc.) (see, e.g., FIG. 47).

Referring now to FIGS. 61-62, in one embodiment, upper pivoting support 716 includes a first or proximal end 780 and a second or distal end 782. A top surface 784 defines teeth or projections 786 formed by corresponding grooves. Projections 786 are configured to engage adjacent portions of bone. A pivot recess or groove 792 is configured to slidably receive upper pivot plate 738 of upper main support 712. Guide pin apertures 794 receive guide pins 728 such that guide pins 728 are received within pivot guide 740 of upper pivot plate 738. Upper pivoting support 716 includes an inner edge surface 791 that generally conforms to the shape of distal end 732 of upper main support 712.

In some embodiments, upper pivoting support 716 includes upper alignment columns 788 and upper alignment recesses 790 that are configured to be received by corresponding recesses and columns (e.g., lower alignment recesses 814 and lower alignment columns 812) provided on lower pivoting support 718 to maintain a desired degree of alignment between components (e.g., to provide for linear relative movement, non-linear or angled movement, etc.). In one embodiment, upper alignment columns 788 extend to and form part of the lower surface of implant 710 and include teeth or projections formed by corresponding grooves (e.g., similar to projections 786). Lower pivoting support 718 includes an edge surface 818 that generally conforms to the shape of distal end 752 of lower main support 714.

In one embodiment, upper pivoting portion 716 includes a tool guide portion 796. Tool guide portion 796 may include a contoured/curved surface configured to be engaged by a tool end and thereby guide pivotal movement of upper pivoting support 716 about upper main support 712. In some embodiments, tool guide portion 796 of upper pivoting support 716 generally conforms in shape to a corresponding tool guide portion (e.g., tool guide portion 816) on lower pivoting support 718. Further, the tool guide portions may be generally aligned with tool channel 770 provided by lower main support 714 such that a tool extending along tool channel 770 will engage tool guide portions 796, 816 (see, e.g., FIG. 67).

Referring now to FIGS. 63-64, in one embodiment, lower pivoting support 718 includes a first or proximal end 800 and a second or distal end 802. A lower surface 804 includes teeth or projections 806 formed by corresponding grooves. Projections 806 are configured to engage adjacent portions of bone. Lower pivoting support 718 includes a lower pivot plate 808 having an aperture 810. Lower pivot plate 808 is received by pivot recess 764 of lower main support 714, and aperture 810 receives pivot pin 726 therethrough, as also shown, for example, in FIGS. 65-66.

In some embodiments, lower pivoting support 718 includes lower alignment columns 812 and lower alignment recesses 814 that are configured to be received by corresponding recesses and columns (e.g., upper alignment recesses 790 and upper alignment columns 788) provided on upper pivoting support 716 to maintain a desired degree of alignment between components (e.g., to provide for linear relative movement, non-linear or angled movement, etc.). In one embodiment, lower alignment columns 812 extend to and form part of the upper surface of implant 710 and include teeth or projections formed by corresponding grooves (e.g., similar to projections 806).

In one embodiment, implant 710 is initially in an un-pivoted, collapsed state, as shown, for example, in FIGS. 44-45. In this configuration, the overall height and width of implant 710 are at a minimum, facilitating insertion of implant 710 into a desired position (see, e.g., FIG. 69). Further, in this configuration, projections 736 on upper main support 712 and projections 786 on upper pivoting support 716 are generally aligned and form a generally continuous surface for engagement with adjacent portions of bone. Similarly, projections 756 on lower main support 714 and projections 806 on lower pivoting support 718 are generally aligned and form a generally continuous surface for engagement with adjacent portions of bone.

Once implant 710 is in a desired position adjacent a vertebra 822, tool 820 may engage tool channel 770 and tool guide portions 796, 816, as shown in FIGS. 67-68, to rotate upper and lower pivoting supports 716, 718 about upper and lower main supports 712, 714. In some embodiments, pivoting of upper and lower pivoting supports 716, 718 results in an increase in the overall width, and footprint, of implant 710. As shown in FIG. 70, in some embodiments, upper and lower pivoting supports 716, 718 may be positioned to generally align with an anterior portion of one or more vertebrae (e.g., vertebra 822). In other embodiments, implant 710 may be placed in other desired positions.

After pivoting upper and lower pivoting supports 716, 718, implant 710 may be adjusted from a collapsed position to an expanded position, as shown in FIG. 71. In one embodiment, tool 820 may be used for both rotating and expanding adjustments of implant 710. For example, tool 820 may include a hex-shaped end configured to engage a corresponding recess in control shaft 720. Rotation of control shaft 720 causes corresponding movement of control members 722, 724, and expansion of upper main support 712 and upper pivoting support 716 relative to lower main support 714 and lower pivoting support 718.

In one embodiment, the control shaft 720 and control members 722, 724 are housed by upper and lower main supports 712, 714, and cause corresponding movement therebetween. Relative movement between upper pivoting support 716 and lower pivoting support 718 results from the coupling of upper pivoting support 716 to upper main support 712, and the coupling of lower pivoting support 718 to lower main support 714 (e.g., by way of upper and lower pivot plates 738, 808 and associated features). The various alignment features maintain a desired alignment between components during adjustment.

As shown in FIG. 71, once implanted, pivoted, and expanded to a desired configuration and position, implant 710 provides an implant that provides support to adjacent vertebrae. Furthermore, the various supports may be configured to accommodate a natural curvature of the spine (e.g., a lumbar curve), by providing, for example, increased height toward an anterior direction (e.g., toward anterior portion 824 of vertebra 822). Further yet, implant 710 enables a user to adjust both height and width of a single implant with a single tool, providing infinitely variable height and width adjustment capabilities.

It should be noted that implant 710 may share various features with the other implants described herein, and be made of the same, similar, or different materials. For example, various components of implant 710 may be made of metal, plastic, composites, or other suitable bio-compatible materials. Further, implant 710 may be usable in connection with the spine or other parts of the body.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic. For example, circuit A communicably "coupled" to circuit B may signify that the circuit A communicates directly with circuit B (i.e., no intermediary) or communicates indirectly with circuit B (e.g., through one or more intermediaries).

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

It is important to note that the construction and arrangement of the implants as shown in the various exemplary embodiments is illustrative only. Additionally, any element disclosed in one embodiment may be incorporated or utilized with any other embodiment disclosed herein. For example, the receiving groove described herein may be incorporated in implant 200. Although only one example of an element from one embodiment that can be incorporated or utilized in another embodiment has been described above, it should be appreciated that other elements of the various embodiments may be incorporated or utilized with any of the other embodiments disclosed herein.

What is claimed is:

1. An expandable implant, comprising:
    an upper main support configured to engage a first portion of bone;
    a lower main support coupled to the upper main support and configured to engage a second portion of bone, wherein the upper main support is adjustable relative to the lower main support to adjust a height of the expandable implant;
    an upper pivoting support configured to engage the first portion of bone, wherein the upper pivoting support is rotatably movable relative to the upper main support;
    a lower pivoting support coupled to the upper pivoting support and configured to engage the second portion of bone, wherein adjustment of the upper main support relative to the lower main support causes a corresponding adjustment of the upper pivoting support relative to the lower pivoting support, and wherein the lower pivoting support is rotatably movable relative to the lower main support;
    at least one alignment guide provided on one of the lower main support and the upper main support; and
    at least one alignment recess provided on the other of the lower main support and the upper main support and configured to receive the at least one alignment guide to maintain a desired alignment between the upper main support and the lower main support;
    wherein the at least one alignment guide and the at least one alignment recess limit the upper and lower main supports to linear relative motion;
    wherein the upper pivoting support is movable between a first position, where a first portion of the upper pivoting support is aligned with a longitudinal axis of the upper main support and a second portion of the upper pivoting support is adjacent a first side of the upper main support, and a second position, where the first portion of the upper pivoting support extends beyond a second side of the upper main support opposite the first side and in a first direction, and the second portion of the upper pivoting support extends beyond the first side of the upper main support in a second direction opposite the first direction.

2. The expandable implant of claim 1, wherein the upper pivoting support and the lower pivoting support rotate about distal ends of the upper main support and the lower main support.

3. The expandable implant of claim 1, further comprising a control shaft received in the lower main support and first and second control members threadingly received on the control shaft;
    wherein the upper main support includes a first control channel configured to receive at least a portion of the first control member and a second control channel configured to receive at least a portion of the second control member; and
    wherein rotation of the control shaft causes movement of the first control member along the control shaft and movement of the second control member along the control shaft to move the upper main support relative to the lower main support.

4. The expandable implant of claim 3, wherein the first control channel and the second control channel are angled towards each other, and wherein rotation of the control shaft causes movement of the first control member and the second control member along the control shaft in opposite directions to move the upper main support relative to the lower main support.

5. The expandable implant of claim 1, further comprising:
a tool channel formed in the lower main support; and
a space defined between the upper pivoting support and the lower pivoting support for engaging a tool end;
wherein the tool channel is configured to direct the tool end to the space defined between the upper pivoting support and the lower pivoting support to enable rotation of the upper and lower pivoting supports through application of a force to the upper pivoting support and the lower pivoting support from the tool end.

6. The expandable implant of claim 1, wherein the upper pivoting support and the lower pivoting support rotate about a common pivot axis.

7. An expandable implant, comprising:
an upper support assembly configured to engage a first portion of bone and including an upper main support and an upper pivoting support, wherein the upper pivoting support is rotatably movable relative to the upper main support;
a lower support assembly coupled to the upper support assembly, the lower support assembly configured to engage a second portion of bone and including a lower main support and a lower pivoting support, wherein the lower pivoting support is rotatably movable relative to the lower main support; and
a control assembly comprising a control shaft and a control member received on the control shaft, the control member configured to translate along the control shaft and slidingly engage the upper main support and the lower main support, wherein a height of the control shaft relative to the lower main support remains constant during adjustment of the upper support assembly relative to the lower support assembly;
wherein the upper support assembly is adjustable relative to the lower support assembly to adjust a height of the expandable implant by rotation of the control shaft;
wherein the upper pivoting support is movable between a first position, where a first portion of the upper pivoting support is aligned with a longitudinal axis of the upper main support and a second portion of the upper pivoting support is adjacent a first side of the upper main support, and a second position, where the first portion of the upper pivoting support extends beyond a second side of the upper main support opposite the first side and in a first direction, and the second portion of the upper pivoting support extends beyond the first side of the upper main support in a second direction opposite the first direction.

8. The expandable implant of claim 7, wherein the upper pivoting support and the lower pivoting support rotate about distal ends of the upper main support and the lower main support.

9. The expandable implant of claim 7, wherein the upper main support is translationally fixed relative to the upper pivoting support and the lower main support is translationally fixed relative to the lower pivoting support.

10. The expandable implant of claim 7, wherein the upper pivoting support comprises a plurality of apertures spaced apart that extend through an entire width of the upper pivoting support, and the lower pivoting support comprises one or more apertures, wherein a first set of the plurality of apertures of the upper pivoting support are configured to overlap the one or more apertures of the upper pivoting support to allow light to pass through.

11. The expandable implant of claim 10, wherein a second set of the plurality of apertures of the upper pivoting support are configured to overlap the one or more apertures of the lower pivoting support to allow light to pass through when the upper support assembly is adjusted relative to the lower support assembly to a predetermined height.

12. The expandable implant of claim 11, wherein the plurality of apertures of the upper pivoting support extend through a protrusion of the upper pivoting support, and wherein the lower pivoting support comprises a correspondingly shaped aperture configured to receive the protrusion of the upper pivoting support.

13. The expandable implant of claim 12, wherein the one or more apertures of the lower pivoting support extend through one or more protrusions of the lower pivoting support, wherein the one or more protrusions extend from an outer periphery of the correspondingly shaped aperture.

14. An expandable implant, comprising:
an upper main support configured to engage a first portion of bone;
a lower main support coupled to the upper main support and configured to engage a second portion of bone, wherein the upper main support is adjustable relative to the lower main support to adjust a height of the expandable implant;
an upper pivoting support configured to engage the first portion of bone, wherein the upper pivoting support is rotatably movable relative to the upper main support;
a lower pivoting support coupled to the upper pivoting support and configured to engage the second portion of bone, wherein adjustment of the upper main support relative to the lower main support causes a corresponding adjustment of the upper pivoting support relative to the lower pivoting support, and wherein the lower pivoting support is rotatably movable relative to the lower main support;
a tool channel formed in the lower main support; and
a space defined between the upper pivoting support and the lower pivoting support for engaging a tool end;
wherein the tool channel is configured to direct the tool end to the space defined between the upper pivoting support and the lower pivoting support to enable rotation of the first and second pivoting support members through application of a force to the upper pivoting support and the lower pivoting support from the tool end.

\* \* \* \* \*